US010231740B2

(12) United States Patent
Sholev et al.

(10) Patent No.: US 10,231,740 B2
(45) Date of Patent: Mar. 19, 2019

(54) ARTHROSCOPIC SURGICAL DEVICE

(71) Applicant: MININVASIVE LTD., Magal (IL)

(72) Inventors: Moti Sholev, Amikam (IL); Raphael Meloul, Ceasarea (IL); Ronen Raz, Magal (IL); Boaz Harari, Haifa (IL)

(73) Assignee: MININVASIVE LTD., Magal (IL)

( * ) Notice: Subject to any disclaimer, the term of this patent is extended or adjusted under 35 U.S.C. 154(b) by 781 days.

(21) Appl. No.: 14/370,884

(22) PCT Filed: Jan. 15, 2013

(86) PCT No.: PCT/IL2013/050030
§ 371 (c)(1),
(2) Date: Jul. 7, 2014

(87) PCT Pub. No.: WO2013/102909
PCT Pub. Date: Jul. 11, 2013

(65) Prior Publication Data
US 2015/0045795 A1 Feb. 12, 2015

Related U.S. Application Data

(60) Provisional application No. 61/584,267, filed on Jan. 8, 2012, provisional application No. 61/636,751, filed
(Continued)

(30) Foreign Application Priority Data

Aug. 23, 2012 (WO) ................. PCT/IL2012/000318
Aug. 23, 2012 (WO) ................. PCT/IL2012/000319

(51) Int. Cl.
*A61B 17/00* (2006.01)
*A61B 17/16* (2006.01)
(Continued)

(52) U.S. Cl.
CPC ...... *A61B 17/1604* (2013.01); *A61B 17/0469* (2013.01); *A61B 17/0482* (2013.01);
(Continued)

(58) Field of Classification Search
None
See application file for complete search history.

(56) References Cited

U.S. PATENT DOCUMENTS 2,579,192 A 12/1951 Kohl
5,250,055 A 10/1993 Moore et al.
(Continued)

FOREIGN PATENT DOCUMENTS

CN 101193600 9/2010
EP 1898812 3/2008
(Continued)

OTHER PUBLICATIONS

U.S. Appl. No. 61/636,751, filed Apr. 23, 2012.
(Continued)

*Primary Examiner* — Sameh Boles
(74) *Attorney, Agent, or Firm* — Sughrue Mion, PLLC

(57) ABSTRACT

An arthroscopic bone tunneling and suturing device including a bone-engaging needle driving assembly including a bone-engaging needle and being adapted for arthroscopic insertion into engagement with a patient's bone at a first bone location through an arthroscopic incision and for driving the needle forwardly along a generally arcuate tunneling path through the bone at least to a second bone location and a bone-engaging pin driving assembly arranged for operative engagement with the bone-engaging needle driving assembly and being adapted for arthroscopic insertion into engagement with a patient's bone at a third bone location through the arthroscopic incision.

14 Claims, 56 Drawing Sheets

Related U.S. Application Data on Apr. 23, 2012, provisional application No. 61/714,813, filed on Oct. 17, 2012.

(51) Int. Cl.
  *A61B 17/04* (2006.01)
  *A61B 17/88* (2006.01)
  *A61B 17/06* (2006.01)
  *A61B 17/29* (2006.01)

(52) U.S. Cl.
  CPC ...... *A61B 17/1642* (2013.01); *A61B 17/8861* (2013.01); *A61B 2017/0472* (2013.01); *A61B 2017/06042* (2013.01); *A61B 2017/06104* (2013.01); *A61B 2017/2923* (2013.01)

(56) References Cited

U.S. PATENT DOCUMENTS

| | | | |
|---|---|---|---|
| 5,387,221 | A | 2/1995 | Bisgaard |
| 5,499,991 | A | 3/1996 | Garman et al. |
| 5,665,096 | A | 9/1997 | Yoon |
| 5,681,333 | A | 10/1997 | Burkhart et al. |
| 5,961,530 | A | 10/1999 | Moore |
| 6,328,744 | B1 | 12/2001 | Harari |
| 6,443,963 | B1 | 9/2002 | Baldwin |
| 6,523,417 | B1 | 2/2003 | Donahue |
| 7,029,479 | B2 | 4/2006 | Tallarida |
| 7,097,648 | B1 | 8/2006 | Globerman et al. |
| 7,166,116 | B2 | 1/2007 | Lizardi et al. |
| 7,662,171 | B2 | 2/2010 | West, Jr. |
| 8,088,130 | B2 | 1/2012 | Kaiser et al. |
| 8,282,657 | B2 | 10/2012 | McClurg et al. |
| 2002/0040227 | A1 | 4/2002 | Harari |
| 2003/0078599 | A1 | 4/2003 | O'Quinn |
| 2006/0195121 | A1 | 8/2006 | Chu |
| 2006/0271060 | A1 | 11/2006 | Gordon |
| 2007/0005067 | A1 | 1/2007 | Dross |
| 2007/0179509 | A1 | 8/2007 | Nagata et al. |
| 2008/0109015 | A1 | 5/2008 | Chu et al. |
| 2008/0228224 | A1 | 9/2008 | Sauer |
| 2009/0012538 | A1 | 1/2009 | Saliman et al. |
| 2009/0062819 | A1 | 3/2009 | Burkhart |
| 2009/0069823 | A1 | 3/2009 | Foerster |
| 2009/0105729 | A1 | 4/2009 | Zentgraf |
| 2009/0105743 | A1 | 4/2009 | Chu |
| 2009/0131956 | A1 | 5/2009 | Dewey |
| 2009/0138029 | A1 | 5/2009 | Saliman et al. |
| 2009/0157076 | A1 | 6/2009 | Athas et al. |
| 2009/0206128 | A1 | 8/2009 | Hueil et al. |
| 2009/0270862 | A1 | 10/2009 | Arcenio |
| 2009/0312782 | A1 | 12/2009 | Park |
| 2010/0076436 | A1 | 3/2010 | Hajianpour |
| 2010/0106194 | A1 | 4/2010 | Bonutti et al. |
| 2010/0152751 | A1 | 6/2010 | Meade et al. |
| 2010/0191248 | A1 | 7/2010 | Mehta et al. |
| 2010/0198258 | A1 | 8/2010 | Heaven et al. |
| 2010/0318139 | A1 | 12/2010 | Beauchamp |
| 2011/0022063 | A1 | 1/2011 | McClurg |
| 2011/0106124 | A1 | 5/2011 | Beauchamp |
| 2012/0239085 | A1 | 9/2012 | Schlotterback et al. |
| 2012/0323248 | A1 | 12/2012 | Dross |
| 2013/0123810 | A1 | 5/2013 | Brown et al. |
| 2013/0144337 | A1 | 6/2013 | Stone et al. |
| 2013/0178854 | A1 | 7/2013 | Sholev et al. |
| 2013/0296931 | A1 | 11/2013 | Sengun |
| 2014/0214038 | A1 | 7/2014 | Sholev |
| 2014/0303625 | A1 | 10/2014 | Sholev |
| 2015/0258332 | A1 | 9/2015 | Bentley et al. |
| 2015/0351743 | A1 | 12/2015 | Stiggelbout |
| 2015/0351759 | A1 | 12/2015 | Bennett et al. |

FOREIGN PATENT DOCUMENTS

| | | |
|---|---|---|
| EP | 1970016 A1 | 9/2008 |
| EP | 2698128 A1 | 2/2014 |
| GB | 2154484 | 9/1985 |
| JP | 833635 A | 2/1996 |
| JP | H10-52431 | 2/1998 |
| JP | 8509918 A | 9/2001 |
| JP | 2003-501132 A | 1/2003 |
| JP | 2008-510526 A | 4/2008 |
| JP | 2008-546489 A | 12/2008 |
| JP | 5474996 | 4/2014 |
| WO | 96/27331 | 9/1996 |
| WO | 9747246 A1 | 12/1997 |
| WO | 2000/74578 | 12/2000 |
| WO | 2002/007609 | 1/2002 |
| WO | 2009/107121 | 9/2009 |
| WO | 10/056785 | 5/2010 |
| WO | 10/056786 | 5/2010 |
| WO | 10/056787 | 5/2010 |
| WO | 2011160166 A1 | 12/2011 |
| WO | 2012/007941 | 1/2012 |
| WO | 2013/027209 | 2/2013 |
| WO | 2013/027210 | 2/2013 |
| WO | 2013/071234 | 5/2013 |
| WO | 2013/102909 | 7/2013 |
| WO | 2014/147619 | 9/2014 |
| WO | 2017/051404 | 3/2017 |

OTHER PUBLICATIONS

U.S. Appl. No. 61/584,267, filed Jan. 8, 2012.
U.S. Appl. No. 61/526,717, filed Aug. 24, 2011.
U.S. Appl. No. 61/363,247, filed Jul. 11, 2010.
U.S. Appl. No. 61/714,813, filed Oct. 17, 2012.
An International Search Report and a Written Opinion both dated Jan. 23, 2013, which issued during the prosecution of Applicant's PCT/IL2012/000318.
An International Search Report and a Written Opinion both dated Dec. 5, 2011, which issued during the prosecution of Applicant's PCT/IL2011/000549.
An International Search Report and a Written Opinion both dated May 10, 2013 which issued during the prosecution of Applicant's PCT/IL2013/050030.
An International Search Report dated Jan. 8, 2013 which issued during the prosecution of Applicant's PCT/IL2012/000319.
An English translation of an Office Action dated Jul. 3, 2014 which issued during the prosecution of Chinese Patent Application 2011800437287.
An International Search Report and Written Opinion both dated Jul. 11, 2014, which issued during the prosecution of Applicant's PCT/IL 14/50299.
An International Preliminary Search Report dated Aug. 26, 2014, which issued during the prosecution of Applicant's PCT/IL2013/050030.
An International Preliminary Report dated Feb. 25, 2014 which issued during the prosecution of Applicant's PCT/IL2012/000319.
Written Opinion dated Jan. 8, 2013 which issued during the prosecution of Applicant's PCT/IL2012/000319.
An International Preliminary Report dated Feb. 25, 2014 which issued during the prosecution of Applicant's PCT/IL2012/000318.
An Office Action dated Apr. 5, 2014 which issued during the prosecution of Australian Patent Application No. 2011277949.
An English translation of an Office Action dated Mar. 24, 2015, which issued during the prosecution of Japanese Patent Application No. 519213/2013.
European Search Report dated Jan. 17, 2017, which issued during the prosecution of Applicant's European App No. 14769413.7.
An Office Action dated Mar. 21, 2017, which issued during the prosecution of U.S. Appl. No. 14/240,227.
An Office Action dated Mar. 20, 2017, which issued during the prosecution of U.S. Appl. No. 14/240,082.
An Office Action dated Nov. 22, 2016 which issued during the prosecution of Japanese Patent Application No. 550801/2014.
An Office Action dated Oct. 13, 2016, which issued during the prosecution of U.S. Appl. No. 14/240,082.
An Office Action dated Jul. 11, 2016, which issued during the prosecution of Australian Patent Application No. 2012298197.

(56) References Cited

OTHER PUBLICATIONS

An International Search Report and a Written Opinion both dated Jun. 9, 2016, which issued during the prosecution of Applicant's PCT/IL2015/050978.
An Office Action dated Jun. 27, 2016 which issued during the prosecution of Australian Patent Application No. 2015202032.
An Office Action dated May 24, 2016 which issued during the prosecution of Chinese Patent Application No. 2013800124154.
European Search Report dated Jan. 20, 2016 which issued during the prosecution of Applicant's European App No. 13733888.
An Invitation to pay additional fees dated Dec. 23, 2015, which issued during the prosecution of Applicant's PCT/IL2015/050923.
An Office Action dated Jan. 5, 2016, which issued during the prosecution of Japanese Patent Application No. 2013-519213.
An Office Action dated Feb. 25, 2016, which issued during the prosecution of U.S. Appl. No. 13/809,562.
European Search Report dated Jun. 11, 2015 which issued during the prosecution of Applicant's European App No. 12826407.
Translation of Notice of Reasons for Refusal, dated Sep. 6, 2016, issued in corresponding JP Application No. 2014-526597, 5 pages in English.
European Search Report dated May 11, 2017, which issued during the prosecution of Applicant's European App No. 11806391.6.
Notice of Allowance together with the English translation dated Nov. 1, 2017, which issued during the prosecution of Korean Patent Application No. 10-2013-7003093.
An International Search Report and a Written Opinion both dated Aug. 23, 2017, which issued during the prosecution of Applicant's PCT/IL2016/051379.
An International Search Report and a Written Opinion both dated May 24, 2018, which issued during the prosecution of Applicant's PCT/IL2018/050180.
An Office Action dated May 8, 2018, which issued during the prosecution of U.S. Appl. No. 15/665,838.
An Office Action dated Feb. 18, 2016 which issued during the prosecution of Australian Patent Application No. 2012298197.
An International Search Report and a Written Opinion both dated Mar. 10, 2016, which issued during the prosecution of Applicant's PCT/IL2015/050923.

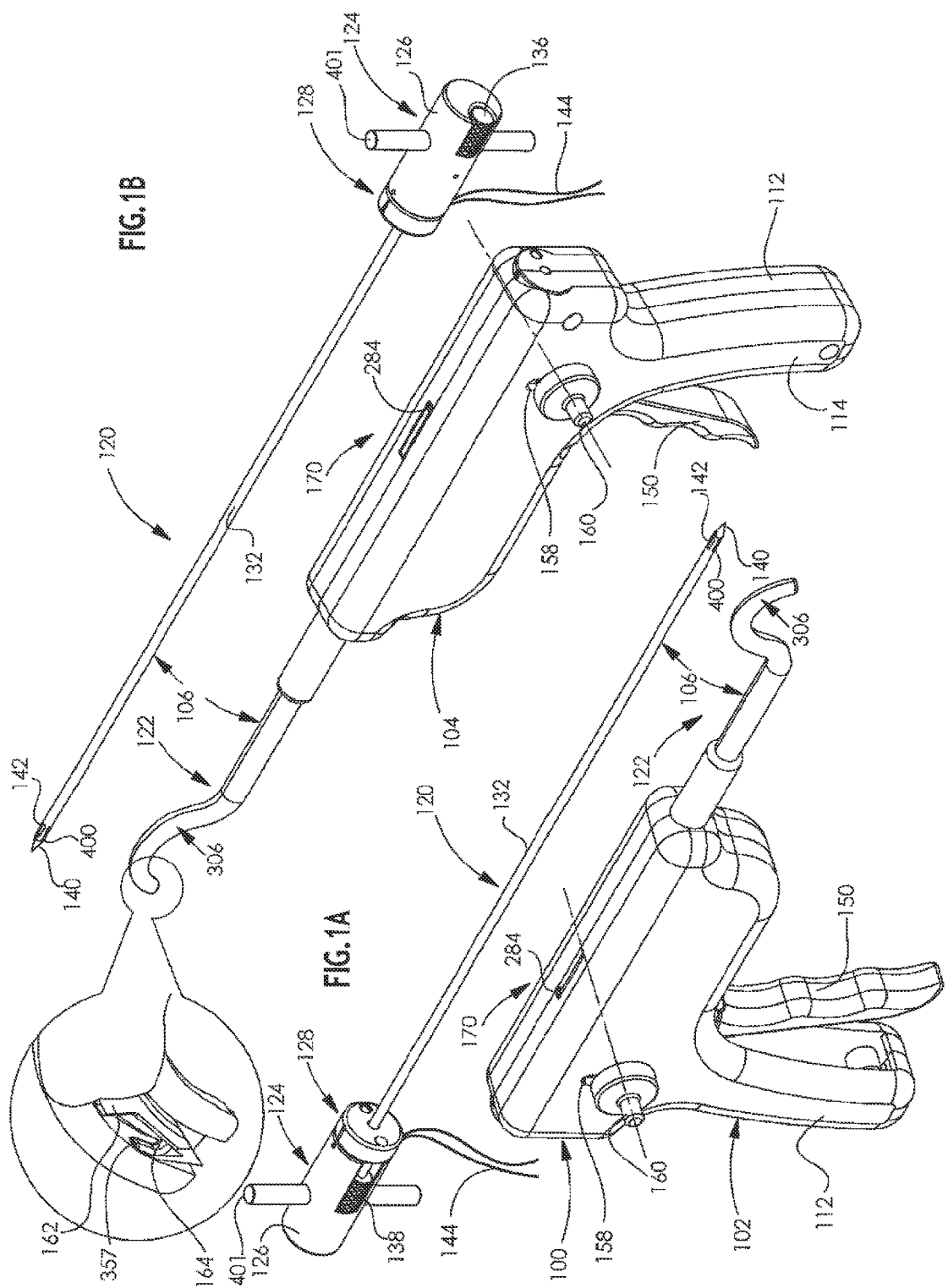

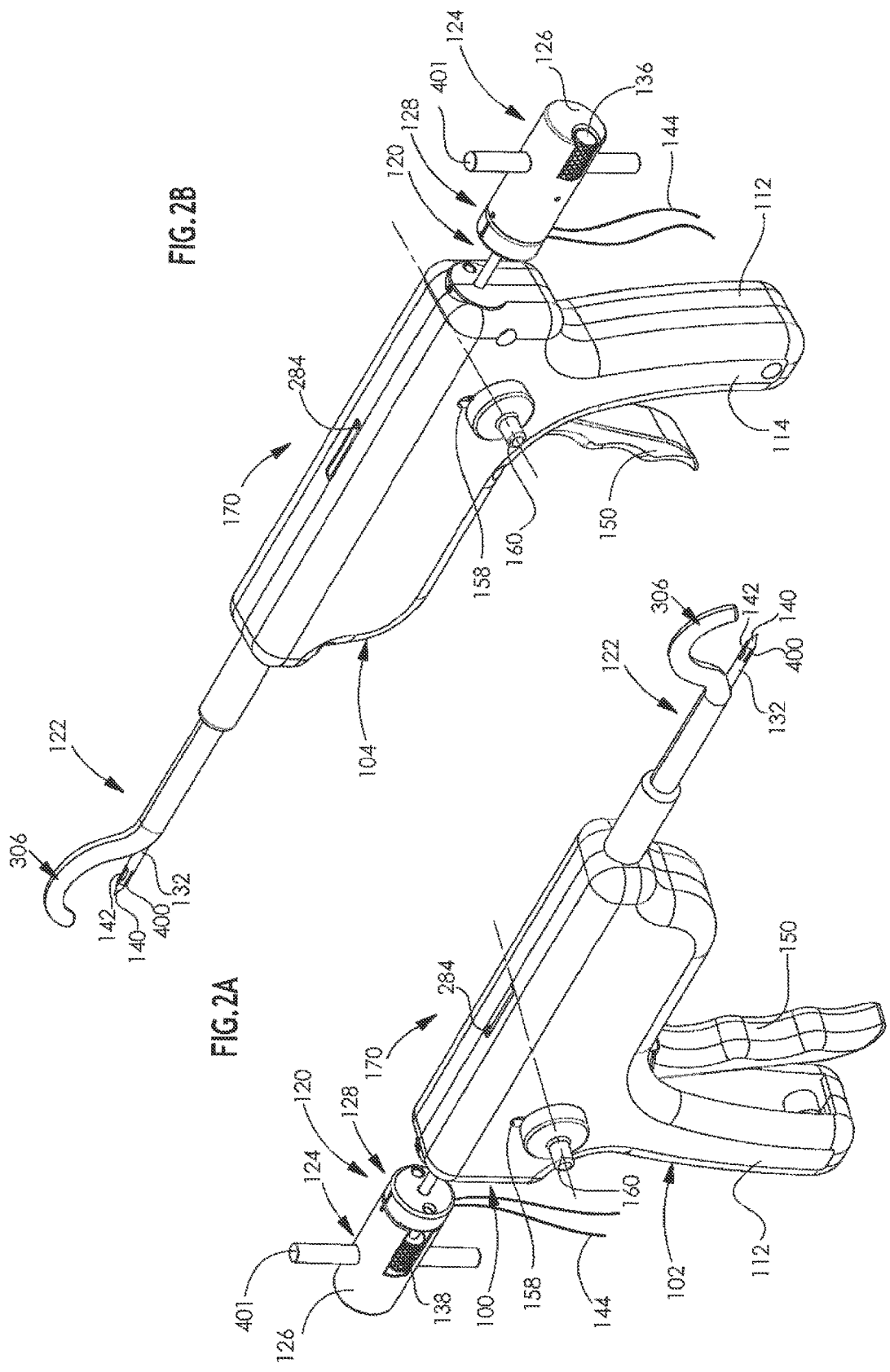

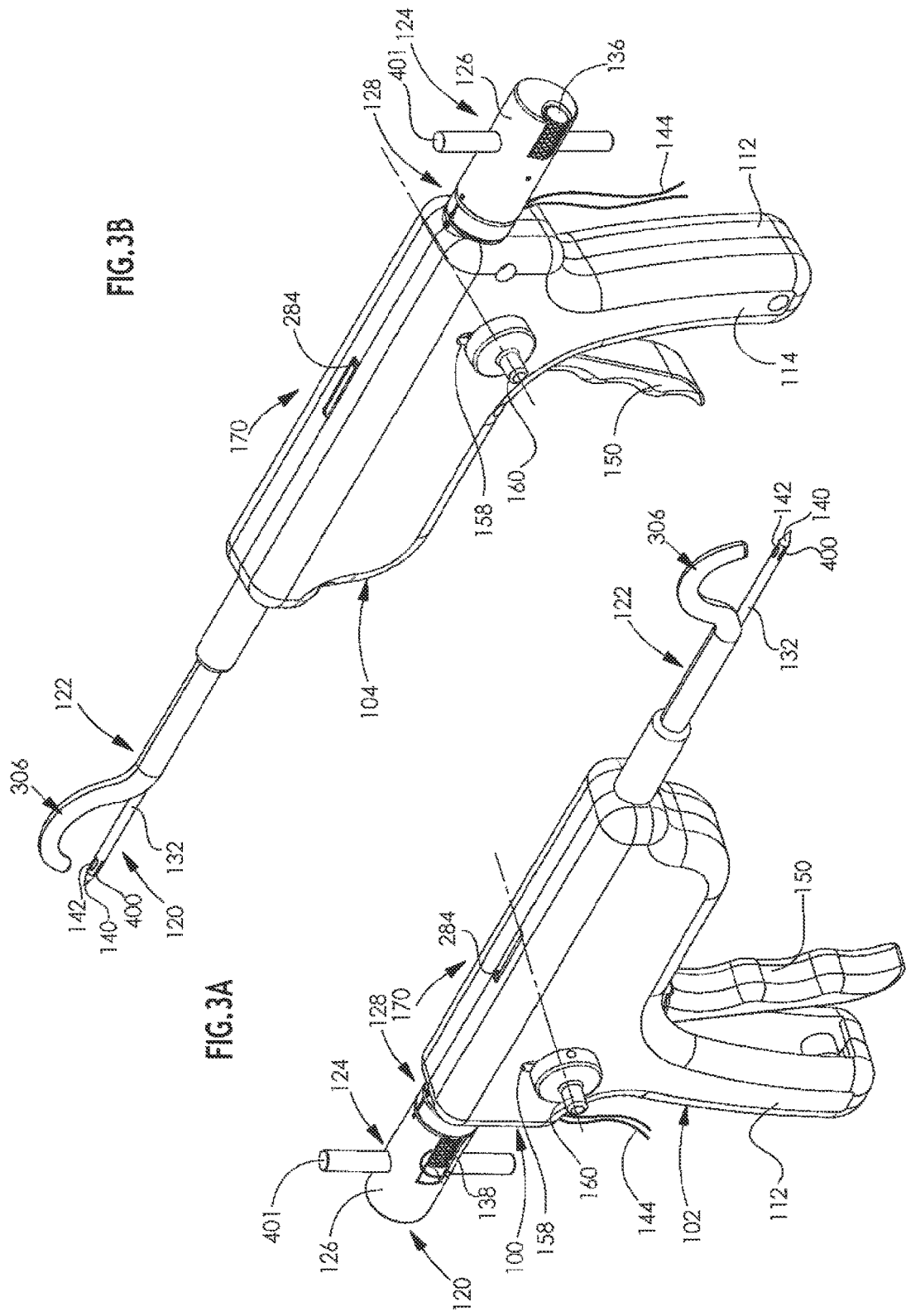

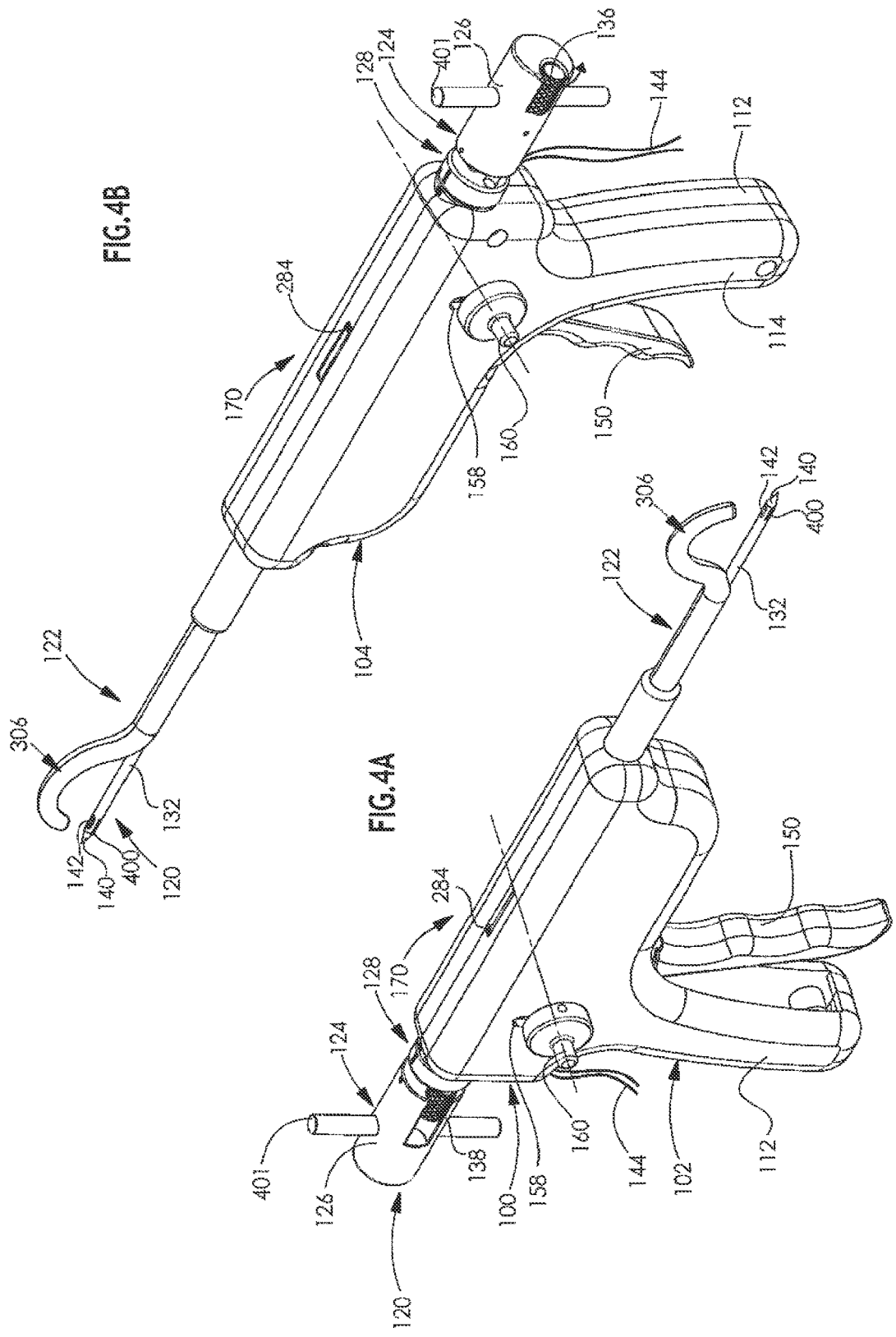

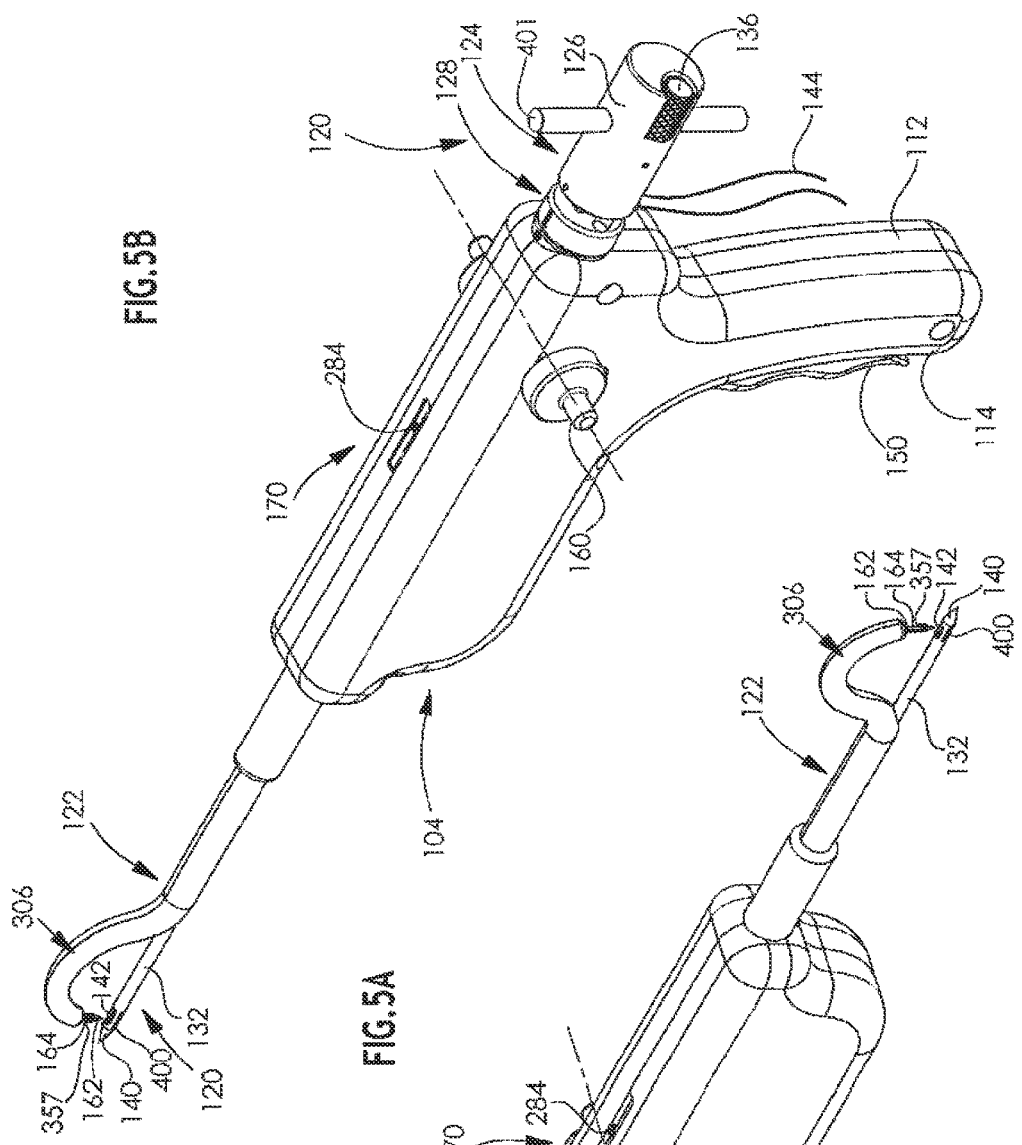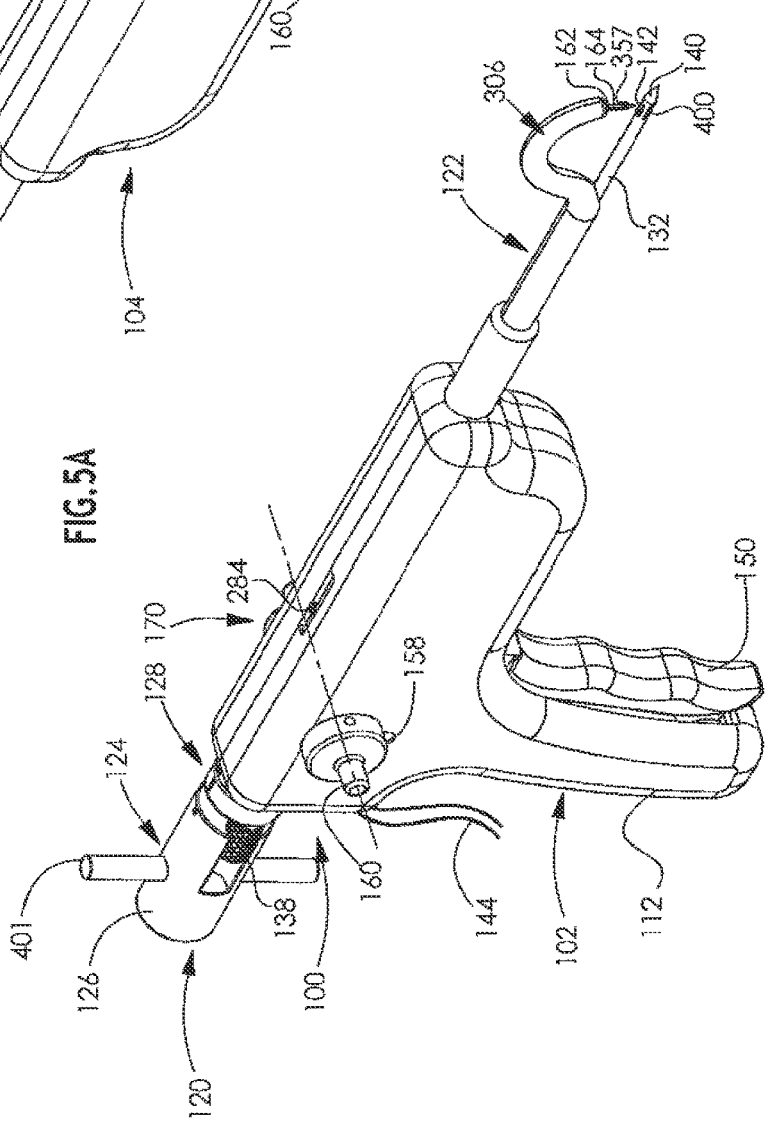

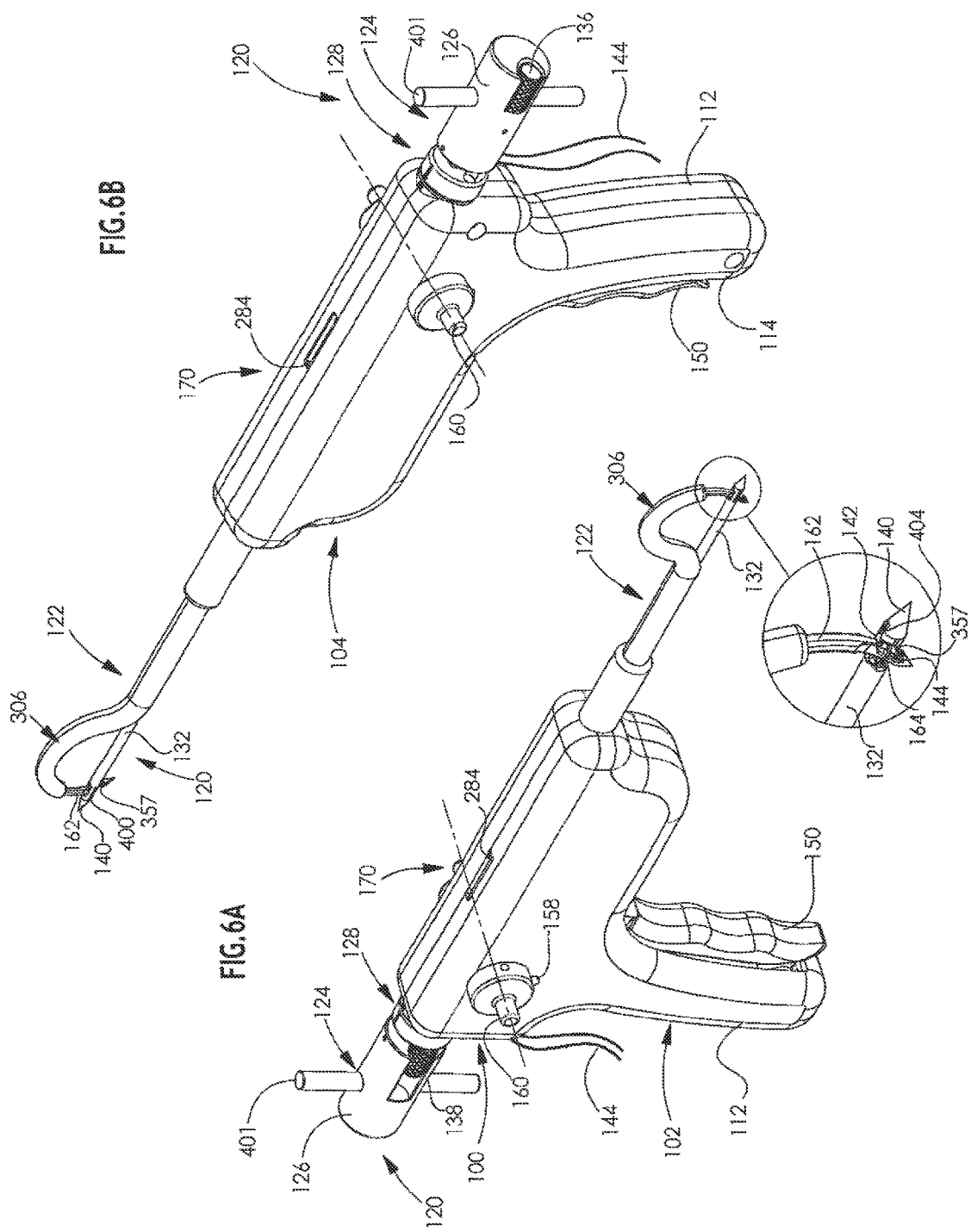

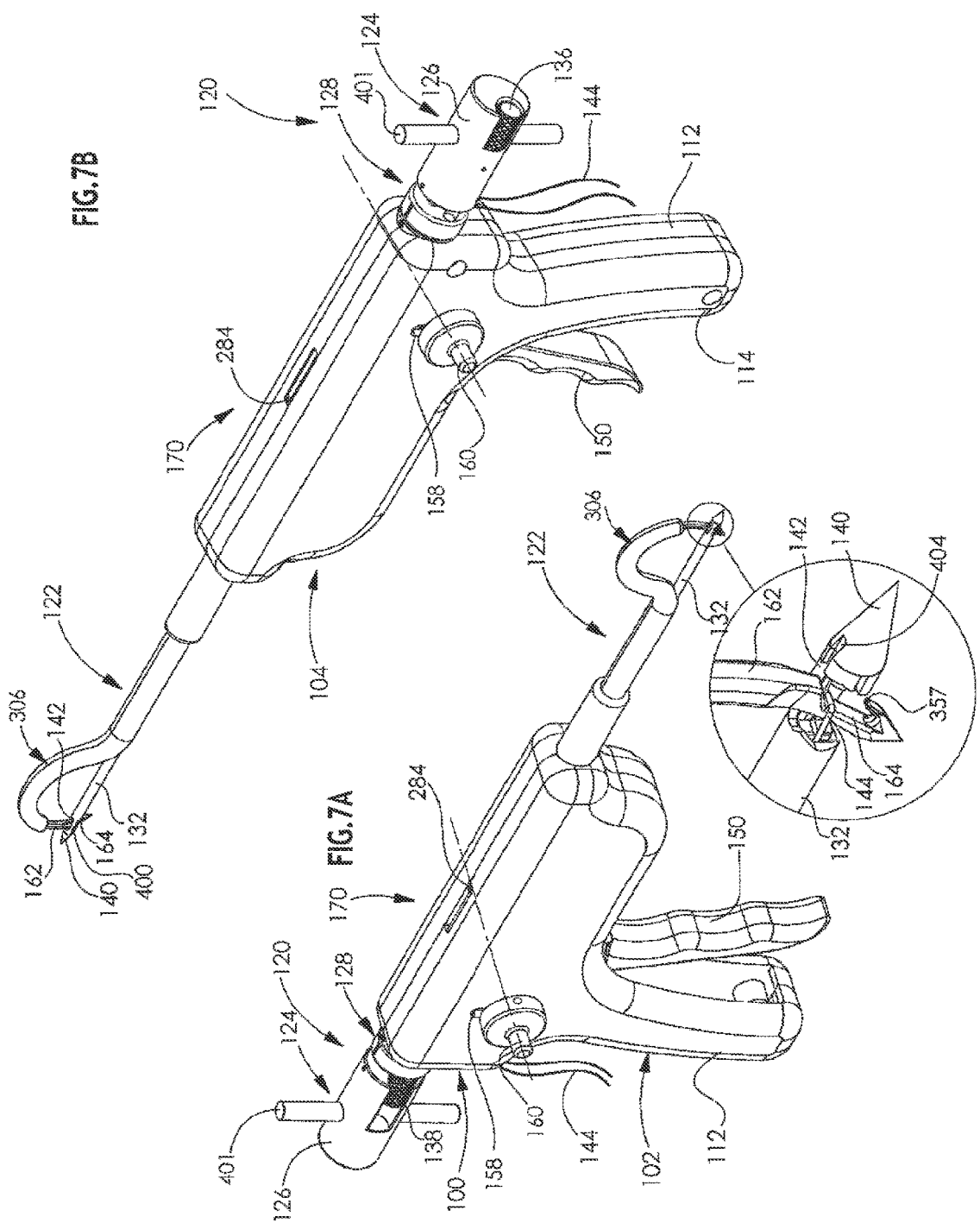

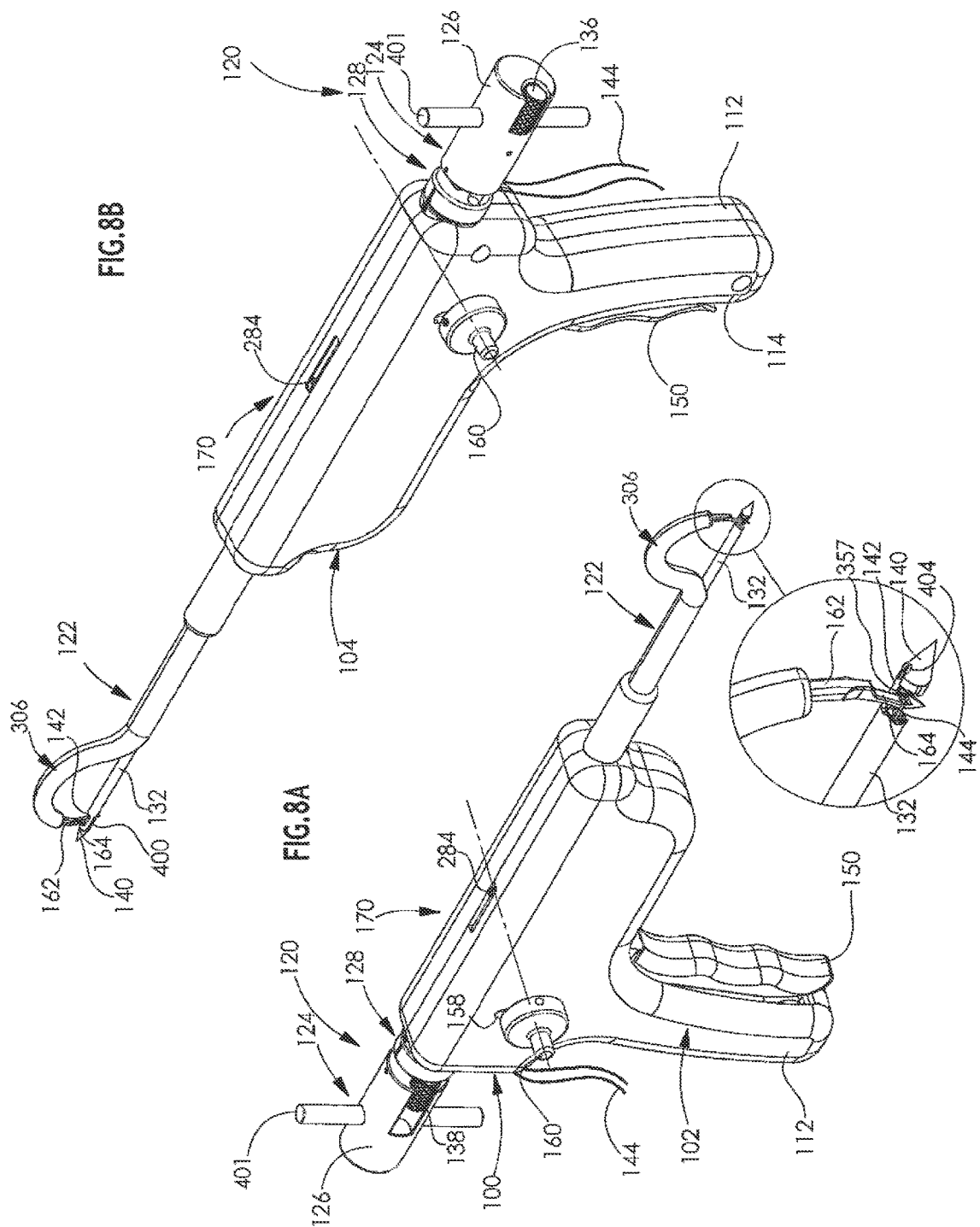

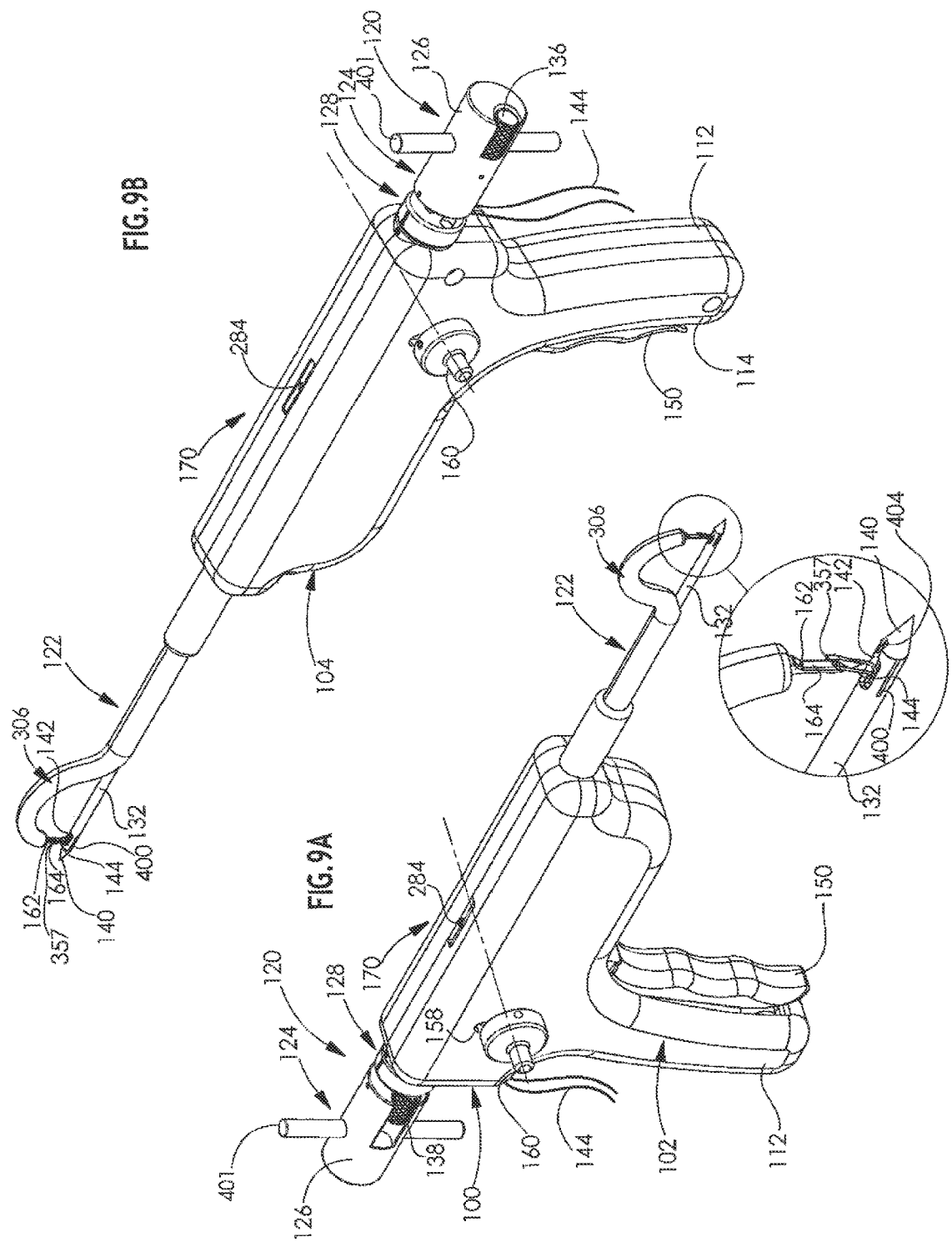

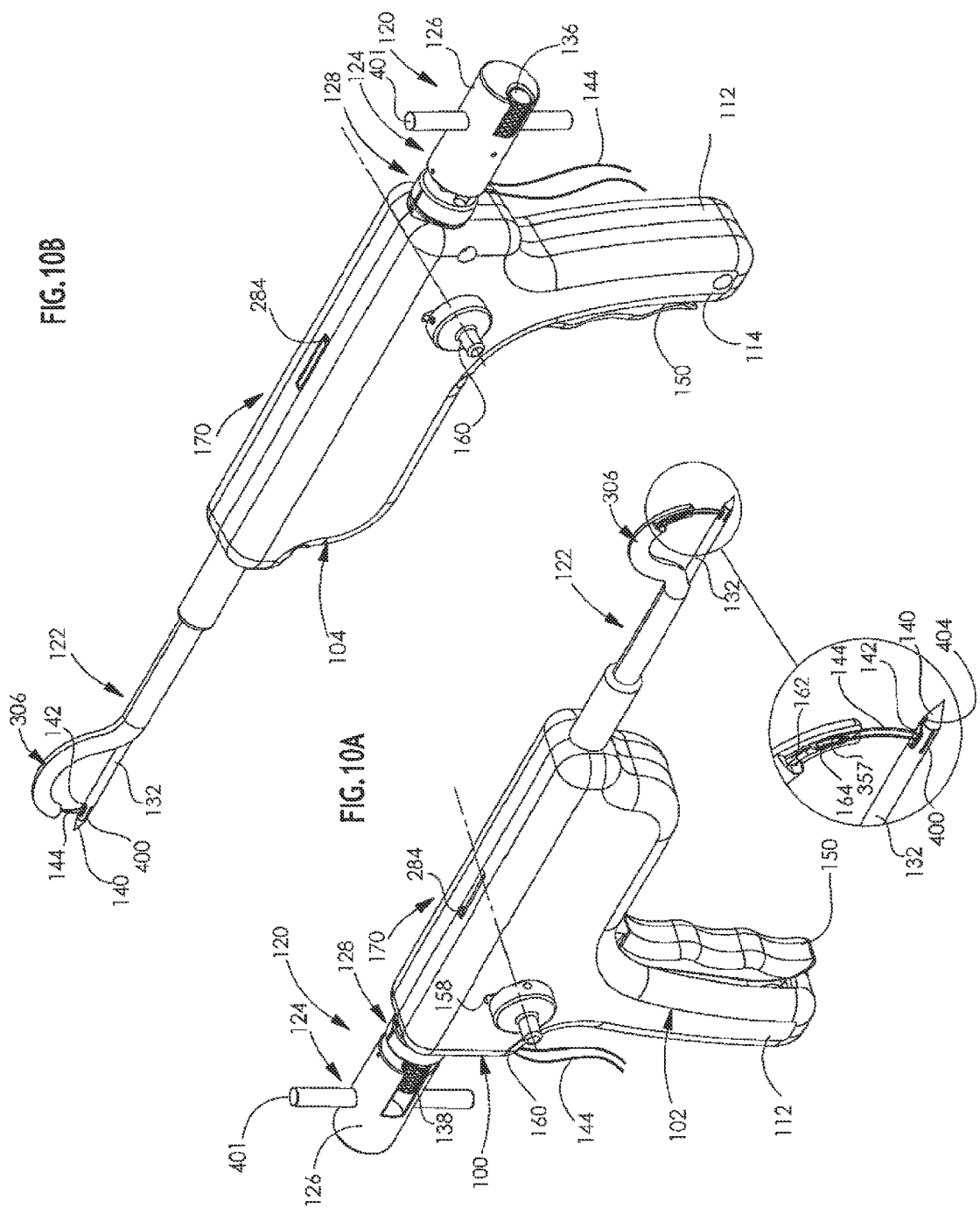

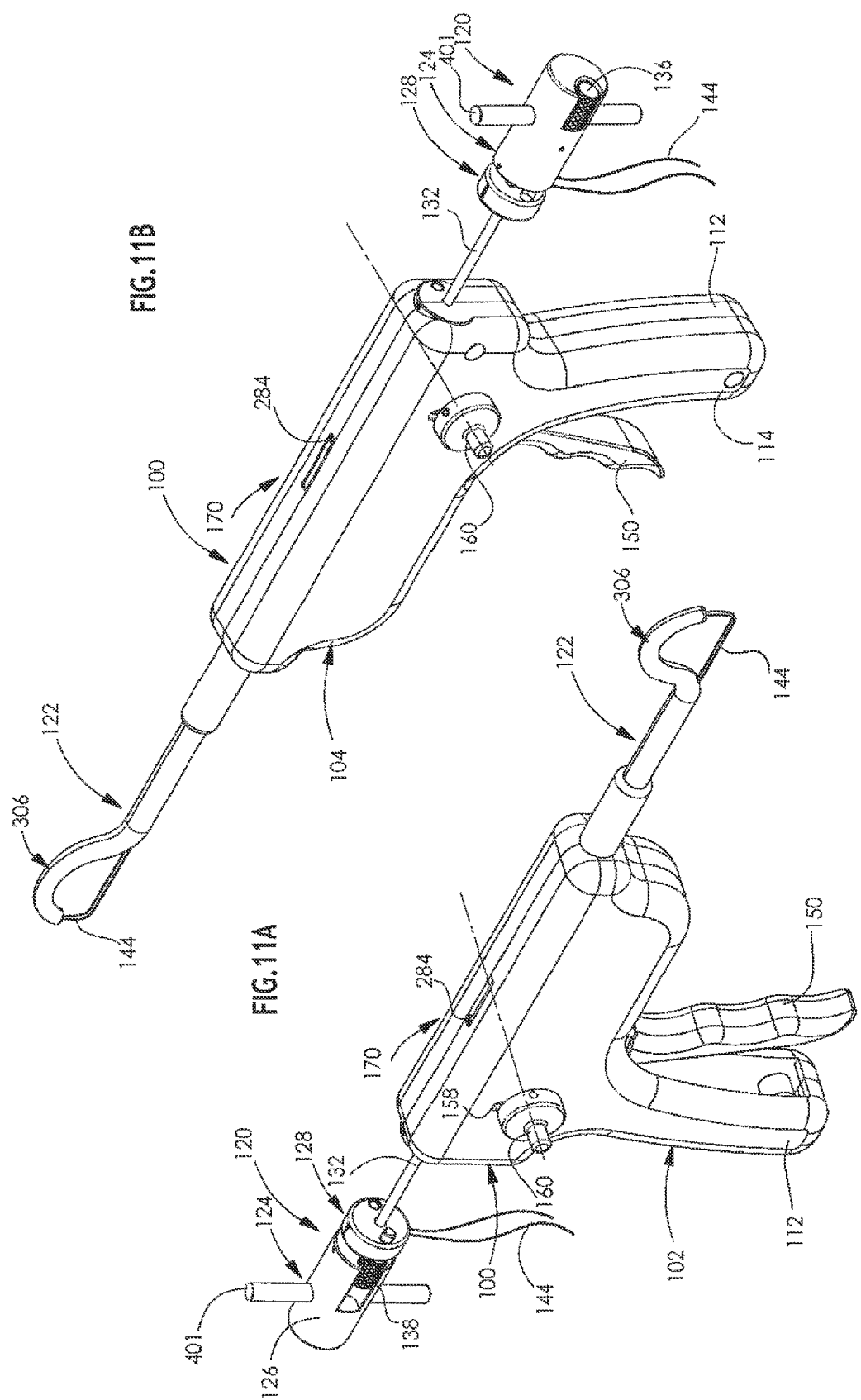

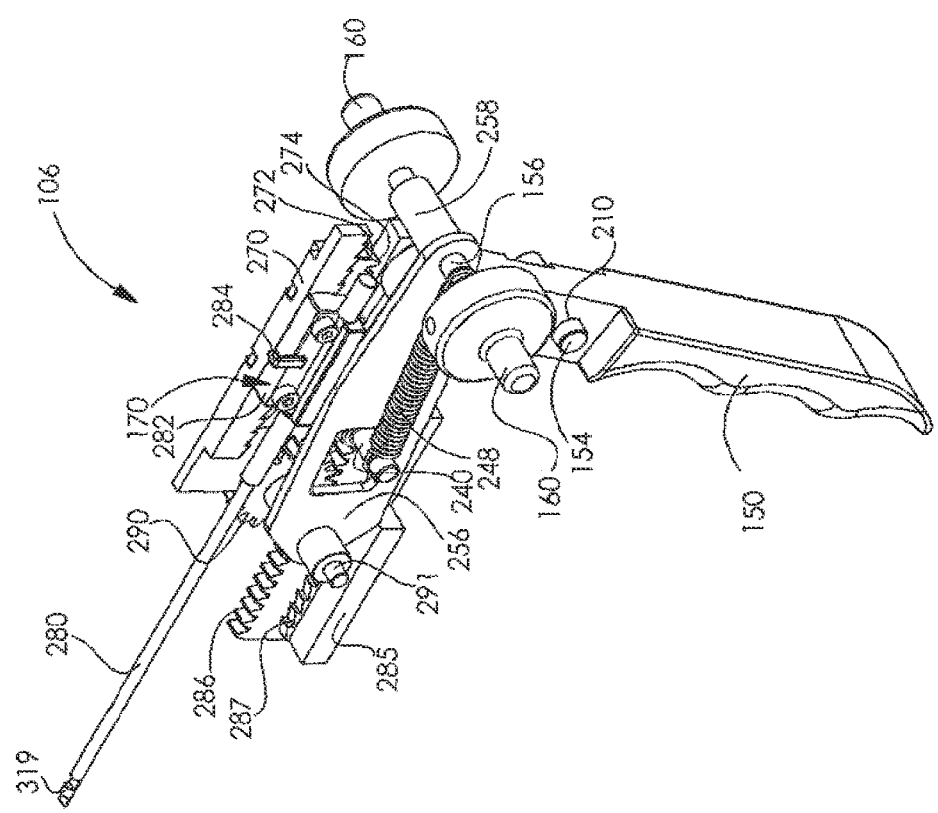

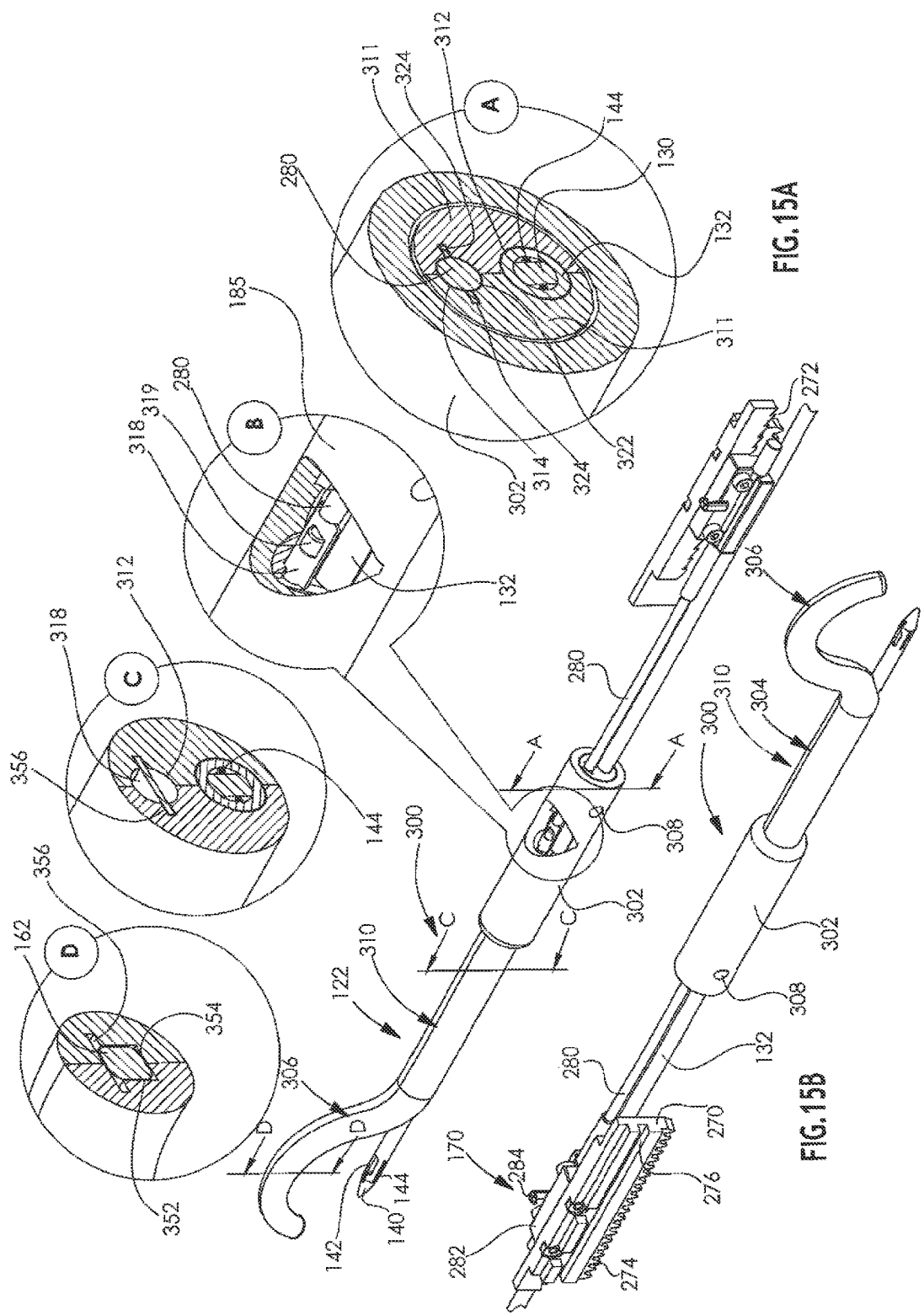

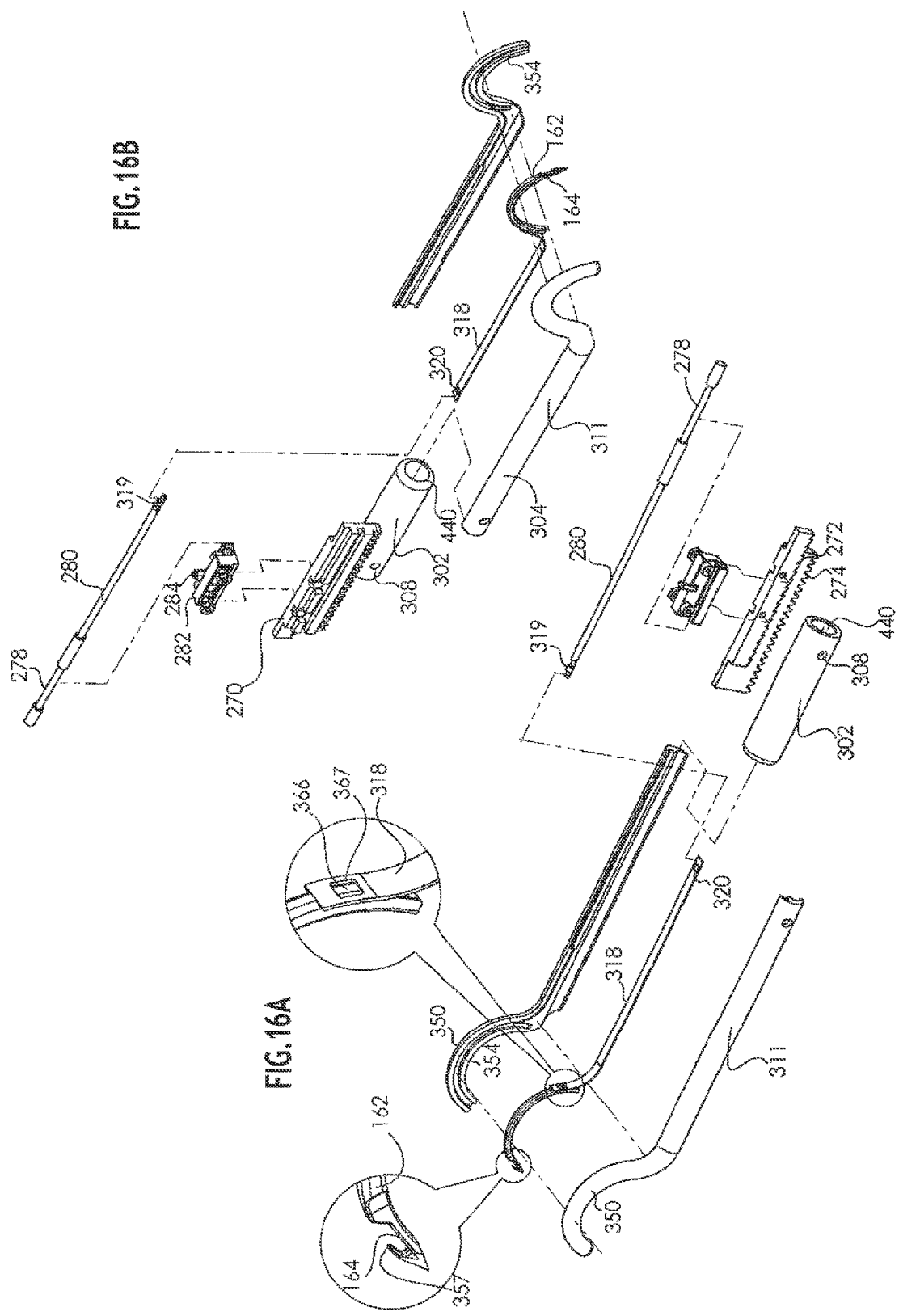

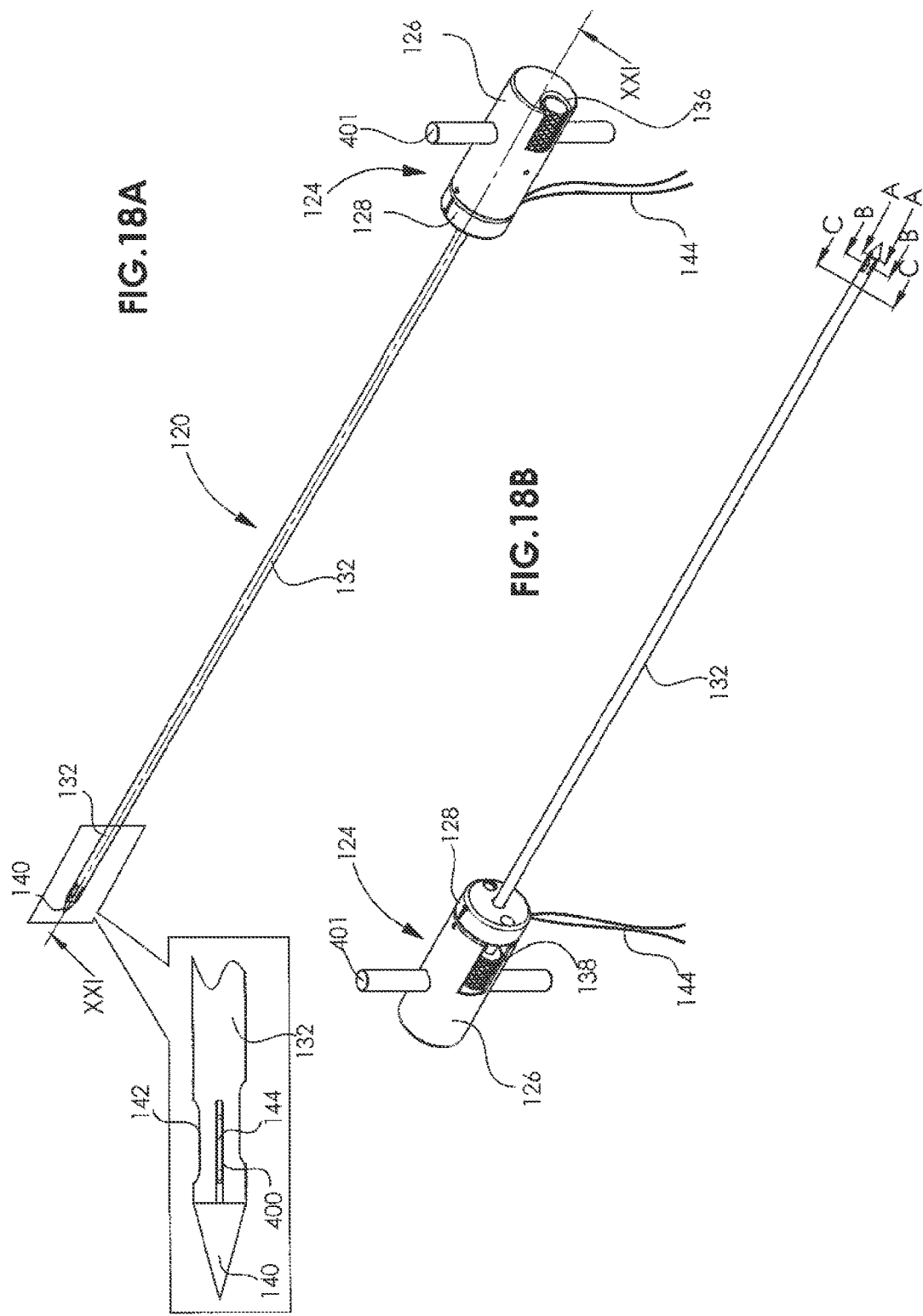

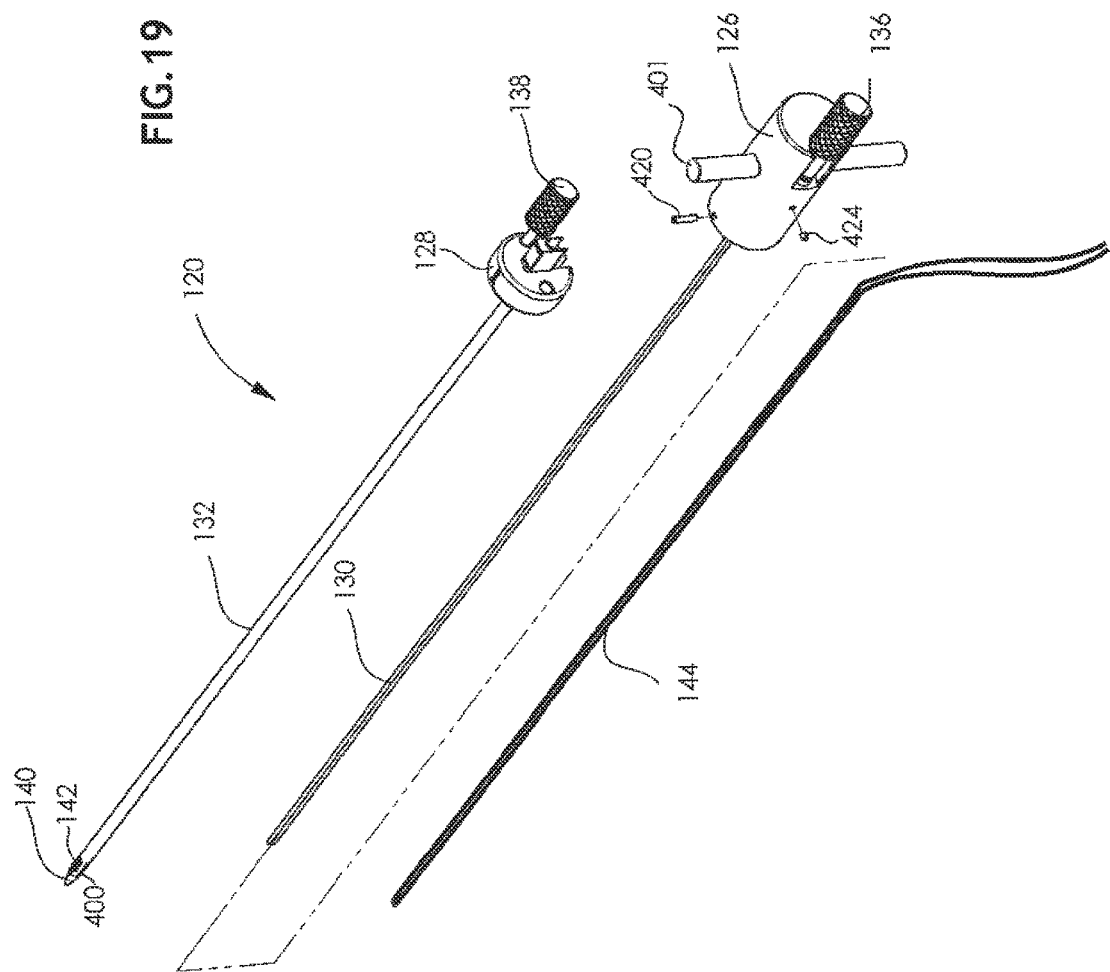

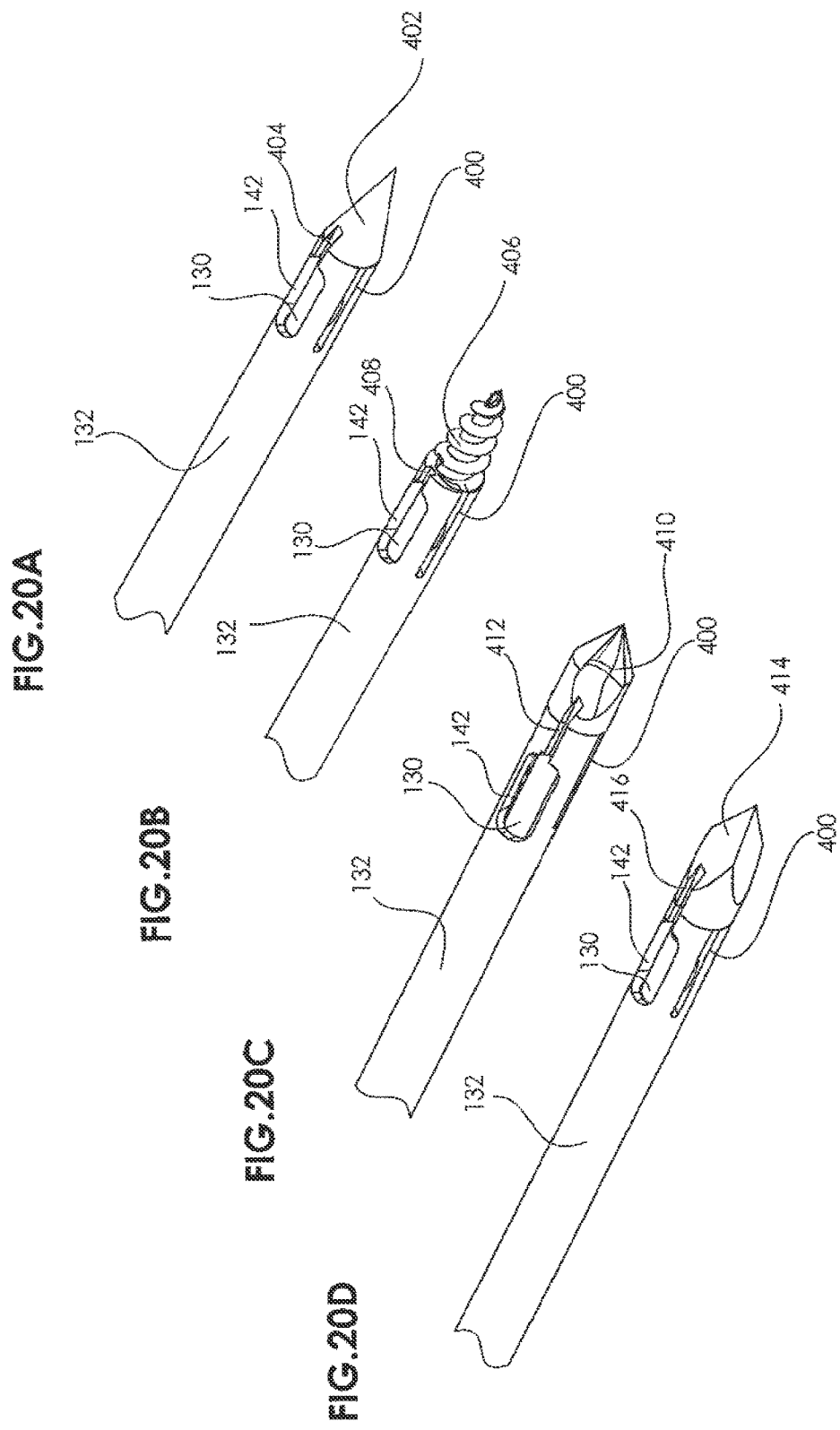

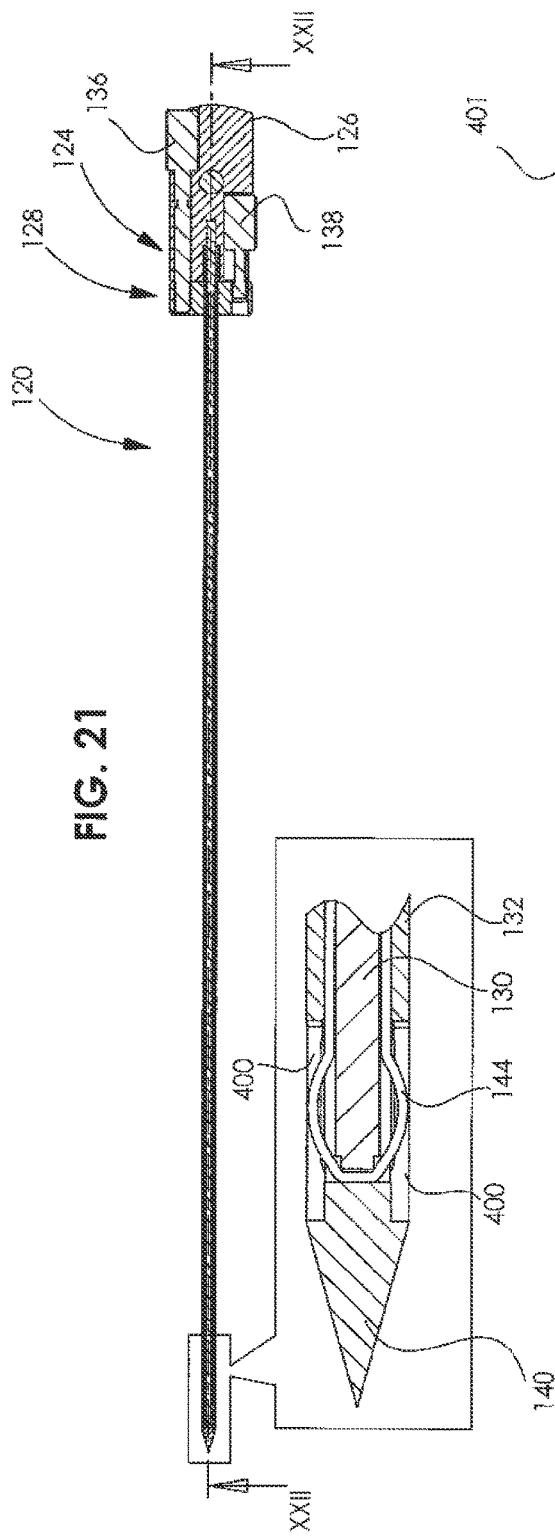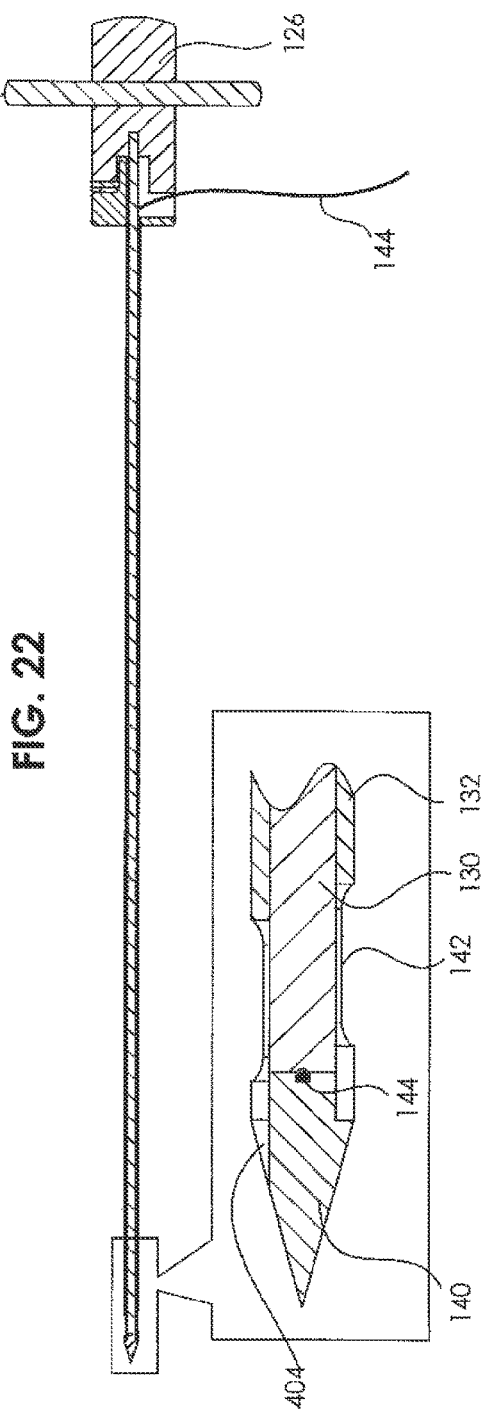

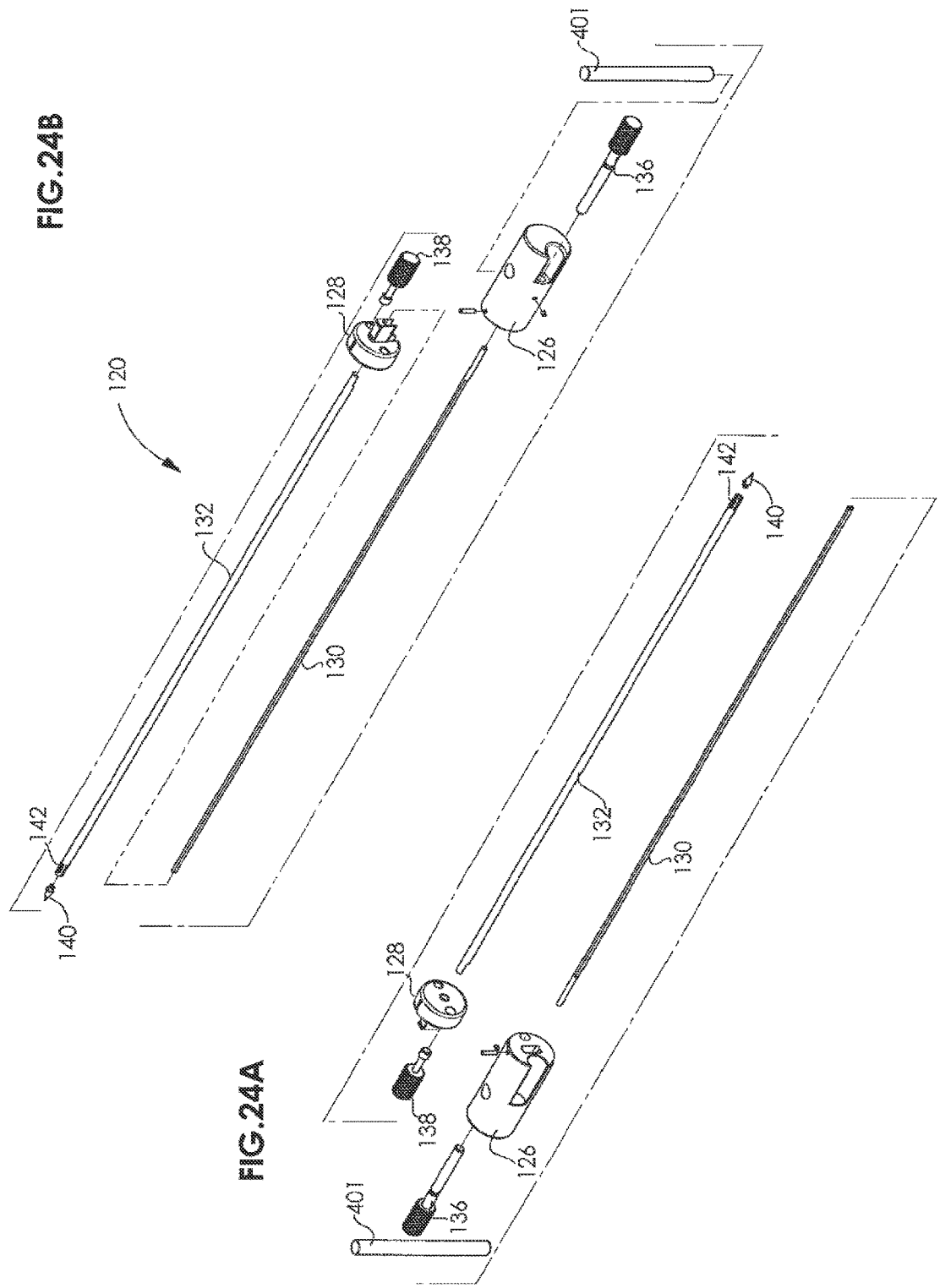

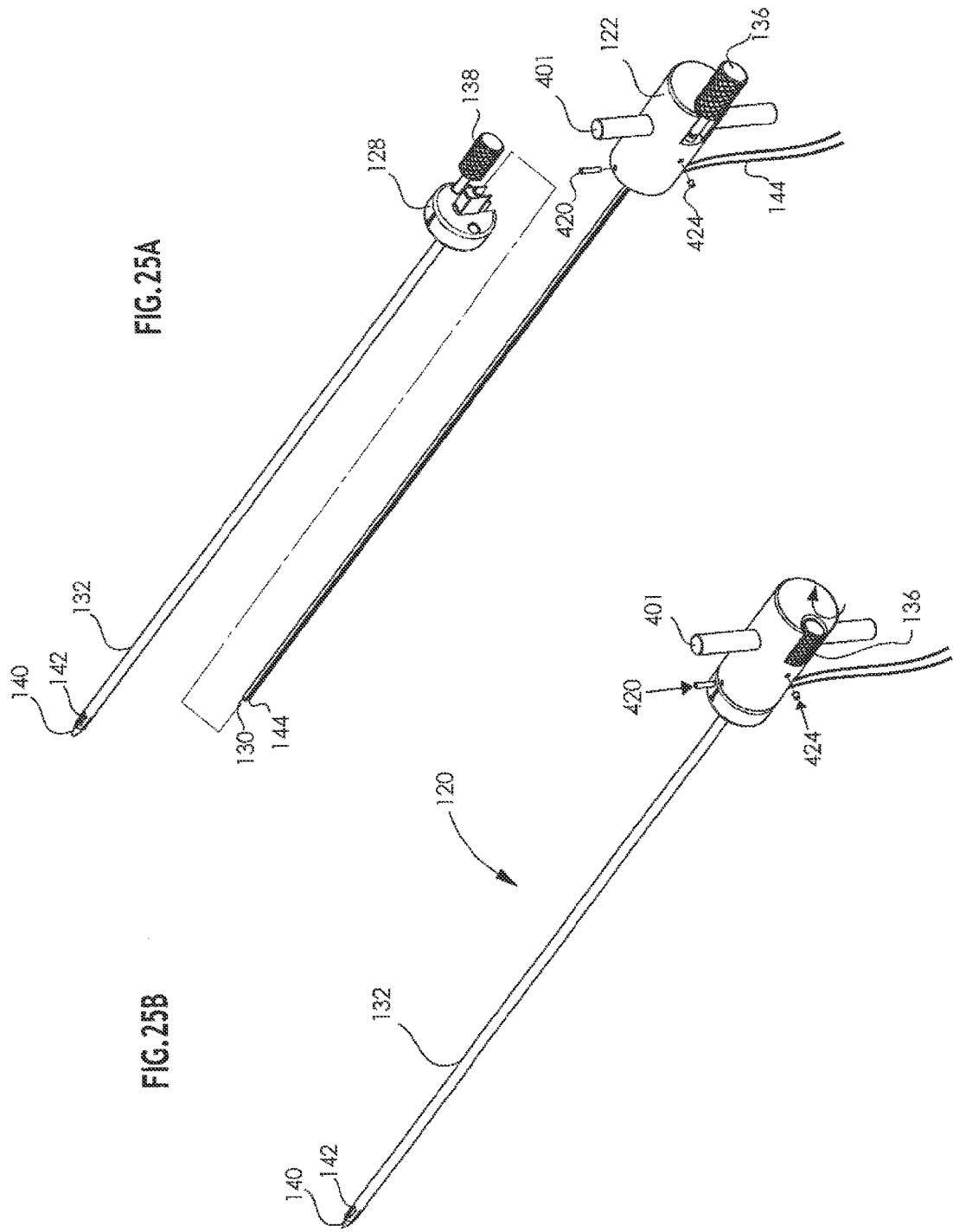

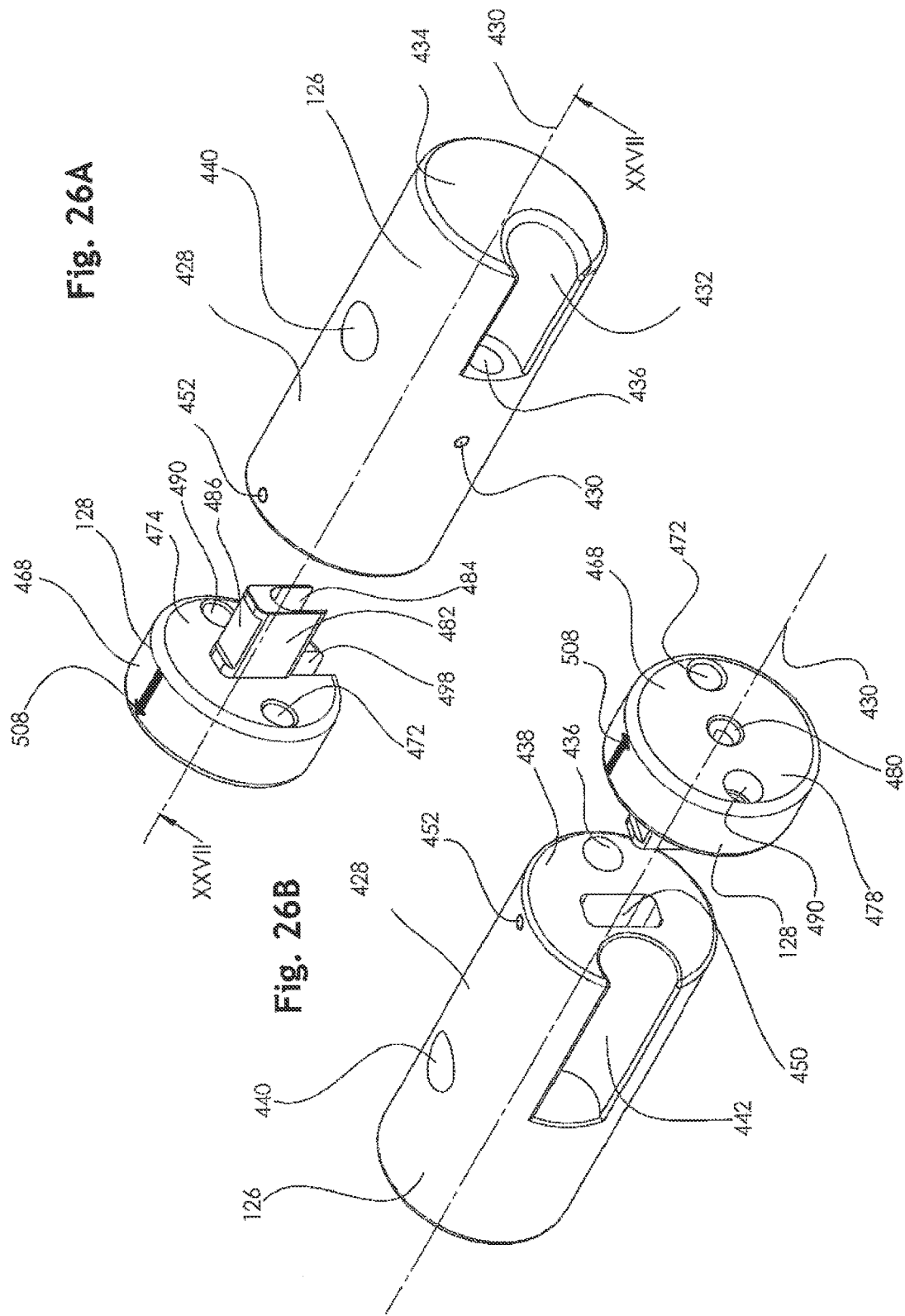

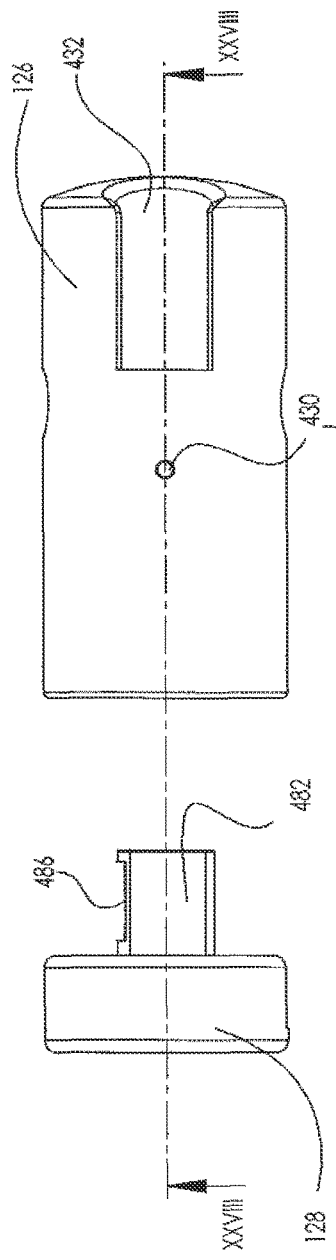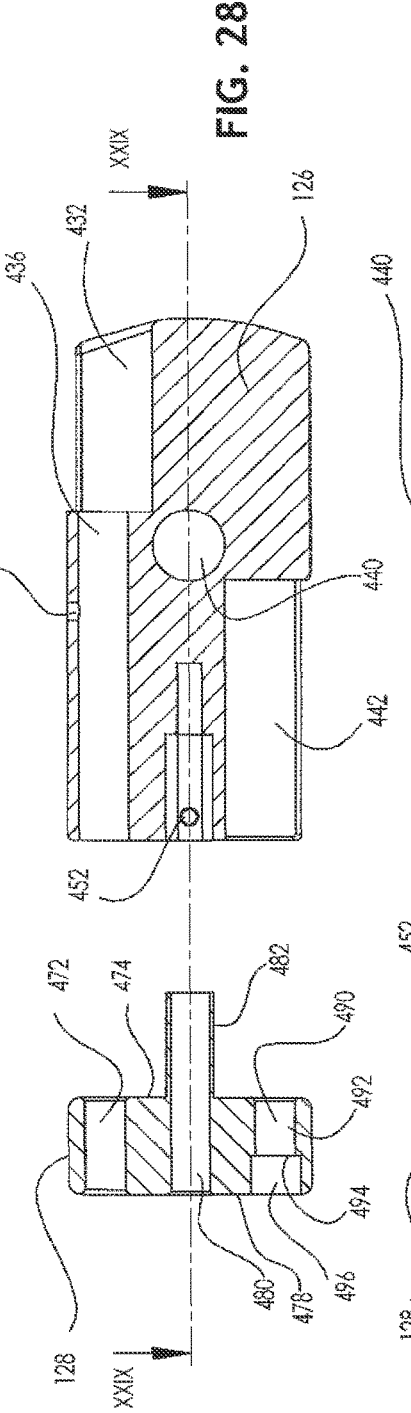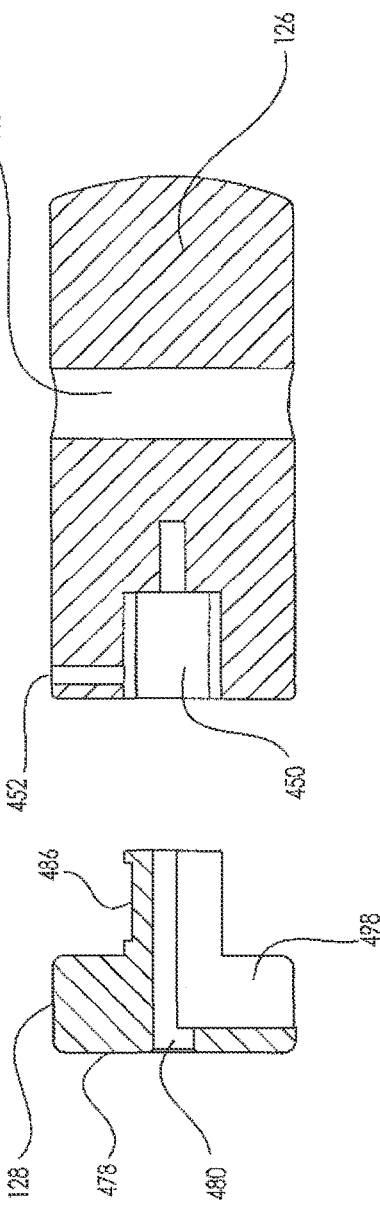

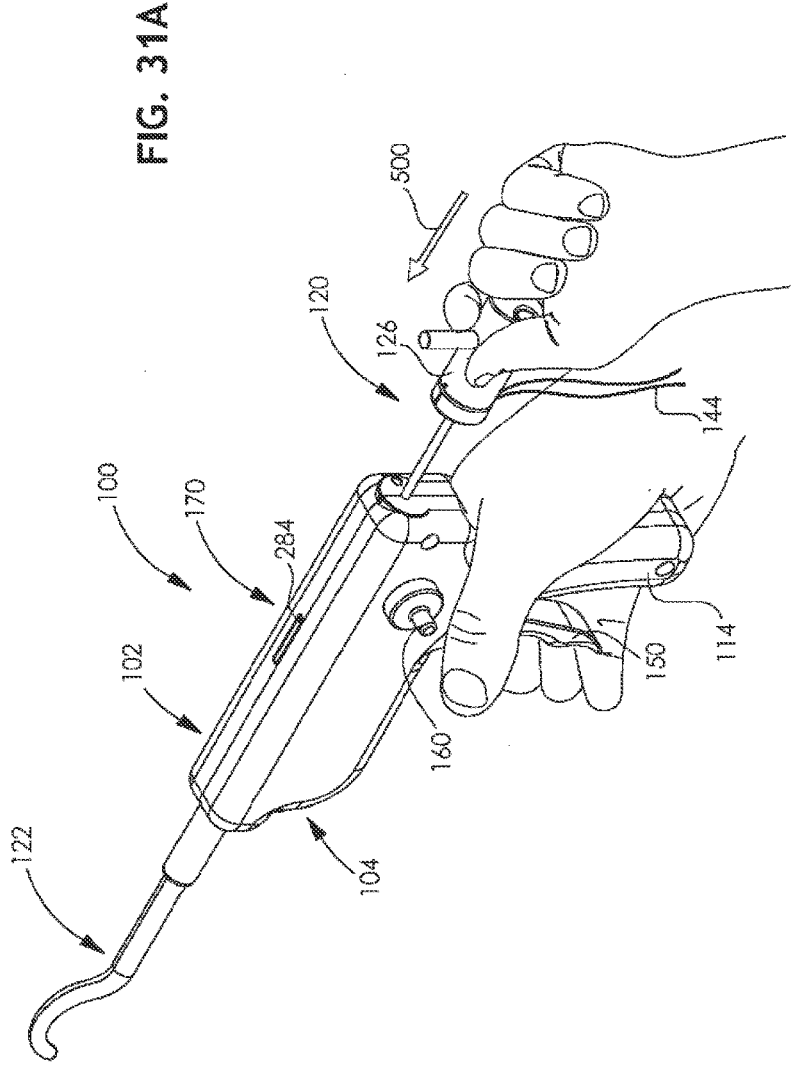

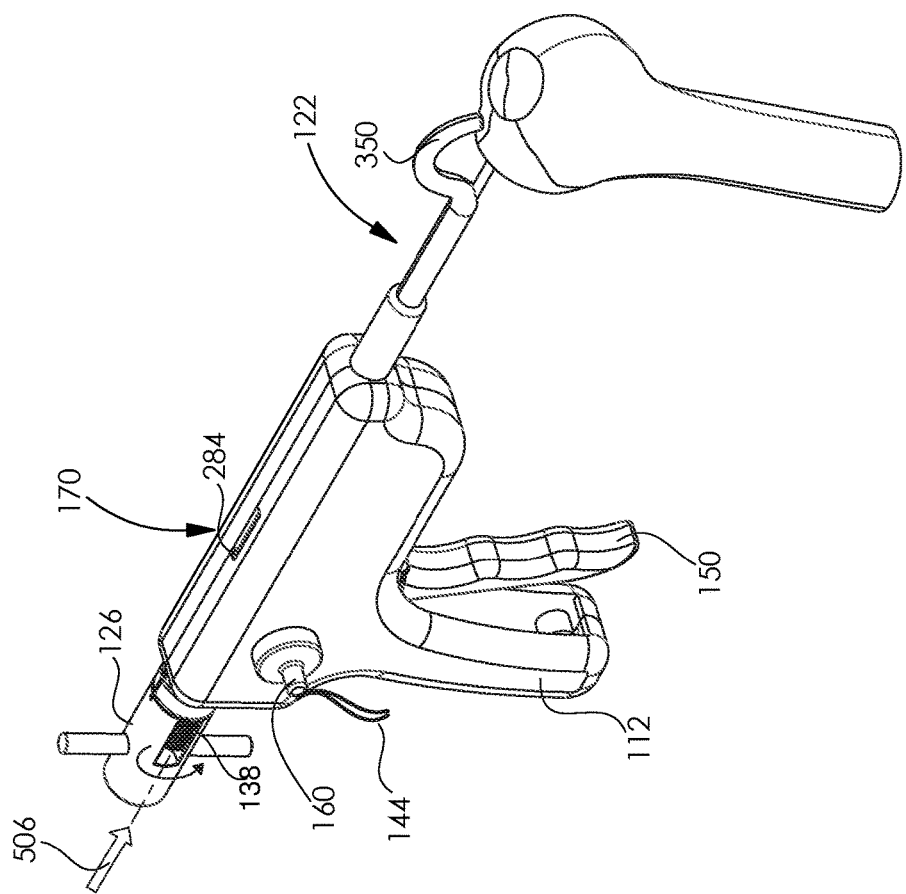

ARTHROSCOPIC SURGICAL DEVICE

REFERENCE TO RELATED APPLICATIONS

Reference is made to the following U.S. Provisional patent applications which are believed to be related to the present application, the contents of which are hereby incorporated by reference herein and priority of which is hereby claimed under 37 CFR 1.78(a)(4) and (5)(i):

U.S. Provisional Patent Application Ser. No. 61/584,267, entitled "Circular Bone Tunneling Device" and filed Jan. 8, 2012;

U.S. Provisional Patent Application Ser. No. 61/636,751, entitled "Circular Bone Tunneling Device Employing a Stabilizing Element" and filed Apr. 23, 2012; and U.S. Provisional Patent Application Ser. No. 61/714,813, entitled "Arthroscopic Surgical Device" and filed Oct. 17, 2012.

Reference is also made to the following PCT Patent Applications which are believed to be related to the present application, the contents of which are hereby incorporated by reference herein and priority of which is hereby claimed under 37 CFR 1.78(a)(1) and (2)(i):

PCT Patent Application No. PCT/IL2012/000318, entitled "Arthroscopic Surgical Device" and filed Aug. 23, 2012, the contents of which are hereby incorporated by reference herein; and PCT Patent Application No. PCT/IL2012/000319, entitled "Circular Bone Tunneling Device Employing a Stabilizing Element" and filed Aug. 23, 2012, the contents of which are hereby incorporated by reference herein.

Reference is also made to:

Published PCT Patent Application No. WO 2012/007941, entitled "Circular Bone Tunneling Device" and filed Jul. 11, 2011, the contents of which are hereby incorporated by reference herein; and U.S. Provisional Patent Application Ser. No. 61/526,717, entitled "Circular Bone Tunneling Device" and filed Aug. 24, 2011, the contents of which are hereby incorporated by reference herein.

FIELD OF THE INVENTION

The present invention relates generally to arthroscopic surgical devices and more particularly to arthroscopic bone tunneling devices.

BACKGROUND OF THE INVENTION

Various types of arthroscopic surgical instruments are known for various applications including orthopedic surgery.

SUMMARY OF THE INVENTION

The present invention seeks to provide an improved arthroscopic bone tunneling and suturing device.

There is thus provided in accordance with a preferred embodiment of the present invention an arthroscopic bone tunneling and suturing device including a bone-engaging needle driving assembly including a bone-engaging needle and being adapted for arthroscopic insertion into engagement with a patient's bone at a first bone location through an arthroscopic incision and for driving the needle forwardly along a generally arcuate tunneling path through the bone at least to a second bone location and a bone-engaging pin driving assembly arranged for operative engagement with the bone-engaging needle driving assembly and being adapted for arthroscopic insertion into engagement with a patient's bone at a third bone location through the arthroscopic incision.

Preferably, the bone-engaging pin driving assembly is adapted for mounting a suture thereon and positioning the suture so that it can be engaged by the needle at the second bone location. Additionally, the bone-engaging needle driving assembly is also adapted for retracting the needle, in engagement with the suture, back along the arcuate tunneling path through the bone from the second bone location.

In accordance with a preferred embodiment of the present invention the bone-engaging pin driving assembly includes at least one bone tunneling pin which is operative to tunnel through the bone along a generally linear tunneling path from the third location to the second location at which the generally linear tunneling path intersects the generally arcuate tunneling path, thereby positioning the suture so that it can be engaged by the needle at the second bone location.

Preferably, the bone-engaging pin driving assembly is separate from the bone-engaging needle driving assembly and is selectably engageable therewith and disengageable therefrom.

In accordance with a preferred embodiment of the present invention the bone engaging pin driving assembly includes an inner pin and an outer, hollow pin in which the inner pin is slidably disposed. Additionally, the outer hollow pin is formed with a pointed tip and with a throughgoing aperture.

Preferably, a suture extends between the inner pin and the outer pin, the suture being looped about the inner pin interiorly of the outer pin so as to be engageable by the needle through the throughgoing aperture. Additionally or alternatively, the bone-engaging pin driving assembly also includes a base assembly including a forward portion and a rearward portion, the inner pin being coupled to the rearward portion and the outer pin being coupled to the forward portion.

In accordance with preferred embodiment of the present invention the outer hollow pin is also formed with a throughgoing side wall slot for accommodating part of the suture. Additionally, the suture is wound around a forward end of the inner pin and between the forward end of the inner pin and the pointed tip and extends between the inner pin and the outer pin and partially lies in the throughgoing slot on both sides of the inner pin.

Preferably, the base assembly selectably lockable to a housing which encloses part of the bone-engaging needle driving assembly. Additionally or alternatively, the forward portion and the rearward portion of the base assembly are selectably lockable to each other and axially slidable with respect to each other, thereby to provide limited retractability of the inner pin with respect to the outer pin.

In accordance with a preferred embodiment of the present invention the bone-engaging needle driving assembly includes a flexible needle driving strip which drives the bone engaging needle along the arcuate tunneling path through the bone.

There is also provided in accordance with another preferred embodiment of the present invention a method for tunneling through a bone during arthroscopic surgery, the method including providing a bone-engaging pin driving assembly and a bone-engaging needle driving assembly, the bone-engaging needle driving assembly including a bone-engaging needle adapted for arthroscopic insertion into engagement with a patient's bone at a first bone location through an arthroscopic incision and for being driven forwardly along a generally arcuate tunneling path through the bone at least to a second bone location, operatively engaging the bone-engaging pin driving assembly with the bone-engaging needle driving assembly, inserting the bone-engaging needle driving assembly through the arthroscopic incision into engagement with the bone at the first bone location, inserting the bone-engaging pin driving assembly through the arthroscopic incision into engagement with a patient's bone at a third bone location, tunneling through the bone with the bone-engaging pin driving assembly along a generally linear tunneling path from the third bone location to the second bone location and driving the needle, along the generally arcuate tunneling path from the first bone location at least to the second bone location, with the bone-engaging needle driving assembly, thereby tunneling through the bone with the bone-engaging needle along the generally arcuate tunneling path from the first bone location at least to the second bone location.

Preferably, the method for tunneling through a bone during arthroscopic surgery also includes mounting a suture on the bone-engaging pin driving assembly prior to the operatively engaging the bone-engaging pin driving assembly with the bone-engaging needle driving assembly and subsequent to the driving, engaging the suture with the needle at the second bone location.

In accordance with a preferred embodiment of the present invention the method for tunneling through a bone during arthroscopic surgery also includes subsequent to the engaging, retracting the needle, in engagement with the suture, along the generally arcuate tunneling path.

Preferably, the method for tunneling through a bone during arthroscopic surgery further includes, subsequent to the retracting the needle, retracting the bone-engaging pin driving assembly from engagement with the bone.

In accordance with a preferred embodiment of the present invention the method for tunneling through a bone during arthroscopic surgery also includes, subsequent to the retracting the bone-engaging pin driving assembly, partially re-extending the needle and disengaging the suture from the needle.

Preferably, the operatively engaging also includes aligning the bone-engaging pin driving assembly with the bone-engaging needle driving assembly so that the needle can engage the suture at the second bone location and subsequently axially and rotationally locking the bone-engaging pin driving assembly to the bone-engaging needle driving assembly.

BRIEF DESCRIPTION OF THE DRAWINGS

The present invention will be understood and appreciated from the following detailed description, taken in conjunction with the drawings in which:

FIGS. 1A & 1B are simplified pictorial illustrations of an arthroscopic surgical device constructed and operative in accordance with a preferred embodiment of the present invention, showing opposite views in a first operative orientation;

FIGS. 2A & 2B are simplified pictorial illustrations of an arthroscopic surgical device constructed and operative in accordance with a preferred embodiment the present invention, showing opposite views in a second operative orientation;

FIGS. 3A & 3B are simplified pictorial illustrations of an arthroscopic surgical device constructed and operative in accordance with a preferred embodiment of the present invention, showing opposite views in a third operative orientation;

FIGS. 4A & 4B are simplified pictorial illustrations of an arthroscopic surgical device constructed and operative in accordance with a preferred embodiment of the present invention, showing opposite views in a fourth operative orientation;

FIGS. 5A & 5B are simplified pictorial illustrations of an arthroscopic surgical device constructed and operative in accordance with a preferred embodiment of the present invention, showing opposite views in a fifth operative orientation;

FIGS. 6A & 6B are simplified pictorial illustrations of an arthroscopic surgical device constructed and operative in accordance with a preferred embodiment of the present invention, showing opposite views in a sixth operative orientation;

FIGS. 7A & 7B are simplified pictorial illustrations of an arthroscopic surgical device constructed and operative in accordance with a preferred embodiment of the present invention, showing opposite views in a seventh operative orientation;

FIGS. 8A & 8B are simplified pictorial illustrations of an arthroscopic surgical device constructed and operative in accordance with a preferred embodiment of the present invention, showing opposite views in an eighth operative orientation;

FIGS. 9A & 9B are simplified pictorial illustrations of an arthroscopic surgical device constructed and operative in accordance with a preferred embodiment of the present invention, showing opposite views in a ninth operative orientation;

FIGS. 10A & 10B are simplified pictorial illustrations of an arthroscopic surgical device constructed and operative in accordance with a preferred embodiment of the present invention, showing opposite views in a tenth operative orientation;

FIGS. 11A & 11B are simplified pictorial illustrations of an arthroscopic surgical device constructed and operative in accordance with a preferred embodiment of the present invention, showing opposite views in an eleventh operative orientation;

FIG. 14C is a simplified partially assembled view of the portion of the arthroscopic surgical device of FIGS. 14A and 14B;

FIGS. 15A and 15B are simplified illustrations of another portion of the arthroscopic surgical device of FIGS. 1A-13, showing opposite views;

FIGS. 16A and 16B are simplified exploded view illustrations of the portion of the arthroscopic surgical device of FIGS. 1A-13, showing opposite views;

FIGS. 18A and 18B are simplified assembled view illustrations of a portion of the arthroscopic surgical device of FIGS. 1A-17B, showing opposite views;

FIG. 19 is a simplified exploded view illustration of the portion of the arthroscopic surgical device of FIGS. 18A and 18B;

FIGS. 20A, 20B, 20C & 20D are simplified pictorial illustrations showing various configurations of a top of the portion of the arthroscopic surgical device shown in FIGS. 18A, 18B and 19;

FIG. 21 is a simplified cross-sectional illustration taken along lines XXI-XXI in FIG. 18A;

FIG. 22 is a simplified cross-sectional illustration taken along lines XXII-XXII in FIG. 21;

FIGS. 24A and 24B are simplified exploded view illustrations of the portion of the arthroscopic surgical device shown in FIGS. 18A, 18B and 19, showing opposite views;

FIGS. 25A & 25B are simplified illustrations of steps in the assembly of the portion of the arthroscopic surgical device shown in FIGS. 18A, 18B and 19;

FIGS. 26A & 26B are simplified pictorial illustrations of parts of the portion of the arthroscopic surgical device shown in FIGS. 18A, 18B and 19;

FIG. 27 is a simplified side view illustration taken along the direction indicated by an arrow XXVII in FIG. 26A;

FIG. 28 is a simplified sectional illustration taken along the lines XXVIII-XXVIII in FIG. 27;

FIG. 29 is a simplified sectional illustration taken along the lines XXIX-XXIX in FIG. 28;

FIGS. 31A, 31B, 31C, 31D, 31E, 31F, 31G, 31H, 31I, 31J, 31K, 31L, 31M and 31N are simplified illustrations of operation of the arthroscopic surgical device of FIGS. 1A-30N in a clinical context.

DETAILED DESCRIPTION OF PREFERRED EMBODIMENTS

Figures 12A, 12B:
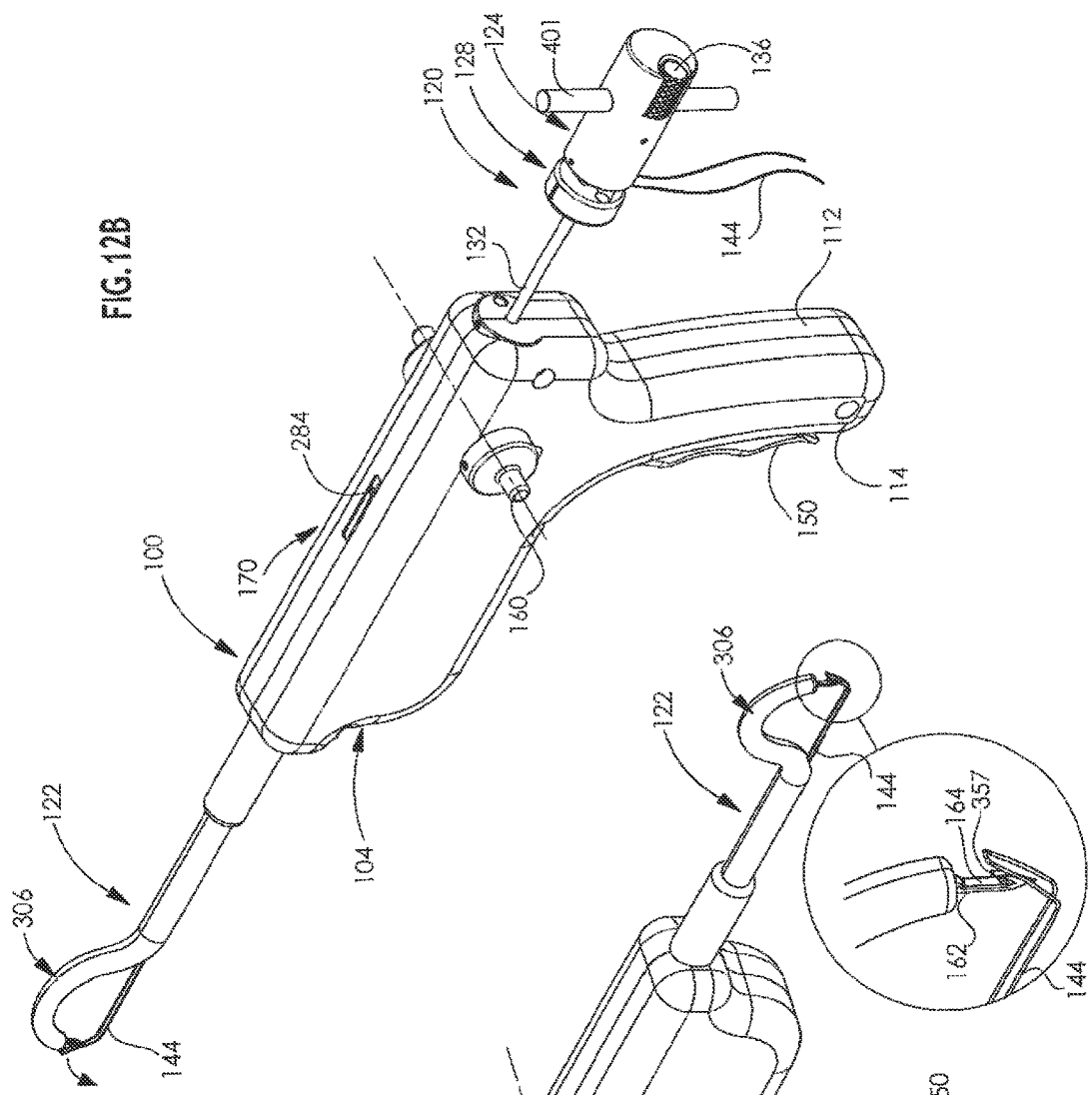
FIGS. 12A & 12B are simplified pictorial illustrations of an arthroscopic surgical device constructed and operative in accordance with a preferred embodiment of the present invention, showing opposite views in a twelfth operative orientation.

Reference is now made to FIGS. 1A & 1B, which are simplified pictorial illustrations of an arthroscopic surgical device constructed and operative in accordance with a preferred embodiment of the present invention, showing opposite views in a first operative orientation and to various additional drawings which are specifically referenced in parentheses hereinbelow.

As seen in FIGS. 1A & 1B, an arthroscopic surgical device 100 according to a preferred embodiment of the present invention includes a housing portion, preferably formed of right and left housing elements 102 and 104, and a multiple action driving assembly 106, only part of which is seen in FIGS. 1A & 1B. The housing portion includes a handle portion, which is defined by respective right and left housing element handle portions 112 and 114, respectively.

The multiple action driving assembly 106 preferably includes a bone-engaging pin driving assembly 120 and a bone-engaging needle driving assembly 122. Bone-engaging pin driving assembly 120 preferably includes a base assembly 124 including a rearward portion 126 and a forward portion 128. An inner, solid pin 130 (FIG. 21) is fixedly mounted onto rearward portion 126 and an outer, hollow pin 132 is fixedly mounted onto forward portion 128.

A rearward knurled locking knob 136 is mounted onto rearward portion 126 and selectably locks rearward portion 126 to forward portion 128. A forward knurled locking knob 138 is mounted onto forward portion 128 and selectably locks forward portion 128 to the left housing element handle portion 112.

Outer hollow pin 132 is preferably formed with a pointed tip 140 and with a throughgoing top to bottom aperture 142. A suture 144 preferably extends between the inner pin 130 (FIG. 21) and the outer pin 132, being looped about the inner pin 130 (FIG. 21) interiorly of the outer pin 132 so as to be engageable through aperture 142.

Figure 13:
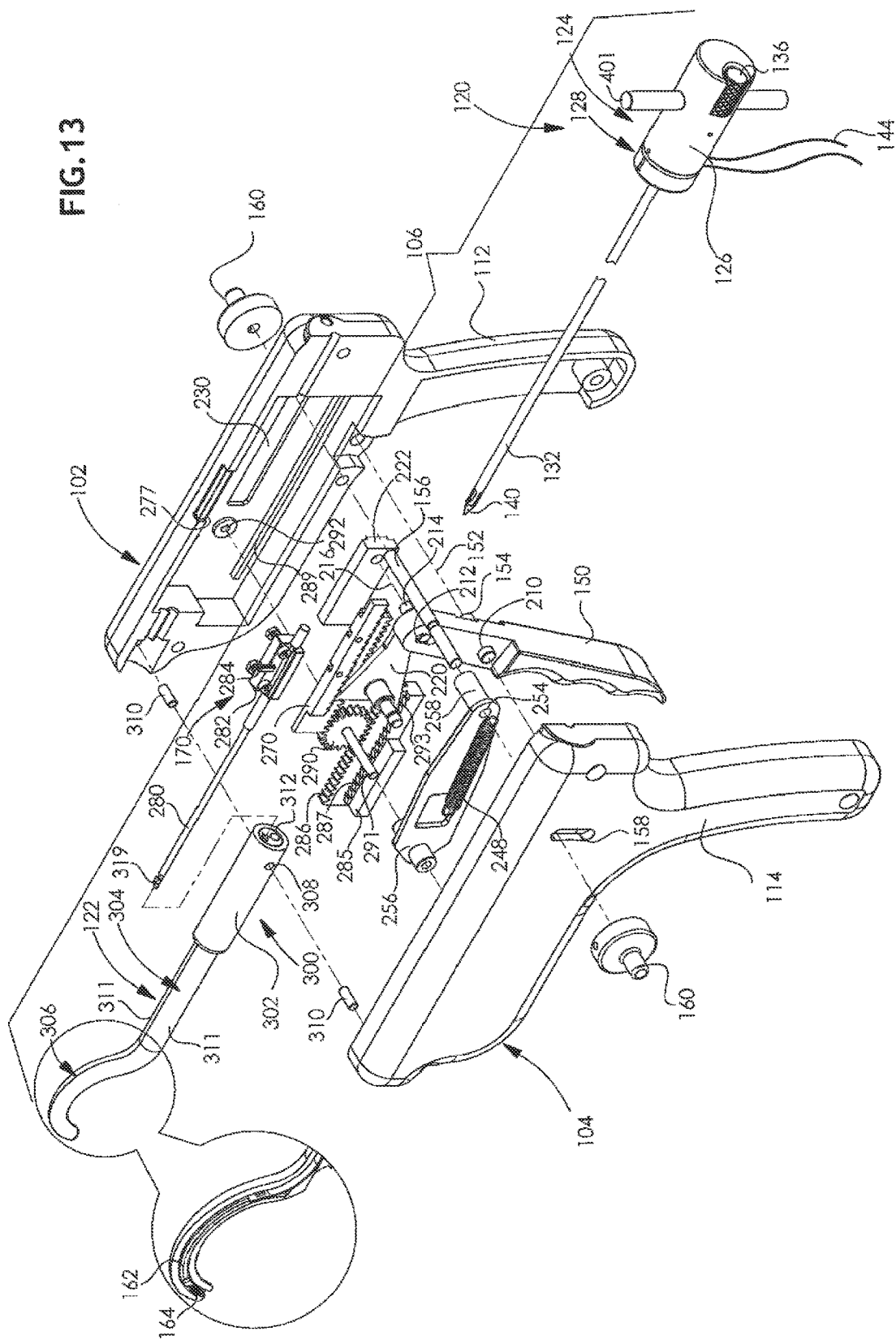
FIG. 13 is a simplified exploded view illustration of the arthroscopic surgical device of FIGS. 1A-12B in the first operative orientation.

The multiple action driving assembly 106 preferably includes a hand-engageable ratchet handle 150 which is arranged for reciprocal motion about an axis 152 (FIG. 13). A selectable direction ratchet shaft 156 (FIG. 13) extends through slots 158 in respective right and left housing element handle portions 112 and 114, and terminates in knobs 160, whose positions in slots 158 govern the direction of motion of an arthroscopic arcuate tunneling needle 162 having a suture engagement groove 164.

A visible mechanical indicator 170 is preferably arranged on the top of respective housing portions 102 and 104. Indicator 170 preferably provides a visible indication of the extent that arcuate tunneling needle 162 is displaced from its fully retracted position shown in FIGS. 1A & 1B. Arcuate tunneling needle 162 is adapted to selectably engage suture 144 at suture engagement groove 164 via aperture 142 in outer pin 132.

Reference is now made to FIGS. 2A & 2B, which are simplified pictorial illustrations of the arthroscopic surgical device of FIGS. 1A & 1B, showing opposite views in a second operative orientation. It is seen that in the second operative orientation, which preferably takes place following insertion of a forward portion of the bone-engaging needle driving assembly 122 through an arthroscopic incision, as described hereinbelow in detail with reference to FIG. 31B, the bone-engaging pin driving assembly 120 is inserted through the housing so that tip 140 extends to the surface of the bone, as described hereinbelow in detail with reference to FIG. 31B.

Reference is now made to FIGS. 3A & 3B, which are simplified pictorial illustrations of the arthroscopic surgical device of FIGS. 1A-2B in a third operative orientation. It is seen that bone-engaging pin driving assembly 120 is fully extended, typically by hammering on the rearward portion 126, as described hereinbelow in detail with reference to FIG. 31C.

Reference is now made to FIGS. 4A & 4B, which are simplified pictorial illustrations of the arthroscopic surgical device of FIGS. 1A-3B in a fourth operative orientation. It is seen that, following unlocking of rearward portion 126 from the forward portion 128 by rotation of knurled knob 136, rearward portion 126 is retracted axially relative to forward portion 128 thereby retracting inner pin 130 (FIG. 21) relative to outer pin 132.

Reference is now made to FIGS. 5A & 5B, which are simplified pictorial illustrations of the arthroscopic surgical device of FIGS. 1A-4B in a fifth operative orientation. It is seen that arcuate tunneling needle 162 is partially extended, as indicated by indicator 170. This extension is produced by rotation of hand-engageable ratchet handle 150 about axis 152 (FIG. 13) when knobs 160 are in the upper position in slots 158.

Reference is now made to FIGS. 6A & 6B, which are simplified pictorial illustrations of the arthroscopic surgical device of FIGS. 1A-5B in a sixth operative orientation. It is seen that arcuate tunneling needle 162 is fully extended through aperture 142 in outer pin 132, as indicated by indicator 170 and in response to reciprocal rotation of hand-engageable ratchet handle 150 about axis 152 when knobs 160 are in the upper position in slots 158.

Reference is now made to FIGS. 7A & 7B, which are simplified pictorial illustrations of the arthroscopic surgical device of FIGS. 1A-6B in an seventh operative orientation. It is seen that suture 144 is manually retracted so that it engages arcuate tunneling needle 162 at suture engagement groove 164 via aperture 142 in outer pin 132. Preferably prior to retraction of suture 144, knobs 160 are lowered to their lower position in slots 158.

Reference is now made to FIGS. 8A & 8B, which are simplified pictorial illustrations of the arthroscopic surgical device of FIGS. 1A-7B in an eighth operative orientation. It is seen that arcuate tunneling needle 162 is partially retracted in response to reciprocal rotation of hand-engageable ratchet handle 150 about axis 152 when knobs 160 are in the lower position in slots 158 and while suture 144 is engaged with needle 162 at suture engagement groove 164 thereof.

Reference is now made to FIGS. 9A & 9B, which are simplified pictorial illustrations of the arthroscopic surgical device of FIGS. 1A-8B in a ninth operative orientation. It is seen that arcuate tunneling needle 162 is further retracted, as indicated by indicator 170, thereby pulling suture 144 therewith out through aperture 142 of outer pin 132, thus drawing the suture 144 backwards along with retraction of the needle 162 along an arcuate path earlier defined through the bone by the arcuate tunneling operation of needle 162. This retraction of needle 162 results from further reciprocal rotation of hand-engageable ratchet handle 150 about axis 152 when knobs 160 are in the lower position in slots 158.

Reference is now made to FIGS. 10A & 10B, which are simplified pictorial illustrations of the arthroscopic surgical device of FIGS. 1A-9B in a tenth operative orientation. Arcuate tunneling needle 162 is fully retracted as indicated by indicator 170, in engagement with the forward looped end of suture 144, thus drawing the suture backwards along an arcuate path along with full retraction of the needle 162.

Reference is now made to FIGS. 11A & 11B, which are simplified pictorial illustrations of the arthroscopic surgical device of FIGS. 1A-10B in an eleventh operative orientation. It is seen that bone-engaging pin driving assembly 120 is retracted after unlocking assembly 120 from handle portion 112 by rotation of knurled knob 138.

Reference is now made to FIGS. 12A & 12B, which are simplified pictorial illustrations of the arthroscopic surgical device of FIGS. 1A-11B in an twelfth operative orientation. It is seen that arcuate tunneling needle 162 is now partially extended in order to permit manual disengagement of the looped forward end of suture 144 from suture engagement groove 164 of needle 162. It is noted that the positions of knobs 160 in slots 158 were previously shifted upwardly, in order to provide extension of needle 162 in response to ratchet operation. The orientations of the needle 162 is shown by indicator 170.

Figure 14A:
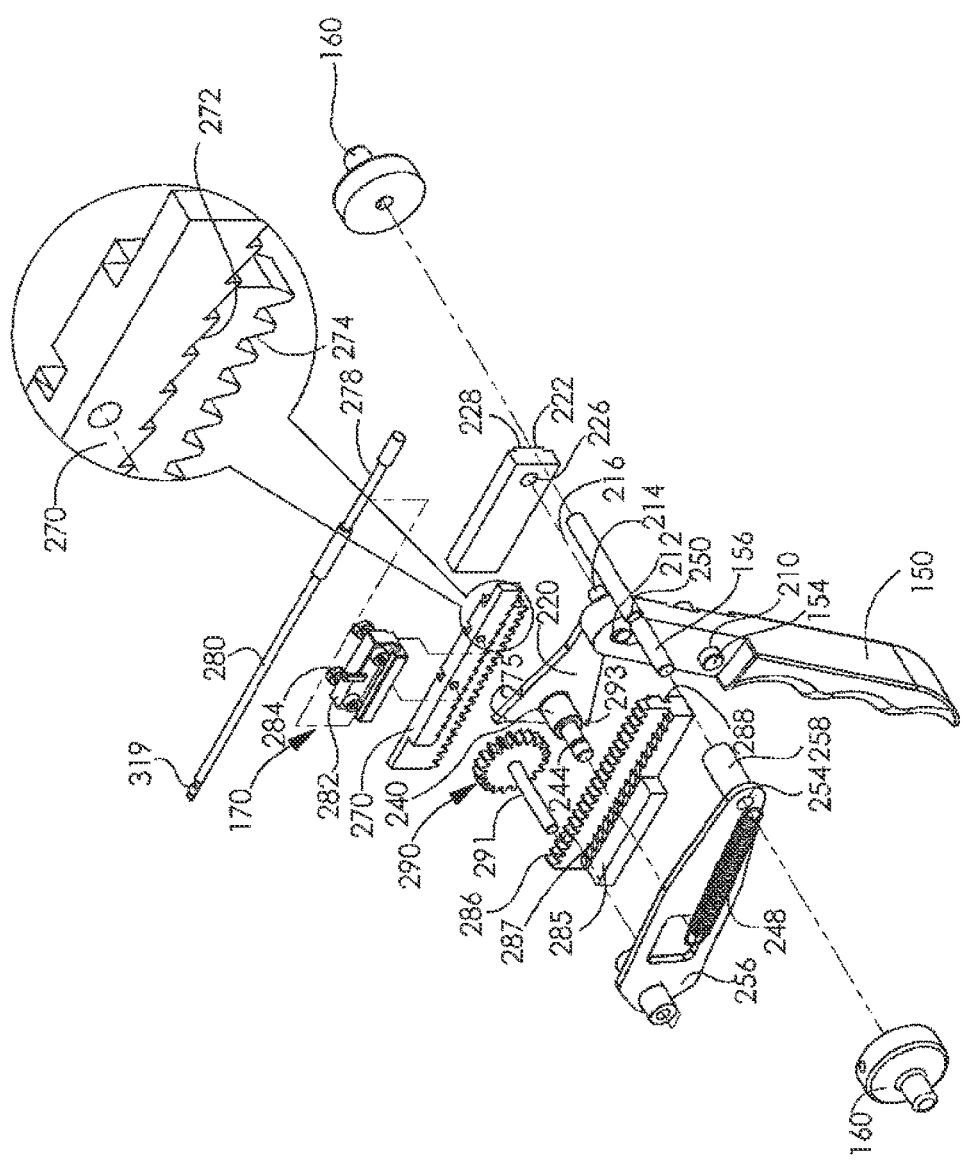
FIGS. 14A and 14B are simplified exploded view illustrations of a portion of the arthroscopic surgical device of FIGS. 1A-13, showing opposite views.
Figure 14B:
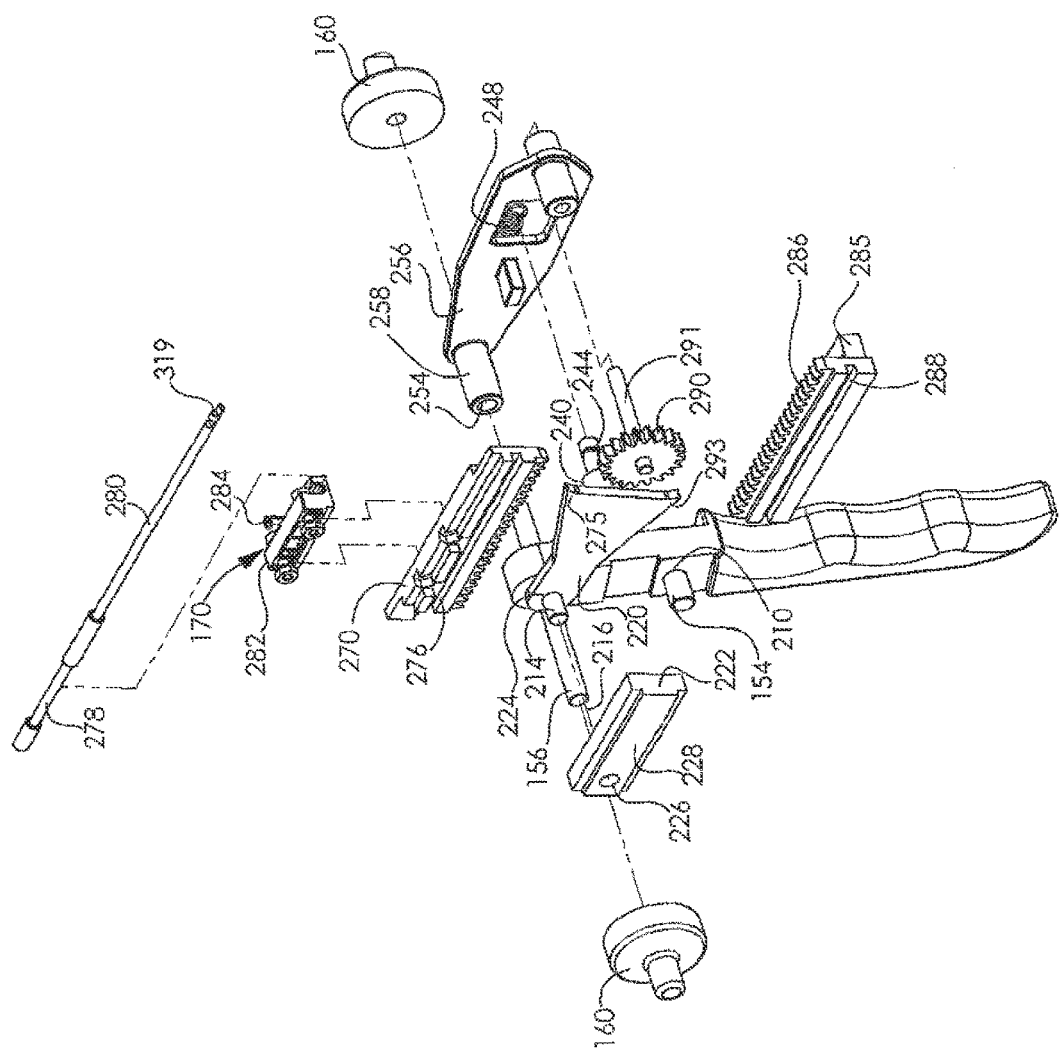
Figures 17A, 17B:
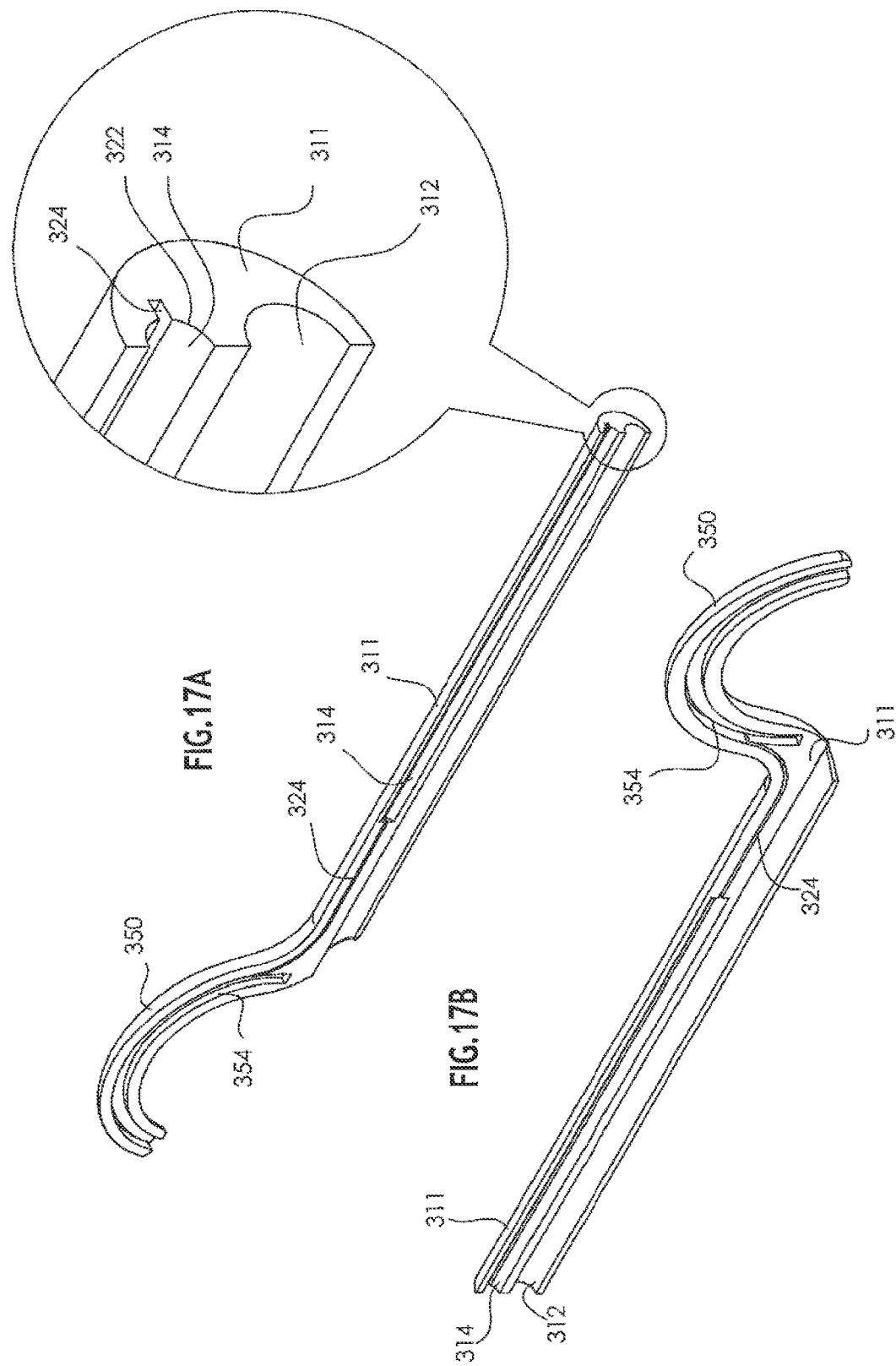
FIGS. 17A and 17B are simplified illustrations of part of the portion of the arthroscopic surgical device of FIGS. 16A & 16B, showing opposite views.

Reference is now made to FIGS. 13-17B and initially specifically to FIG. 13 and to FIGS. 14A and 14B, which are simplified exploded view illustrations of a portion of the arthroscopic surgical device of FIGS. 1A-12, showing opposite views, and to FIG. 14C, which is a simplified partially assembled view, all of which show details of some elements of multiple action driving assembly 106.

It is seen that ratchet handle 150 is typically formed with a lower aperture 210, which accommodates a shaft 154, and a slot 212. A pin 214 is slidably movable in slot 212, such that reciprocal arcuate motion of slot 212 is translated into reciprocal planar forward and rearward motion perpendicular to a longitudinal axis 216 of pin 214. First and second reciprocal motion connection elements 220 and 222 are fixed to pin 214 at respective apertures 224 and 226 and move together therewith in reciprocal forward and rearward linear motion in response to rotational motion of ratchet handle 150.

Connection element 222 includes an elongate protrusion 228, which moves reciprocally in a slot 230 formed in housing portion 102.

Connection element 220 includes a side extending shaft 240 which includes a circumferential groove 244 onto which is mounted one end of a tension spring 248. An opposite end of tension spring 248 is mounted in a circumferential groove 250 formed in shaft 156. Shaft 156 extends through an aperture 254 formed in a toggle element 256, which communicates with a hollow shaft portion 258 of toggle element 256. Shaft 156 extends through slots 158 formed on respective housing portions 102 and 104.

A double rack linear toothed element 270 is provided with an upper linear toothed ratchet rack 272 and a lower linear toothed gear rack 274. A pointed corner 275 of connection element 220 selectably engages upper linear toothed rack 272. Double rack linear toothed element 270 is preferably formed with a slot 276 which engages an elongate axial protrusion 277 formed in housing element 102.

An inward recessed portion 278 adjacent an inner end of a generally rigid flexible needle driving strip driving shaft 280 is fixedly mounted onto double rack linear toothed element 270 by means of a mounting element 282 which is typically bolted onto element 270. An indicator finger 284 is formed on mounting element 282 and forms part of indicator 170.

A second double rack linear toothed element 285 is provided with an upper linear toothed gear rack 286 and a lower linear toothed ratchet rack 287. Double rack linear toothed element 285 is preferably formed with a slot 288 which engages an elongate axial protrusion 289 formed in housing element 102.

A gear 290, having a gear shaft 291, engages lower linear toothed gear rack 274 of element 270 and also simultaneously engages upper linear toothed gear rack 286 of element 285. Gear shaft 291 preferably is mounted at its opposite ends in apertures 292 in respective housing elements 102 and 104.

A pointed corner 293 of connection element 220 selectably engages lower linear toothed ratchet rack 287 of element 285.

Reference is now made specifically to FIGS. 15A-17B, which illustrate bone-engaging needle driving assembly 122. The bone-engaging needle driving assembly 122 includes linear gear rack element 270, which is preferably driven along an elongate travel path responsive to reciprocal motion of ratchet handle 150.

Bone-engaging needle driving assembly 122 includes a static forward portion 300, including a mounting base 302, which extends forwardly of a forward end of the housing, which is fixed to an extension shaft 304 extending axially inwardly thereof and forwardly therefrom. Fixed to extension shaft 304 and extending forwardly thereof, there is preferably formed an arcuate needle storage and guiding portion 306.

Mounting base 302 is generally configured as a hollow cylinder to accommodate part of extension shaft 304 therewithin and is formed with matching side apertures 308 which accommodate mounting pins 310 (FIG. 13), which serve to mount the mounting base 302 onto housing portions 102 and 104, as seen in FIG. 13.

Extension shaft 304 is preferably formed of two identical side by side pieces 311. Side pieces 311 together define two mutually spaced axial mounting bores extending therethrough, which bores are designated by reference numerals 312 and 314. Bore 312 slidably accommodates hollow pin 132 and has a generally round cross-section.

Bore 314 slidably accommodates parts of a flexible arcuate needle driving assembly, which preferably includes a flexible needle driving strip 318, preferably formed of spring steel, and generally rigid flexible needle driving strip driving shaft 280, which is mounted at the rear of flexible needle driving strip 318, preferably as shown in enlargements A & B in FIG. 15A. This mounting is preferably by means of engagement of a protrusion 319 formed adjacent the forward end of rigid flexible needle driving strip driving shaft 280 with a corresponding aperture 320 formed adjacent a rearward end of flexible needle driving strip 318.

As seen in enlargement A of FIG. 15A, bore 314 has a generally circular cross sectional central portion 322 to accommodate shaft 280, from which portion extend a pair of symmetrical side cut outs 324 to accommodate the side edges of strip 318.

As seen particularly in enlargement D of FIG. 15A, forward of extension shaft 304, there is preferably formed an arcuate needle storage and guiding portion 350, which is formed with an arcuate bore 352 including a portion 354 having a generally rectangular cross section, which slidably accommodates needle 162. A pair of symmetrical side cut outs 356 extend outwardly from portion 354 and accommodate the side edges of flexible needle driving strip 318.

As seen particularly in FIG. 16A, it is seen that suture engagement groove 164 of arcuate needle 162 is partially defined by a partially overlying portion 357 of needle 162. It is also seen in an enlargement of FIG. 16A, that the forward end of flexible needle driving strip 318 is attached to arcuate needle 162. This attachment is preferably by means of engagement of a protrusion 366 formed adjacent the rearward end of arcuate needle 162 with a corresponding aperture 367 formed adjacent a forward end of flexible needle driving strip 318.

Reference is now made to FIGS. 18A & 18B and FIG. 19, which illustrate bone-engaging pin driving assembly 120. As noted above, bone-engaging pin driving assembly 120 preferably includes a base assembly 124 including a rearward portion 126 and a forward portion 128. An inner, solid pin 130 is fixedly mounted onto rearward portion 126 and an outer, hollow pin 132 is fixedly mounted onto forward portion 128.

A rearward knurled locking knob 136 is mounted onto rearward portion 126 and selectably locks rearward portion 126 to forward portion 128. A forward knurled locking knob 138 is mounted onto forward portion 128 and selectably locks forward portion 128 to the left housing element handle portion 112.

Outer hollow pin 132 is preferably formed with a pointed tip 140 and with a throughgoing top to bottom aperture 142. A suture 144 preferably extends between the inner pin 130 and the outer pin 132, being looped about the inner pin 130 interiorly of the outer pin 132 so as to be engageable through aperture 142.

As seen particularly in FIGS. 18A, 18B and 19, extending perpendicularly to throughgoing top to bottom aperture 142 there is formed a throughgoing side wall slot 400, which, as will be described hereinbelow, accommodates suture 144. FIGS. 18A, 18B and 19 also illustrate a throughgoing shaft 401 which extends through a corresponding side-to-side bore formed in rearward portion 126. FIGS. 24A and 24B show the various elements which are assembled as seen in FIGS. 18A, 18B and 19, but without the suture 144, for clarity.

FIGS. 20A, 20B, 20C and 20D show various alternative configurations of pointed tip 140. FIG. 20A shows a generally conical tip 402 having a suture accommodating slot 404. FIG. 20B shows a generally tapered screw threaded tip 406 having a suture accommodating slot 408. FIG. 20C shows a generally conical drill tip 410 having a suture accommodating slot 412. FIG. 20D shows a generally diamond cut tip 414 having a suture accommodating slot 416.

Reference is now made to FIGS. 21-23C, which illustrate the initial positioning of suture 144 in the bone-engaging pin driving assembly 120.

Figure 23A:
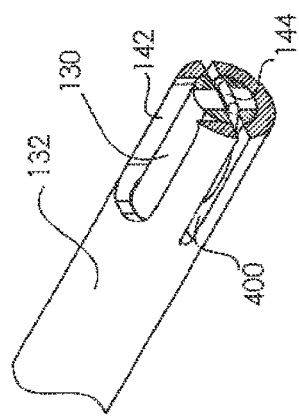
FIGS. 23A, 23B and 23C are simplified cross-sectional illustrations taken along lines A-A, B-B and C-C in FIG. 18A.
Figure 23B:
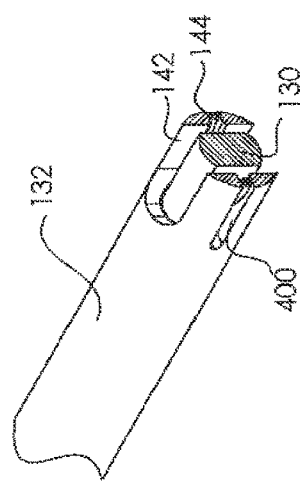
Figure 23C:
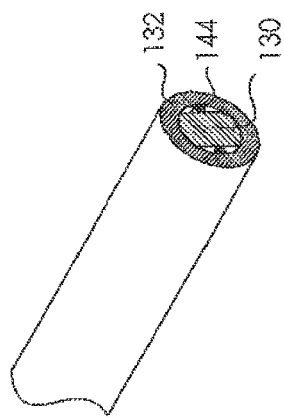

FIG. 21 is a simplified cross-sectional illustration taken along lines XXI-XXI in FIG. 18A and FIG. 22 is a simplified cross-sectional illustration taken along lines XXII-XXII in FIG. 21. FIGS. 23A-23C are cross-sectional illustrations taken as indicated in FIG. 18A. These drawings clearly illustrate the orientation of the suture 144 with respect to pins 130 and 132 and aperture 142 and slot 400 and show how the suture 144 is wound around pin 130 and between the end of pin 130 and tip 140 and partially lies in both sides of slot 400.

FIGS. 25A and 25B show assembly of the bone-engaging pin driving assembly 120. Once the suture 144 has been wound around inner pin 130 as seen in FIG. 25A, rearward portion 126, including the inner pin 130 having the suture 144 wound thereon, is joined to forward portion 128 by inserting pin 130 into pin 132 through bore 480 (FIG. 26A). The rearward portion 126 is then locked to the forward portion 128 by operation of knob 136. Insertion of a retaining pin 420 into rearward portion 126 serves to limit the axial separation of the forward and rearward portions 128 and 126 respectively and thus to limit the axial retraction of pin 130 relative to pin 132. A further retaining pin 424 may be provided for locking knob 136 against disengagement from rearward portion 126.

Reference is now made to FIGS. 26A & 26B, which are simplified pictorial illustrations of parts of the portion of the arthroscopic surgical device shown in FIGS. 18A, 18B and 19, FIG. 27, which is a simplified side view illustration taken along the direction indicated by an arrow XXVII in FIG. 26A, FIG. 28, which is a simplified sectional illustration taken along the lines XXVIII-XXVIII in FIG. 27, and FIG. 29, which is a simplified sectional illustration taken along the lines XXIX-XXIX in FIG. 28.

Rearward portion 126 is preferably a generally cylindrical element 428 extending along a cylindrical axis 430 and is formed with various bores and slots as described hereinbelow. A side slot 432 extends axially forwardly from a rear surface 434 of element 428 along approximately one third of the axial length of element 428 and terminates in a narrowed axial bore 436 which extends all of the way to a forward surface 438 of element 428. A transverse bore 439 communicates with bore 436 and accommodates pin 424 (FIG. 19) for retaining knob 136 (FIG. 19) in bore 436 and in slot 432.

A transverse bore 440 extends perpendicularly to axis 430 and accommodates shaft 401 (FIGS. 18A, 18B & 19).

A side slot 442 extends axially rearwardly from forward surface 438 of element 428 along approximately two thirds of the axial length of element 428. Side slot 442 accommodates knob 138.

A bore 450, having a generally rectangular cross section, is formed on forward surface 438. A transverse bore 452 communicates with bore 450 and accommodates pin 420

(FIG. 19) for limiting axial displacement of the forward portion 128 relative to the rearward portion 126.

Forward portion 128 is preferably a generally disk-like cylindrical element 468 extending along cylindrical axis 430 and is formed with various bores, slots and protrusions as described hereinbelow. A side slot 472 extends axially forwardly from a rear surface 474 of element 468 through to a forward surface 478 of element 468.

A central bore 480 extends axially rearwardly from forward surface 478 of element 468 to rear surface 474 of element 468 and therebeyond through an axial protrusion 482, having a generally rectangular cross section, as a side opened slot 484. A transverse retaining slot 486, extending perpendicularly to axis 430 is provided on a top surface of protrusion 482 and is engaged by pin 420 for limiting axial displacement of protrusion 482 within bore 450, thus limiting relative displacement of the forward and rearward portions 128 and 126 respectively and thus limiting retraction of pin 130 within pin 132.

A stepped, partially threaded bore 490 extends forwardly from rear surface 474 as a threaded portion 492 and continues at a shoulder 494 as a non-threaded bore portion 496 to forward surface 478.

A suture access slot 498 communicates with central bore 480 and allows threading of suture 144 therethrough.

Reference is now made to FIGS. 30A, 30B, 30C, 30D, 30E, 30F, 30G, 30H, 30I, 30J, 30K, 30L, 30M and 30N, which illustrate details of the operation of the arthroscopic surgical device of FIGS. 1A-29, and to FIGS. 31A, 31B, 31C, 31D, 31E, 31F, 31G, 31H, 31I, 31J, 31K, 31L, 31M and 31N, which are simplified illustrations of operation of the arthroscopic surgical device of FIGS. 1A-30N in a clinical context.

Figure 30A:
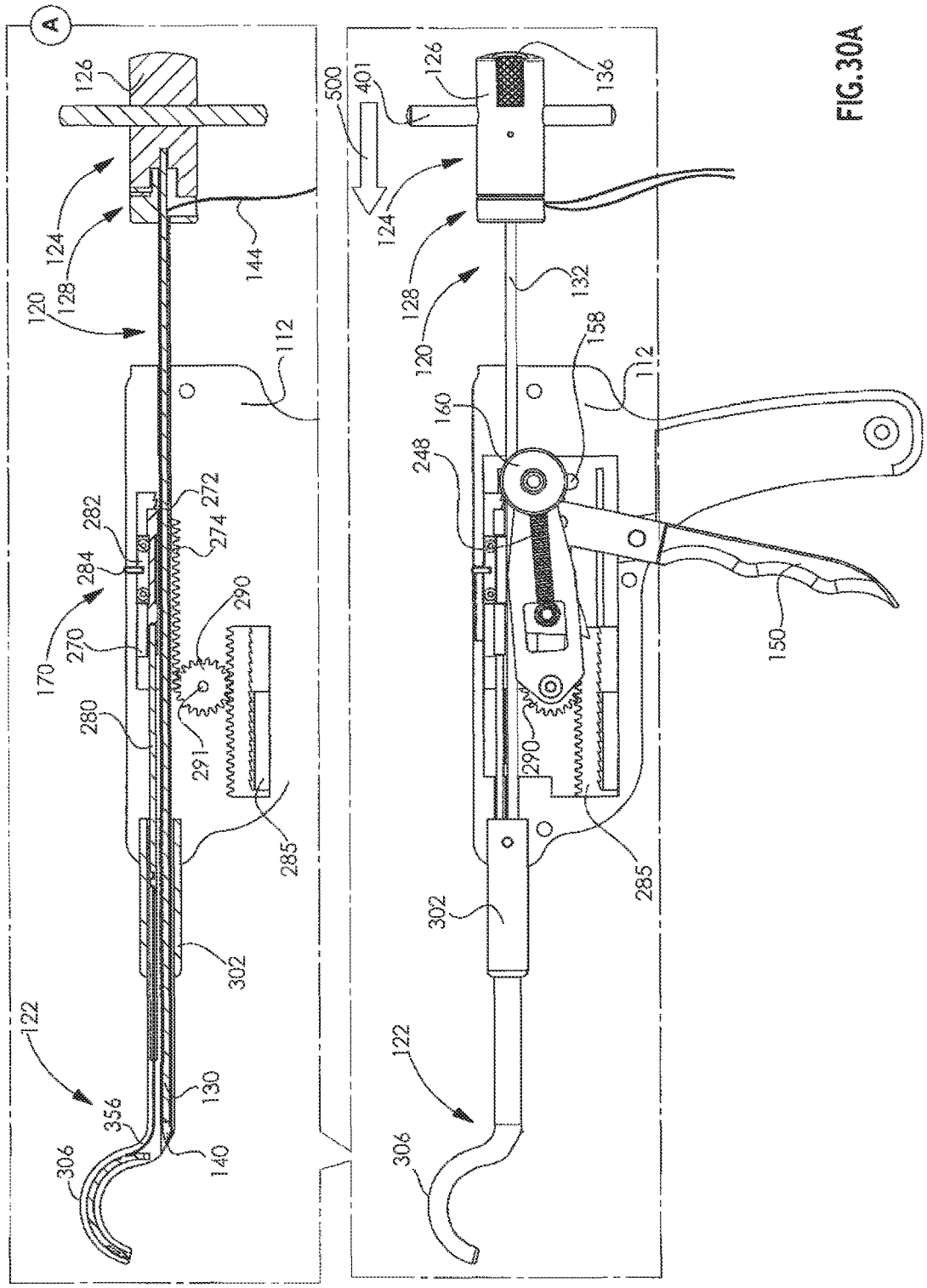
FIGS. 30A, 30B, 30C, 30D, 30E, 30F, 30G, 30H, 30I, 30J, 30K, 30L, 30M and 30N are respective simplified illustrations of details of the operation of the arthroscopic surgical device of FIGS. 1A-29.

As seen in FIGS. 30A and 31A, which correspond generally to FIGS. 1A-2B, prior to insertion of the arthroscopic surgical device 100 through an arthroscopic incision in a patient, a bone-engaging pin driving assembly 120, such as that described hereinabove with reference to FIGS. 18A-29, is mounted onto the arthroscopic surgical device 100.

FIG. 31A shows initial forward axial positioning of bone-engaging pin driving assembly 120 in the arthroscopic surgical device 100, as indicated by an arrow 500. At this stage, the tip 140 of the bone-engaging pin driving assembly 120 does not protrude out from bore 312.

Figure 31B:
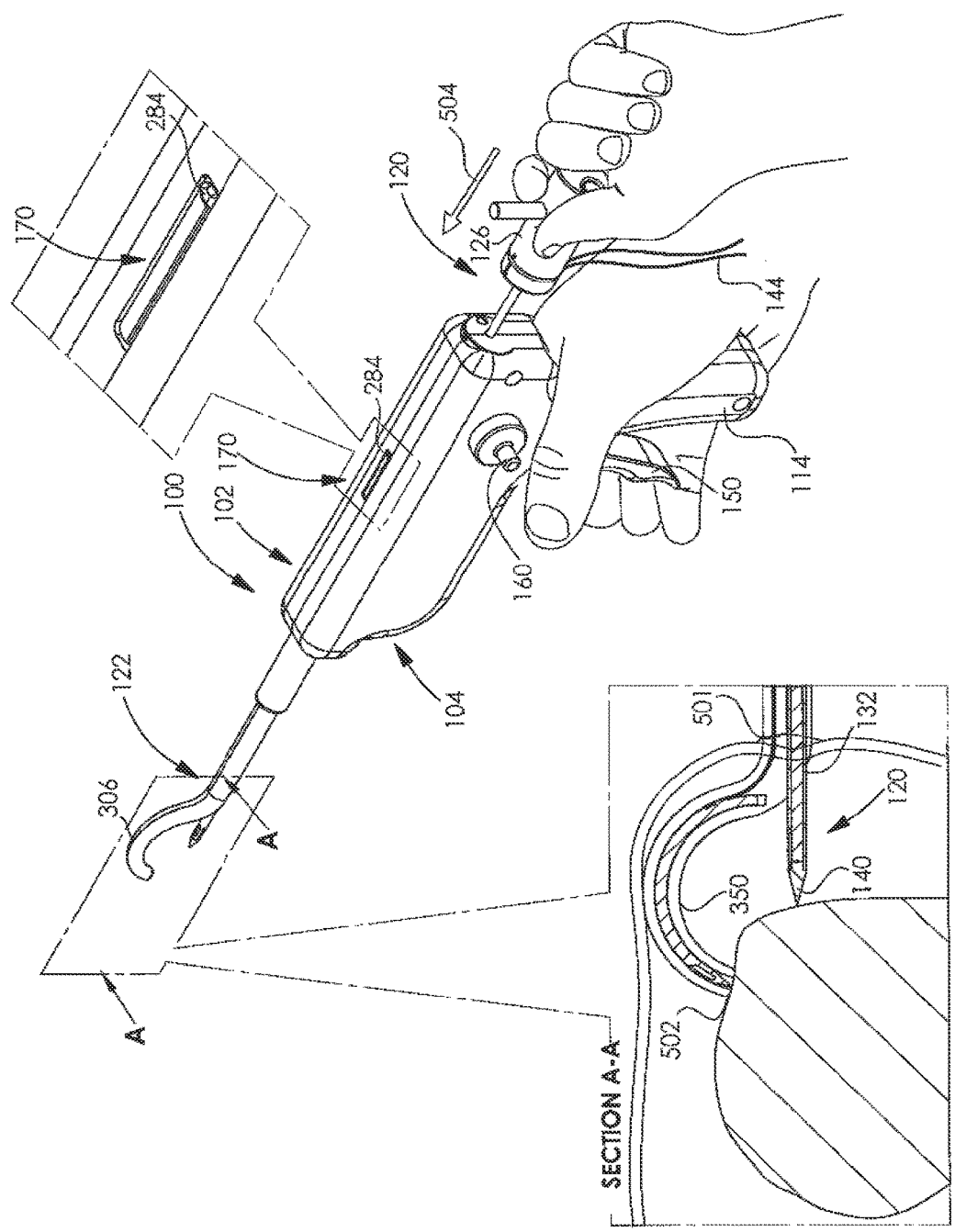

FIG. 31B shows insertion of arcuate needle storage and guiding portion 306 through an incision 501 such that a forwardmost end 502 of arcuate needle storage and guiding portion 306 engages a bone, here shown as a humerus.

It is seen in FIGS. 30A, 31A & 31B that the inner, solid pin 130 and outer, hollow pin 132 are in their respective fully retracted positions.

Figure 30B:
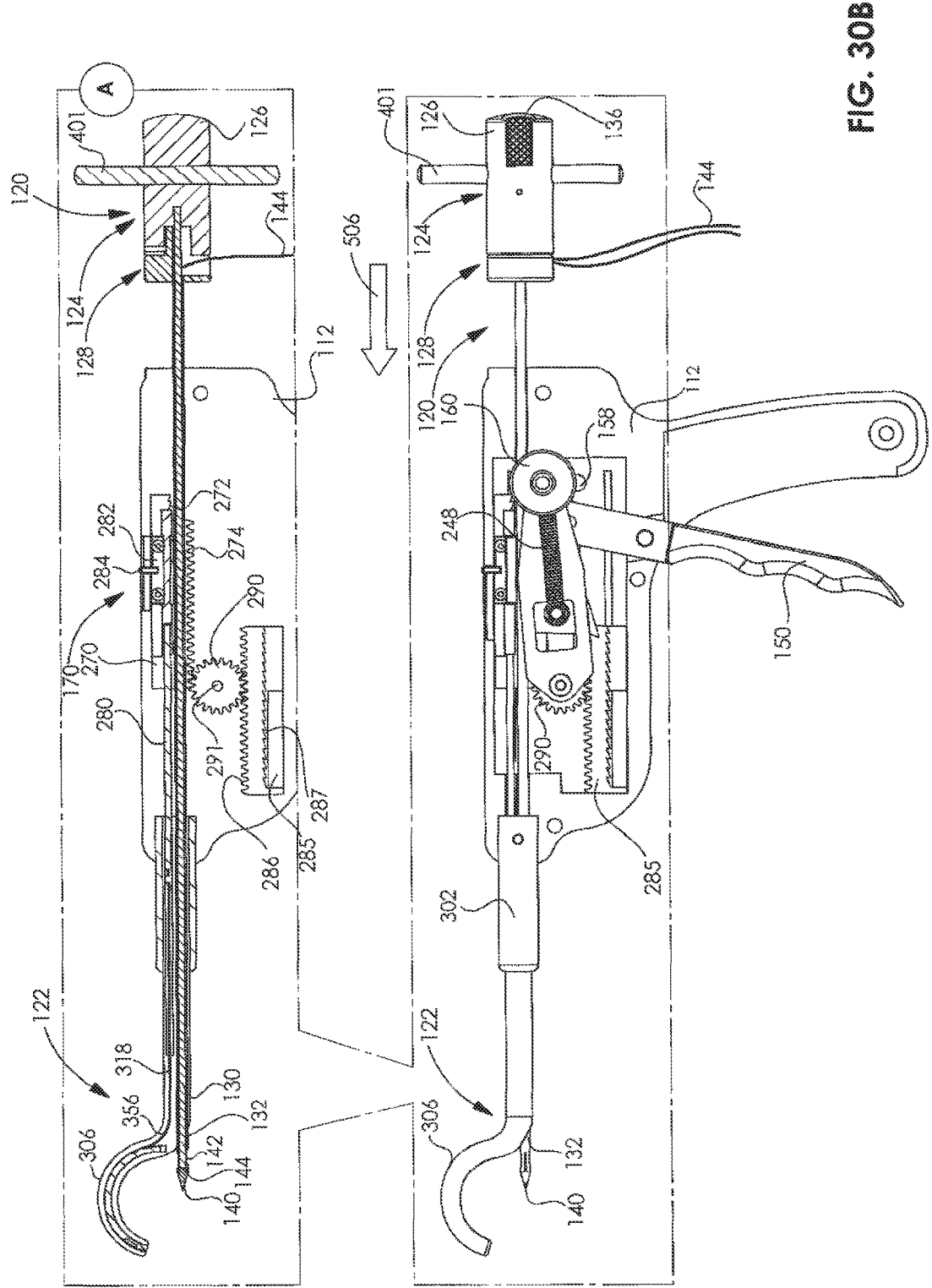
Figure 31C:
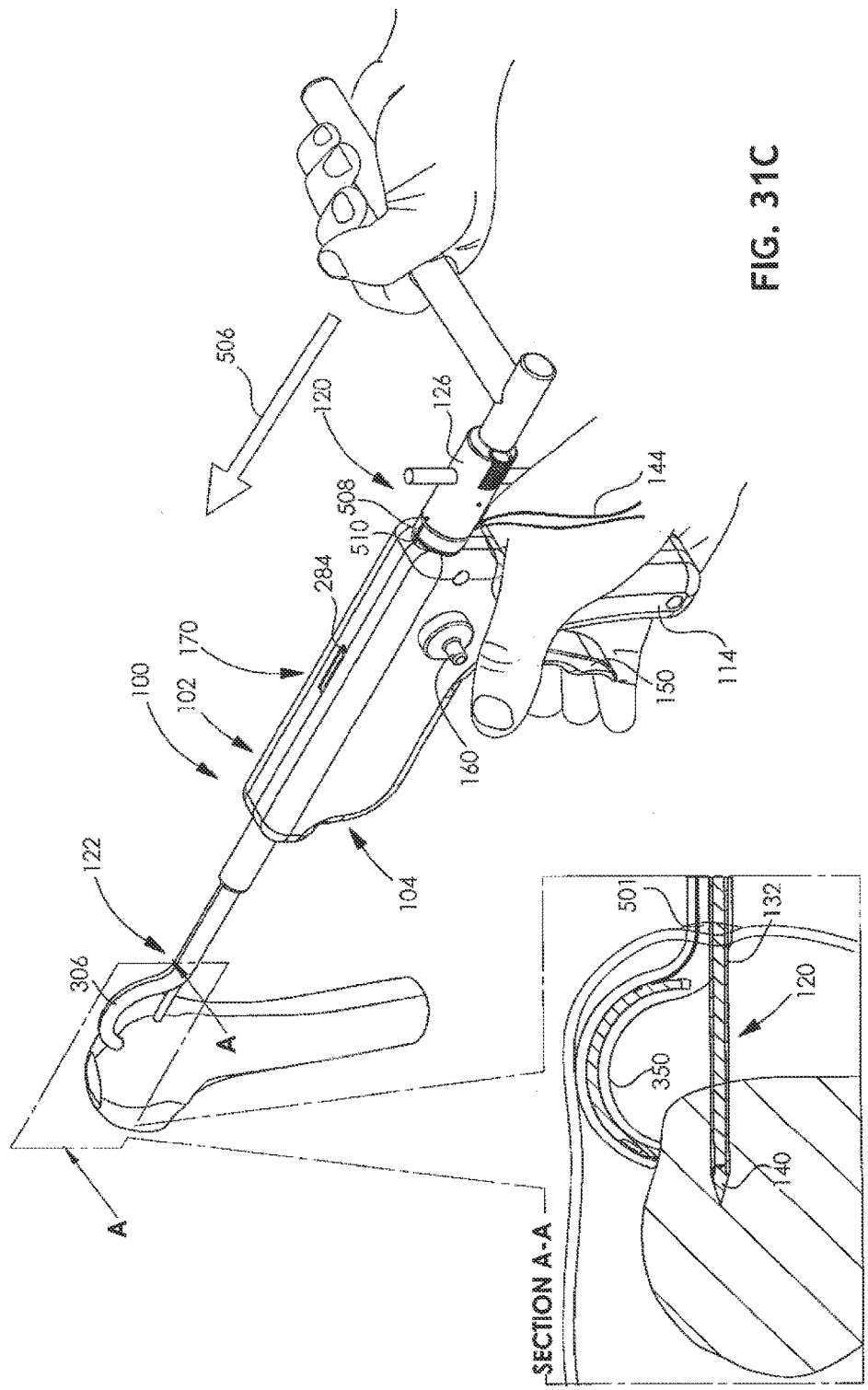

FIGS. 30B and 31C, which correspond generally to FIGS. 2A & 2B, show further linear forward displacement of bone-engaging pin driving assembly 120 in the arthroscopic surgical device 100, as indicated by an arrow 504. This displacement is preferably achieved by an operator manually pushing the bone-engaging pin driving assembly 120 forwardly relative to the remainder of the arthroscopic surgical device 100, as indicated by arrow 504, until tip 140 engages the bone.

Figure 30C:
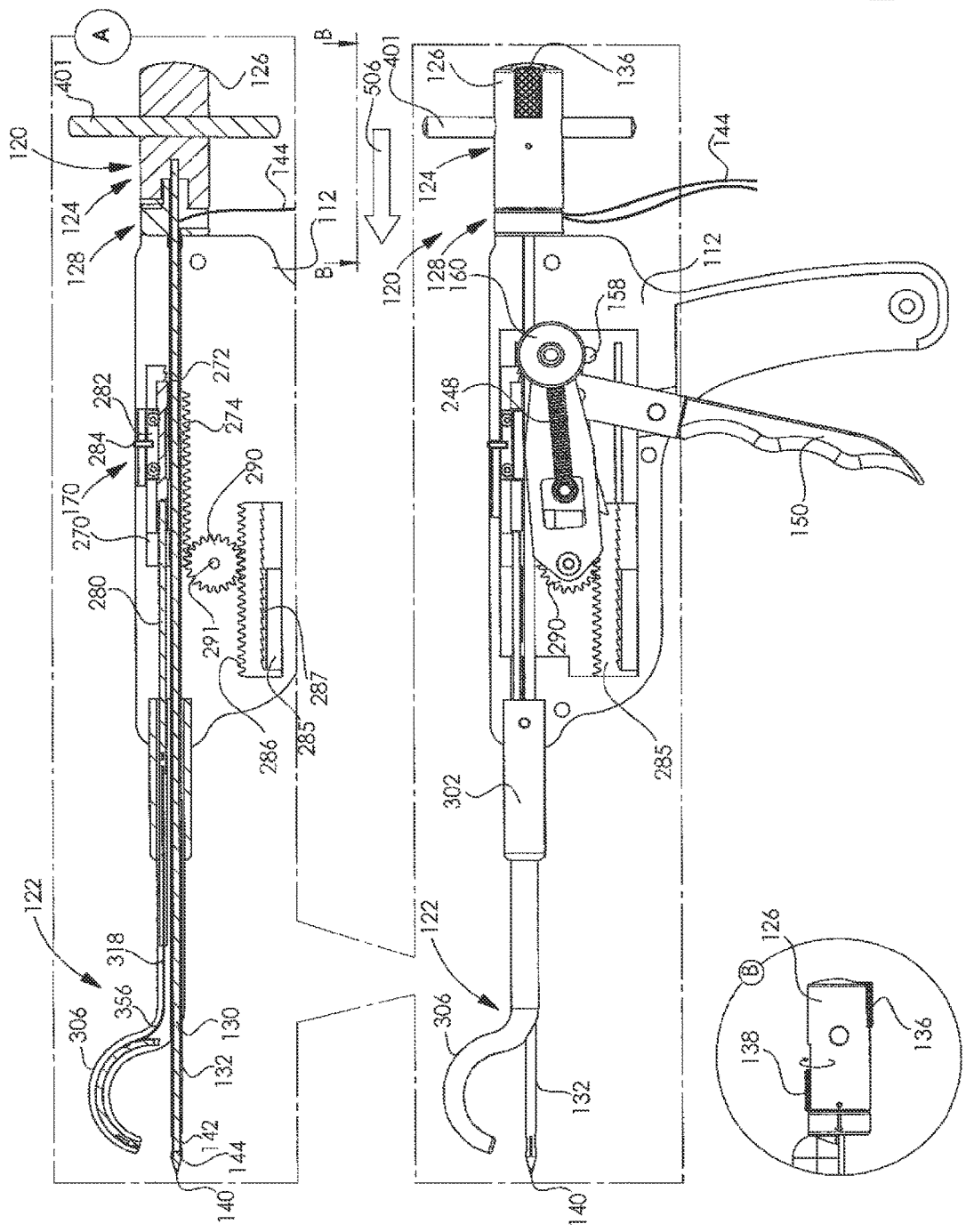

FIGS. 30C and 31D, which correspond generally to FIGS. 3A & 3B, show further and maximum linear forward displacement of bone-engaging pin driving assembly 120 in the arthroscopic surgical device 100, as indicated by an arrow 506. This displacement may be achieved by an operator hammering rearward portion 126 as shown forcing tip 140 and pins 130 and 132 axially through the bone until tip 140 reaches its forwardmost position within the bone such that aperture 142 intersects an arcuate trajectory of needle 162 within the bone. This forwardmost position is defined by engagement of a forward surface 478 of forward portion 128 with a rear surface of the housing.

Alternatively, hammering may be replaced by rotational displacement, such as by using alternative tips 406 or 410 (FIGS. 20B & 20C), which may be driven manually or by using a power drill.

It is also noted that the desired rotational positioning of hollow pin 132 is achieved by lining up a marking 508 on the forward portion 128 with a corresponding marking 510 adjacent the rear surface of the housing. This rotational positioning is required to ensure that aperture 142 is aligned vertically in the sense of FIGS. 3A, 3B and 30C. At this position, the bone-engaging pin driving assembly 120 is axially and rotationally locked in the arthroscopic surgical device 100, by operation of knurled knob 138, as described hereinabove with reference to FIGS. 18A-20.

Figure 30D:
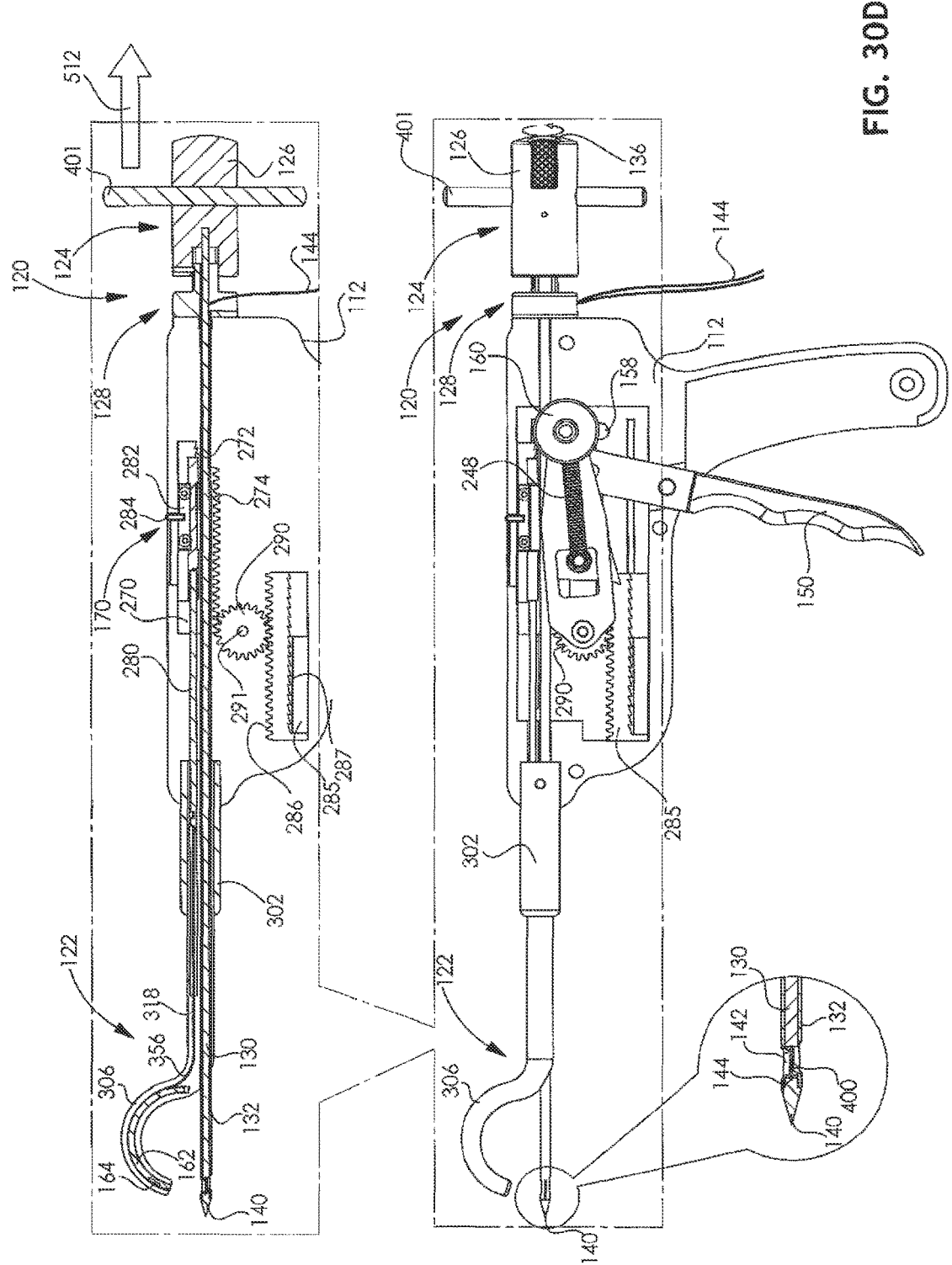
Figure 31E:
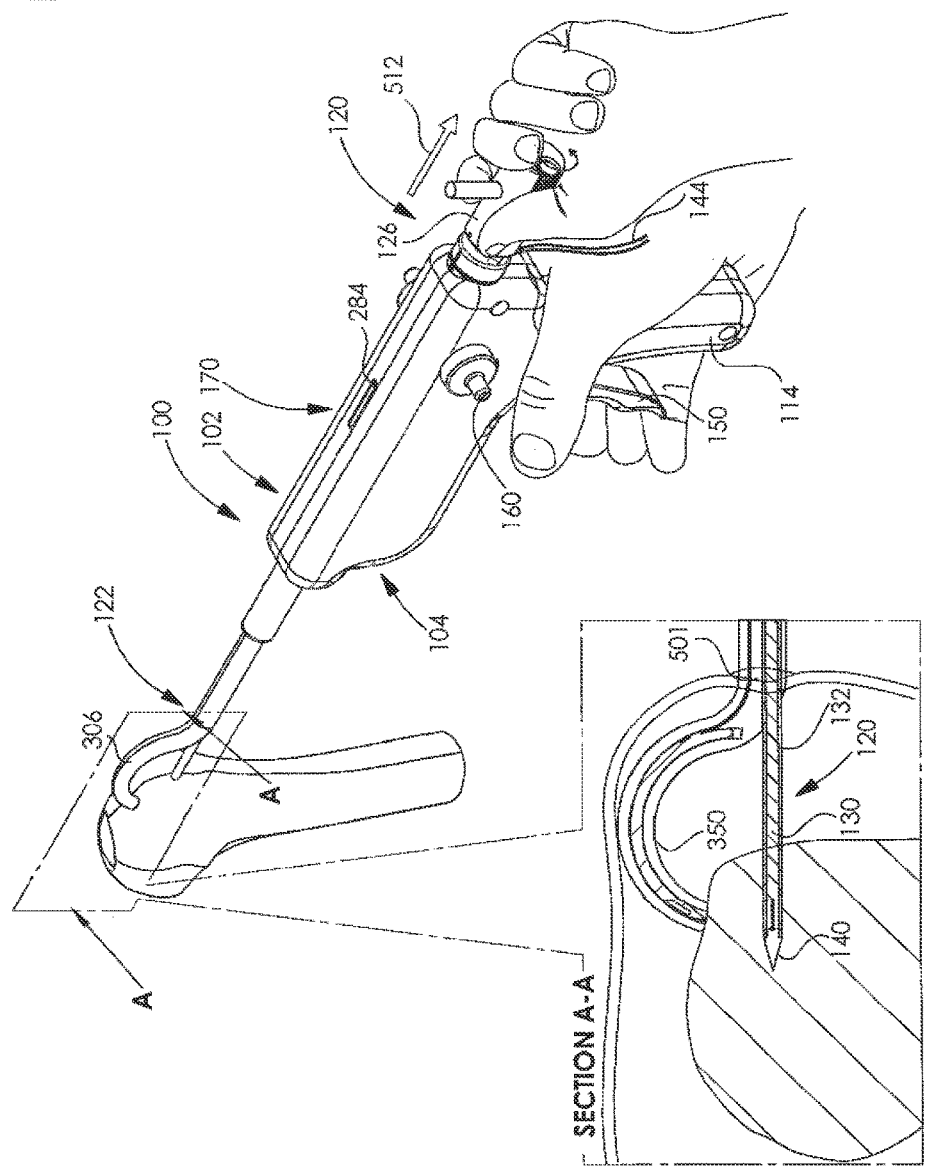

Reference is now made to FIGS. 30D and 31E, which correspond generally to FIGS. 4A and 4B and which show retraction of rod 130 relative to rod 132. This is achieved by unlocking the rearward and forward portions 126 and 128 from each other via suitable rotation of knurled knob 136 and pulling back rearward portion 126 axially from forward portion 128, as indicated by an arrow 512.

It is noted that at this stage indicator 170 shows full retraction of flexible needle driving strip driving shaft 280 and of arcuate tunneling needle 162.

Figure 30E:
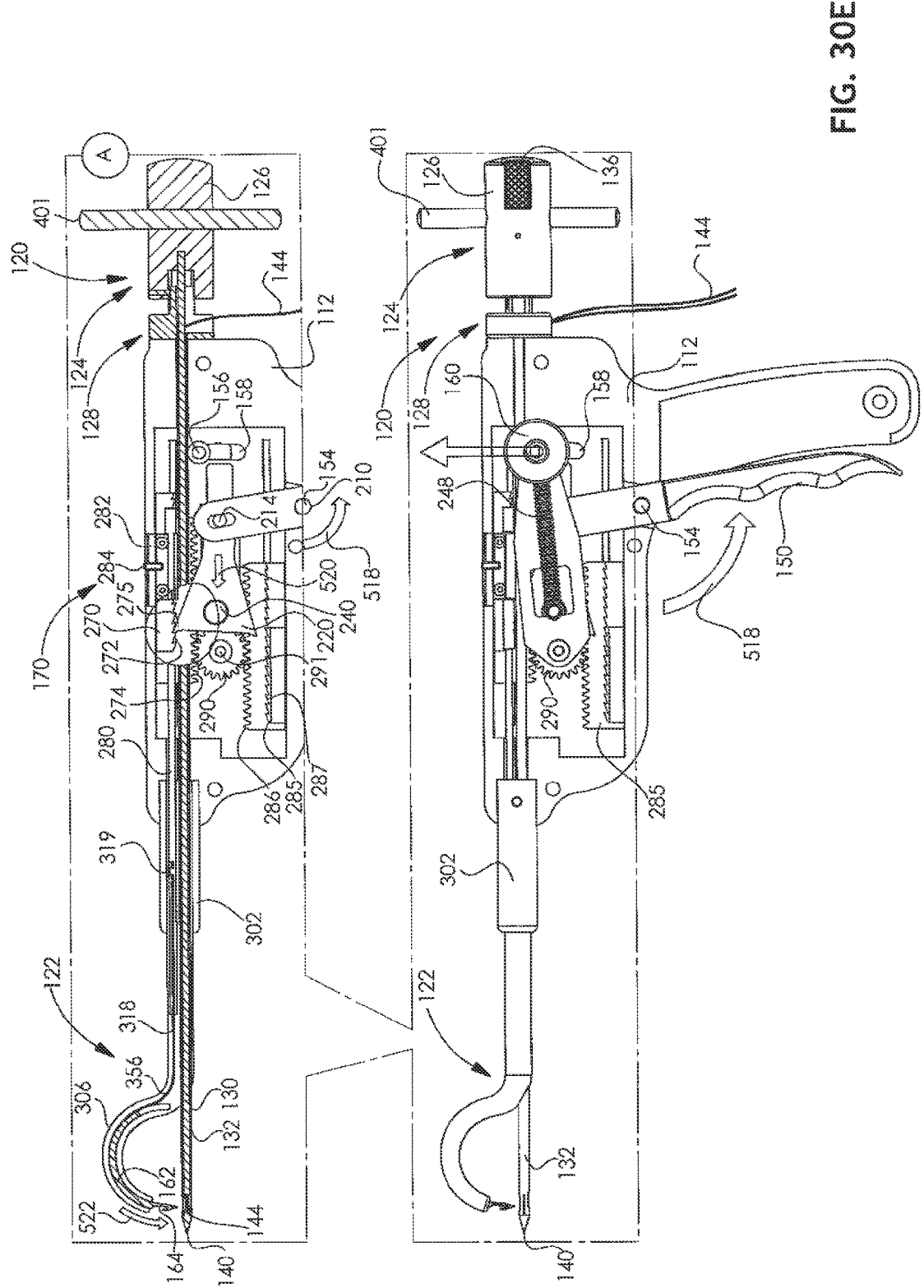
Figure 31F:
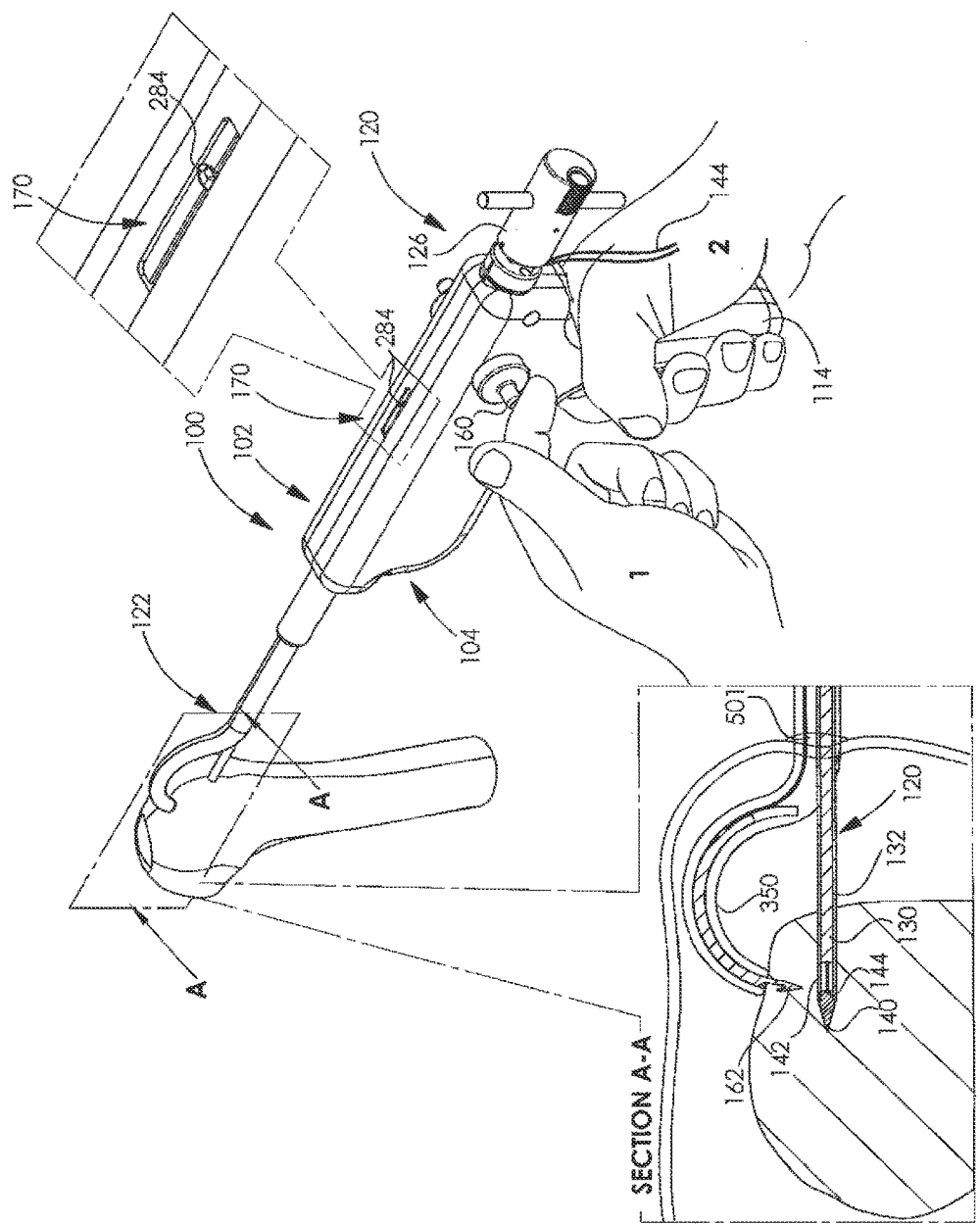

Reference is now made to FIGS. 30E and 31F, which correspond generally to FIGS. 5A & 5B and show partial extension of arcuate tunneling needle 162 through the bone, as indicated by indicator finger 284 of indicator 170. This partial extension follows upward repositioning of knob 160, as indicated by hand 1, followed by squeezing of handle 150, as indicated by hand 2.

Figure 30F:
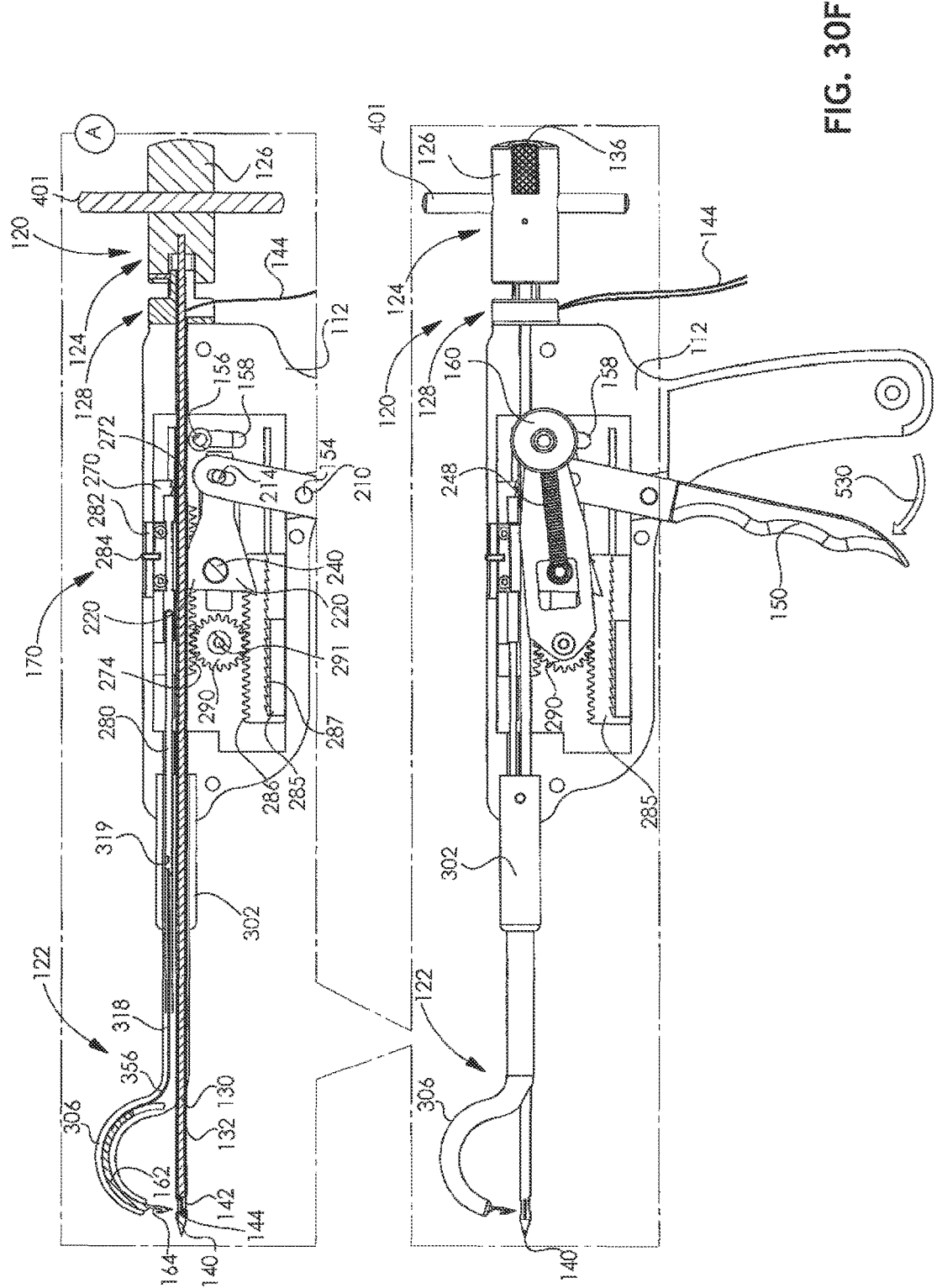
Figure 30G:
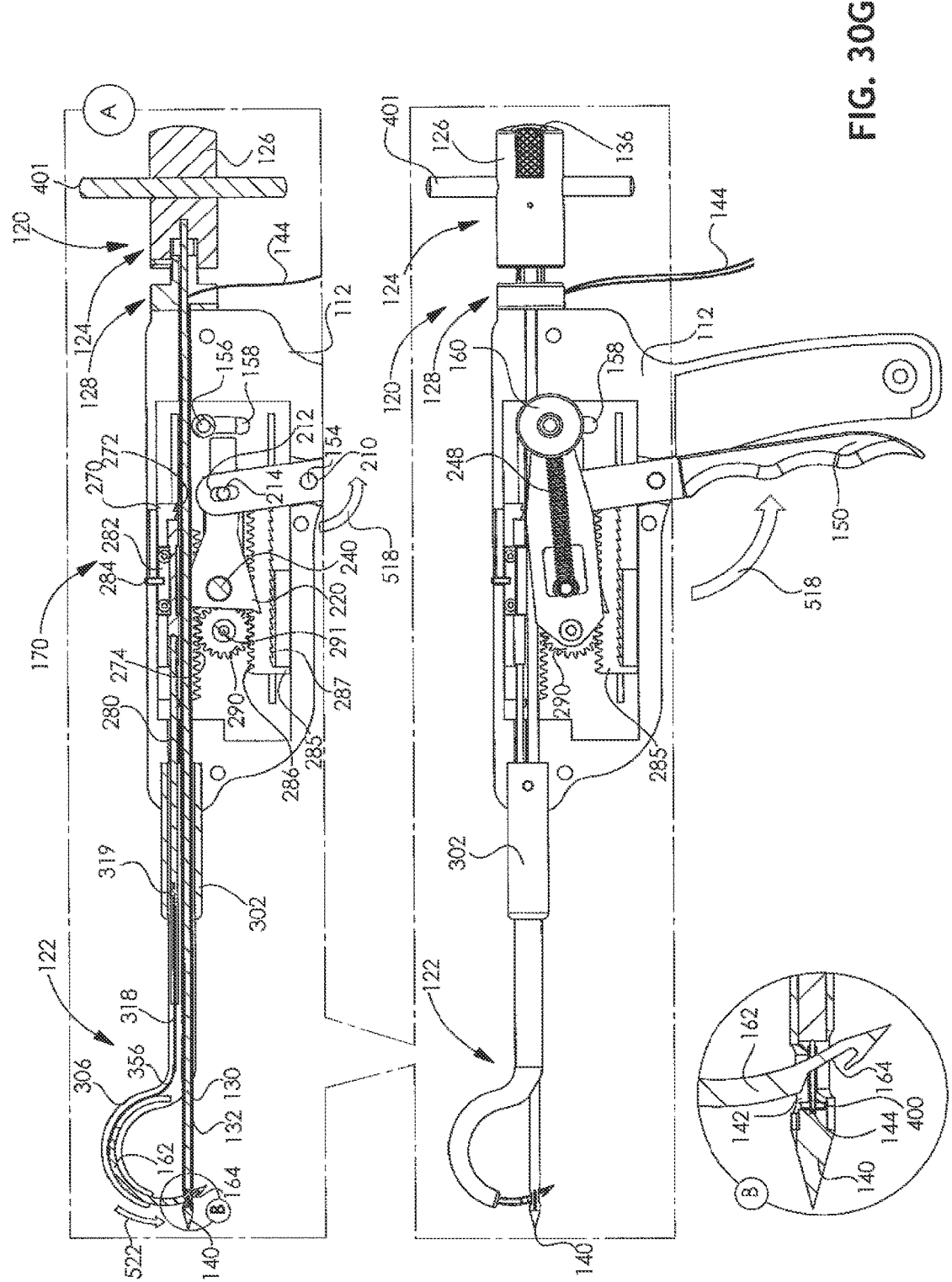
Figure 30H:
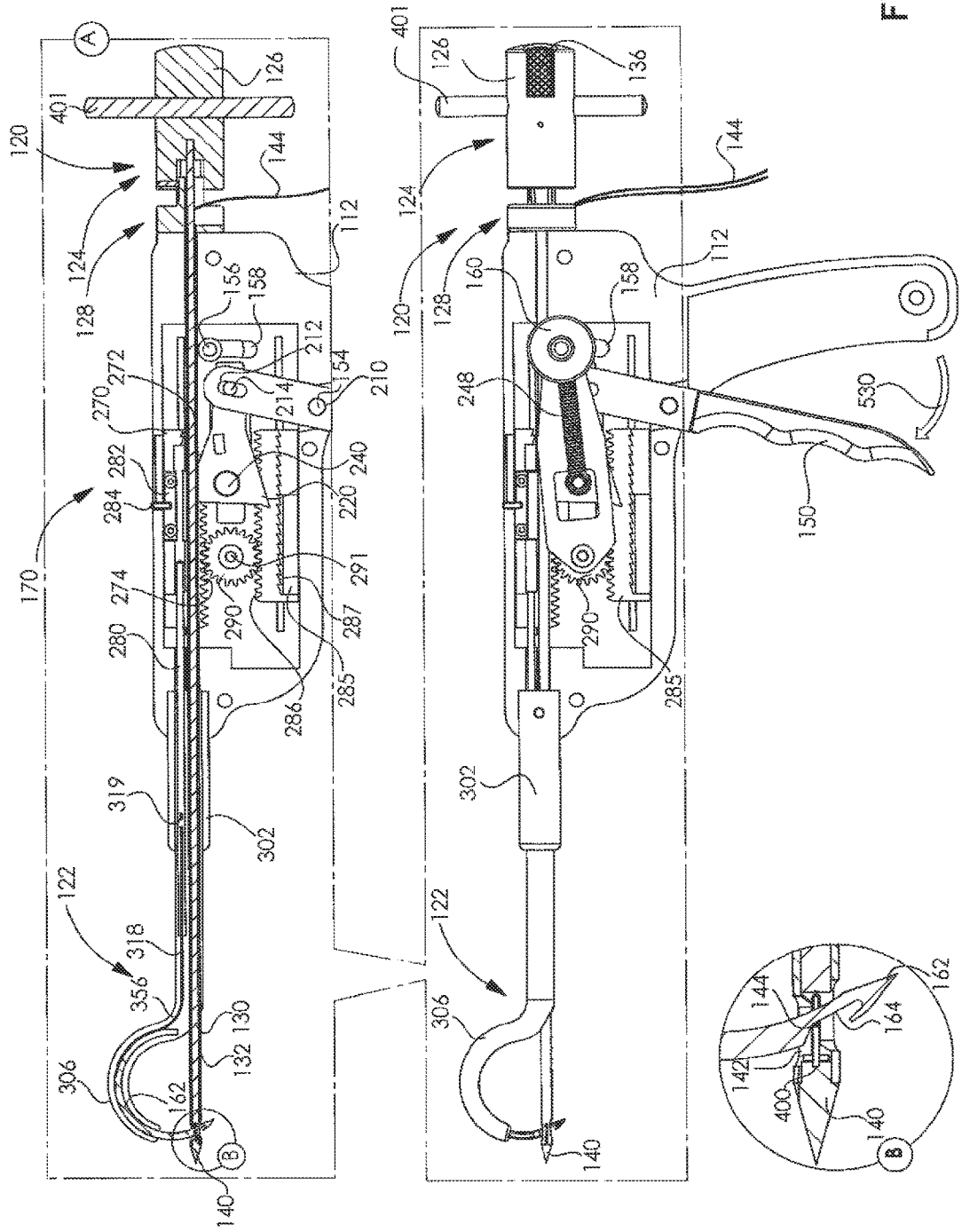
Figure 31G:
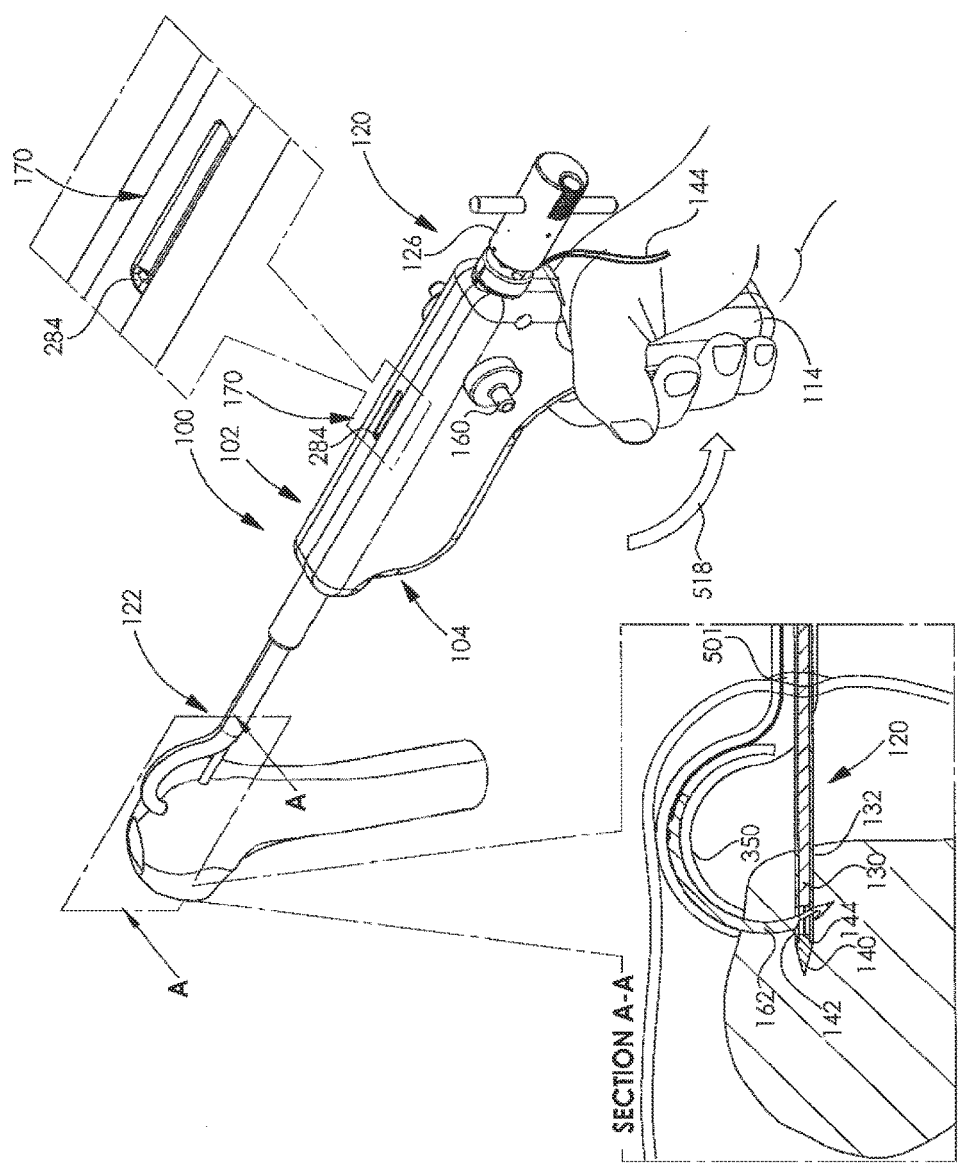

FIGS. 30E, 30F, 30G, which correspond generally to FIGS. 6A & 6B, 30H, particularly at enlargements B in FIGS. 30G and 30H, and 31G show that squeezing on hand-engageable ratchet handle 150 produces rotation thereof, as indicated by an arrow 518, about a rotational axis defined by shaft 154 and, via pin 214, displaces first reciprocal motion connection element 220 linearly forwardly, as indicated by an arrow 520, with pointed corner 275 of connection element 220 in engagement with upper linear toothed rack 272 of double rack linear toothed element 270, thereby driving element 270 and needle driving strip driving shaft 280 forwardly and causing arcuate needle 162, driven thereby, to travel along an arcuate path through the portion 354 of arcuate bore 352 having a rectangular cross section and to extend outwardly into tunneling engagement with the bone, as indicated by arrow 522.

FIG. 30H shows retraction of handle 150, as indicated by an arrow 530, under urging of spring 248 whereby pointed corner 275 is operationally disengaged from rack 272 of double rack linear toothed element 270, such that one or more subsequent squeeze on handle 150 produces further linear forward motion of double rack linear toothed element 270 and consequent further arcuate extension travel of needle 162.

It is appreciated that simultaneous engagement of gear 290 with lower linear toothed gear rack 274 of element 270 and upper linear toothed gear rack 286 of element 285 produces rearward linear motion of element 285 corresponding to forward linear motion of element 270.

Figure 30I:
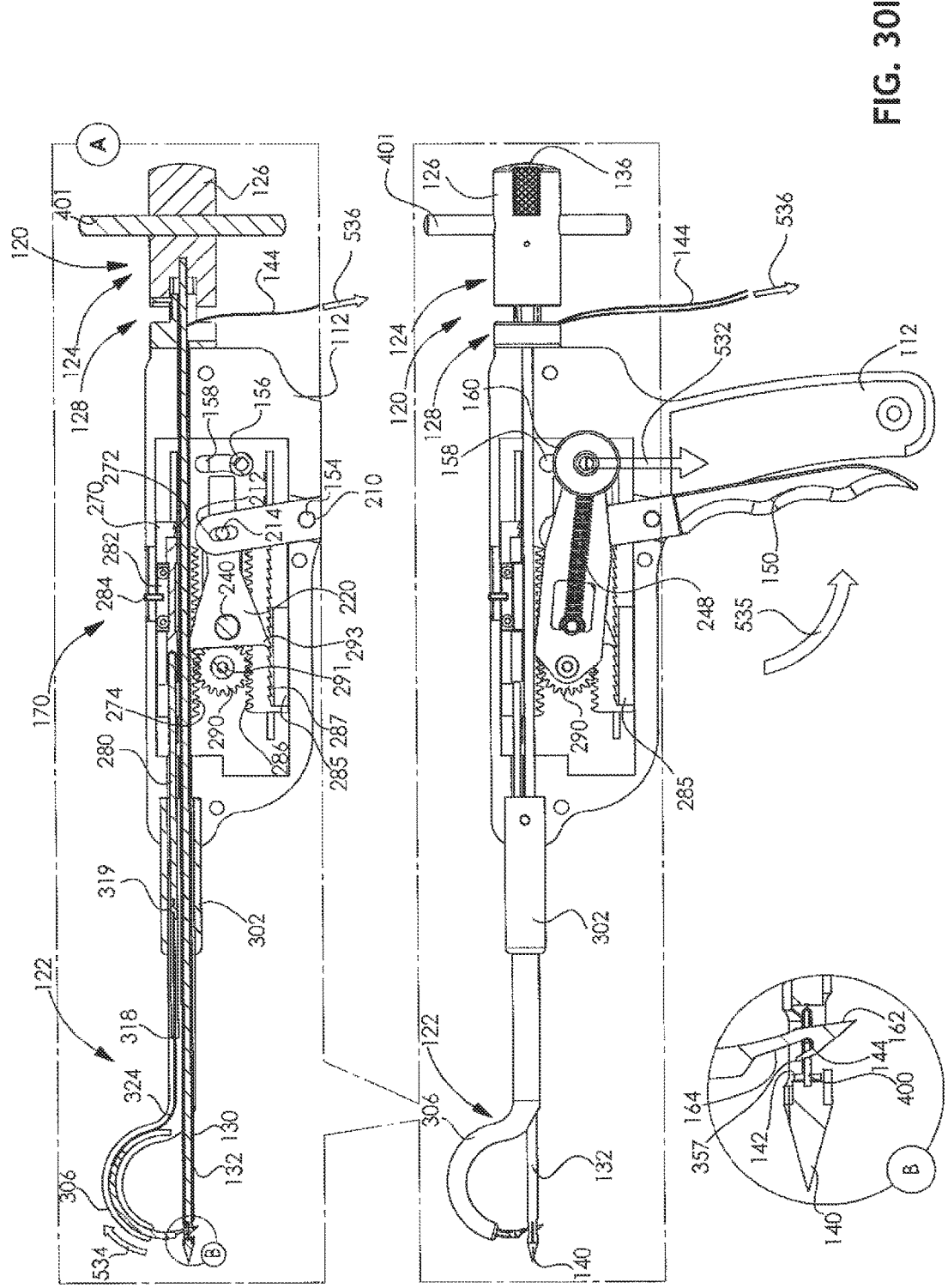
Figure 31H:
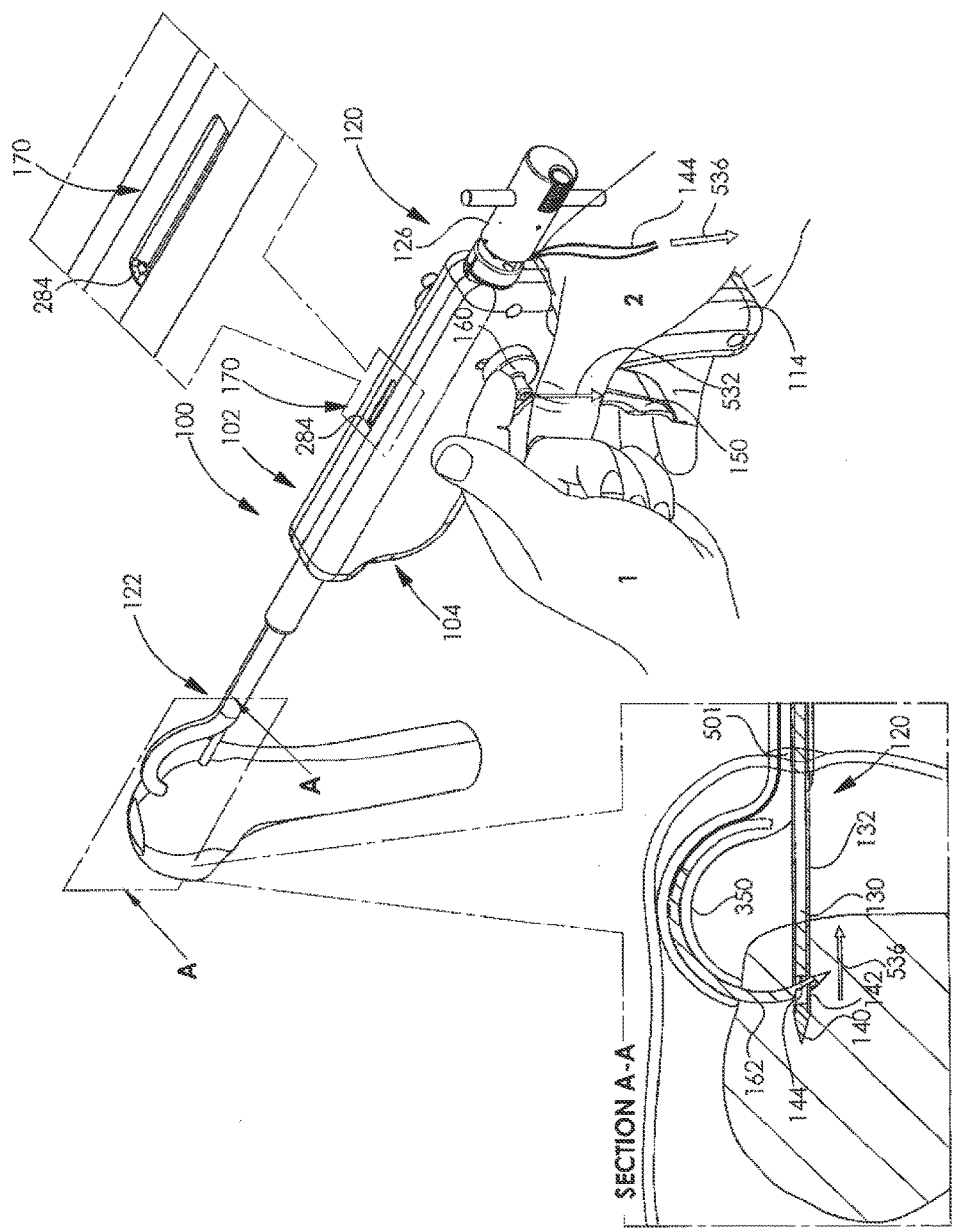

FIGS. 30I and 31H, which correspond generally to FIGS. 7A-8B, show downward repositioning of knob 160, as indicated by an arrow 532 and by hand 1, to provide arcuate retraction of arcuate tunnel needle 162, as indicated by an arrow 534, through the bone, driven by further squeezing of handle 150 as indicated by an arrow 535 and by hand 2. Prior to this retraction, the operator pulls back on suture 144, as indicated by an arrow 536, thereby drawing it into engagement with groove 164 in needle 162, and to be retained therein by partially overlying portion 357 of needle 162, such that retraction of the needle 162 pulls the suture together with it along the arcuate travel path of the needle 162.

Figure 30J:
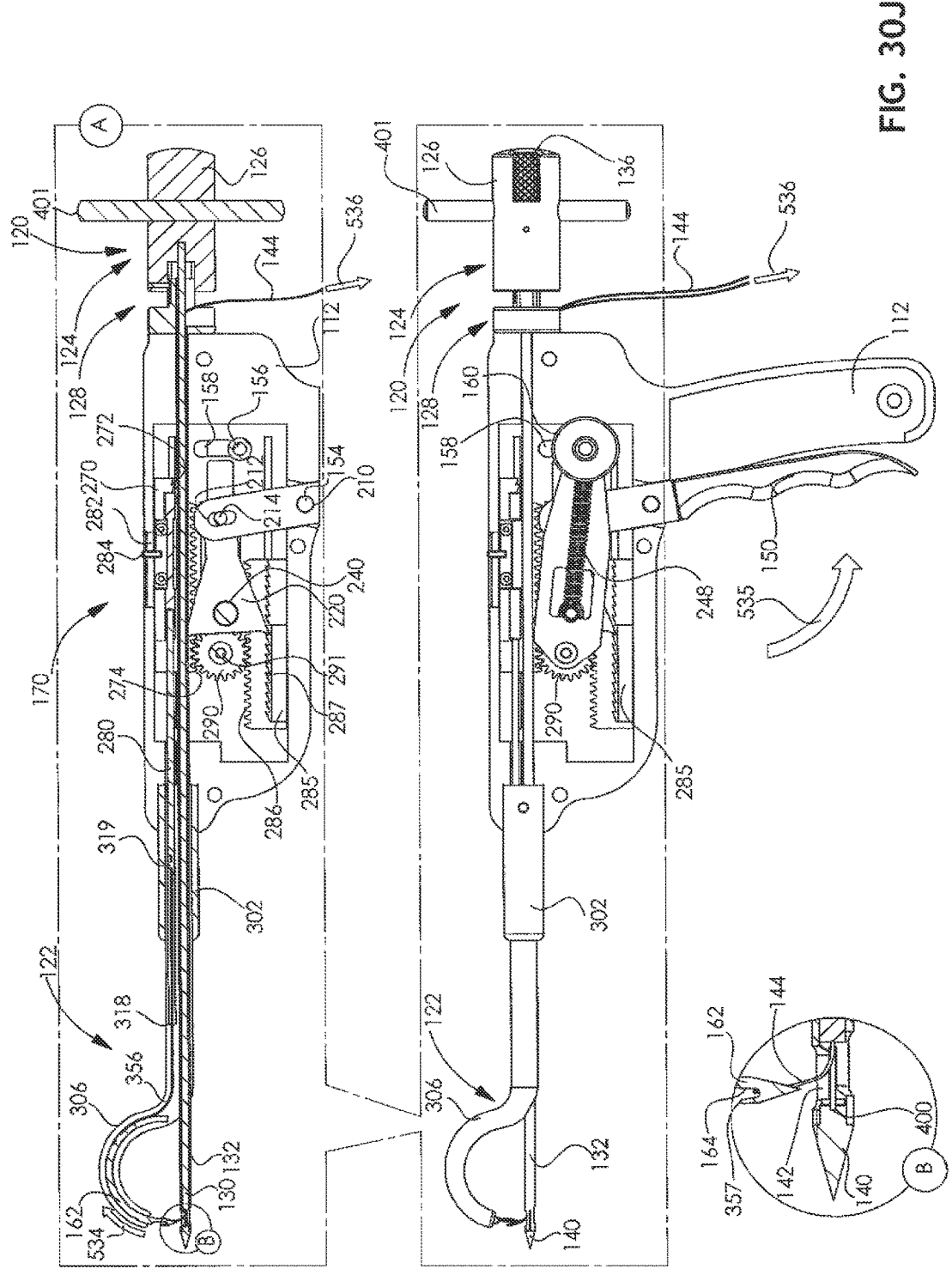
Figure 31I:
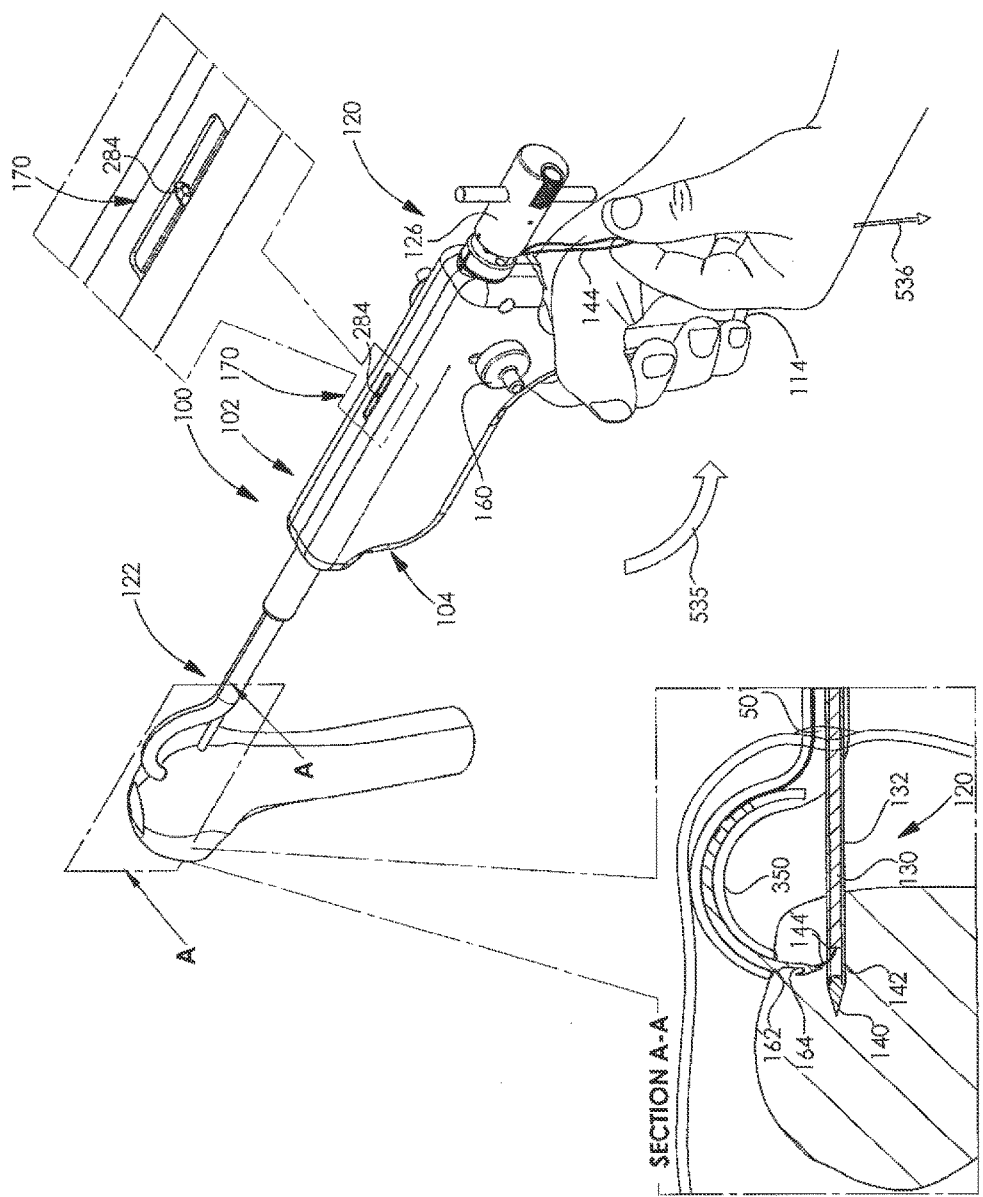

FIGS. 30J & 31I, which correspond generally to FIGS. 9A & 9B, show partial retraction of arcuate tunnel needle 162 in engagement with suture 144, thereby pulling suture 144 through the arcuate passageway being traversed by arcuate needle 162. The partial retraction is provided by further squeezing of handle 150, as indicated by arrow 535. It is appreciated that that during the retraction the operator continues to pulls back on suture 144, as indicated by arrow 536.

Figure 30K:
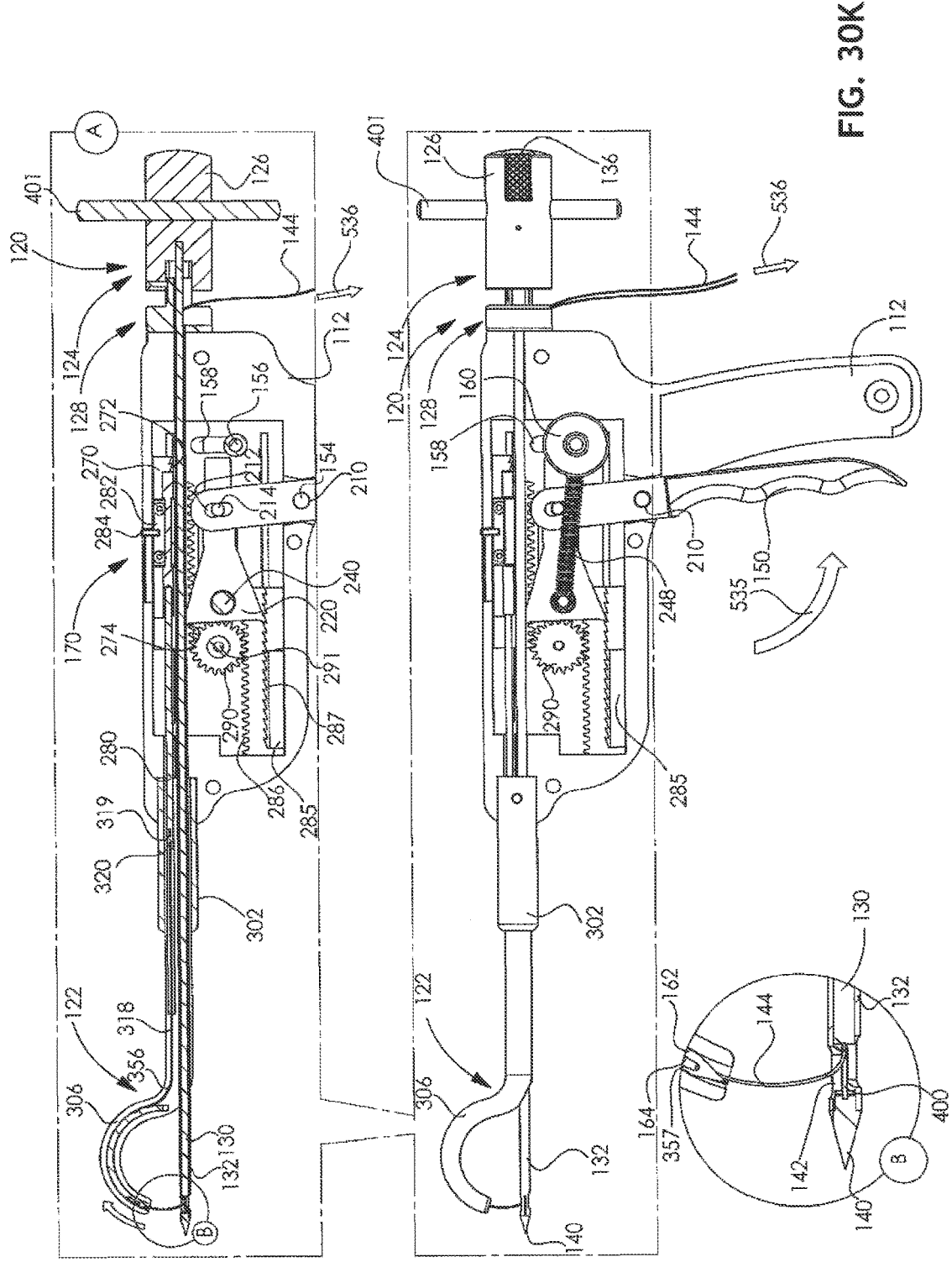
Figure 31J:
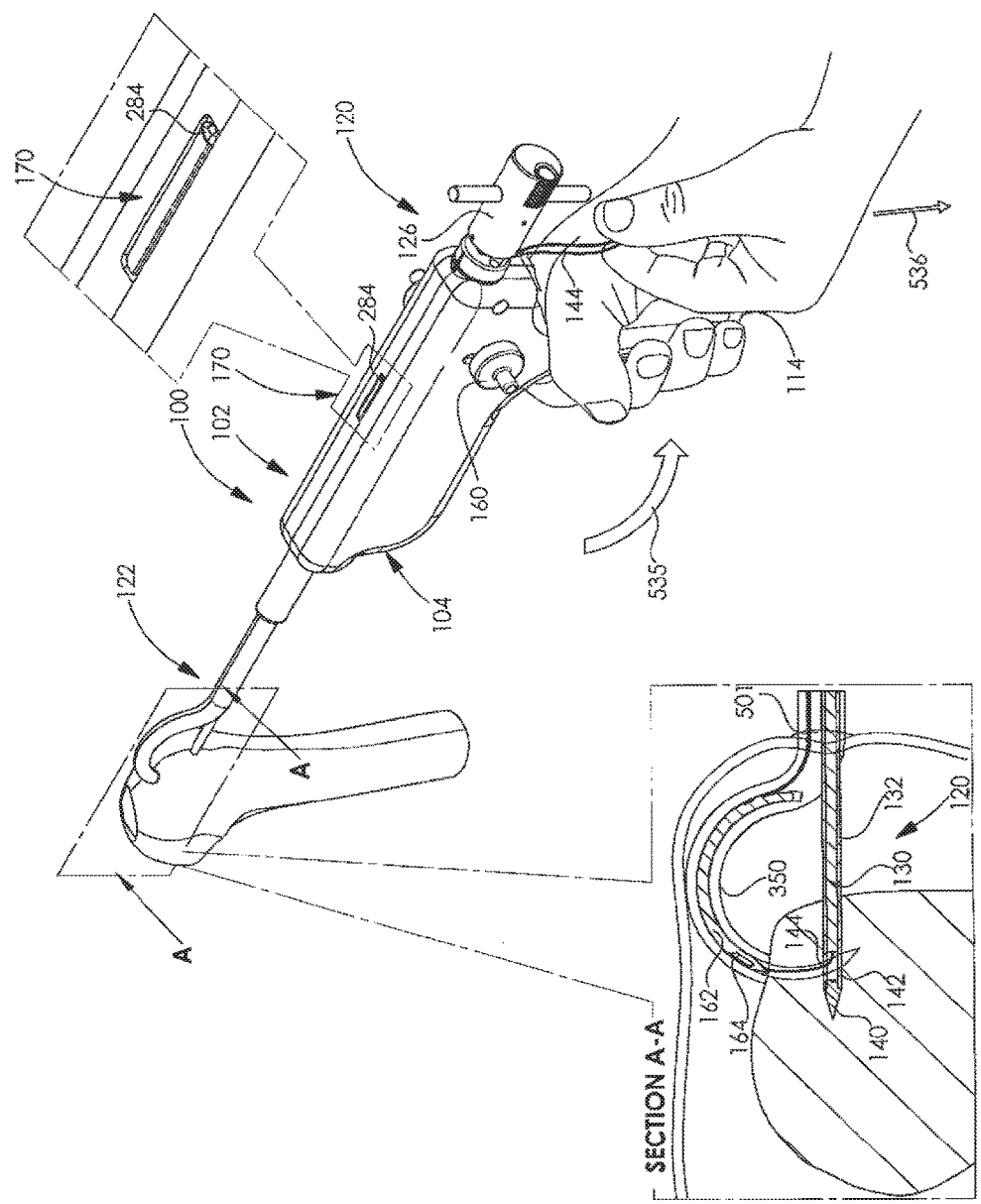

FIGS. 30K and 31J, which correspond generally to FIGS. 10A & 10B, show complete retraction of arcuate tunnel needle 162. The complete retraction of arcuate tunnel needle 162 is indicated by indicator finger 284 of indicator 170. At this stage, suture 144, in doubled-over configuration, extends entirely through the bone along the arcuate path tunneled by needle 162 as described above. The retraction is provided by further squeezing of handle 150, as indicated by arrow 535. It is appreciated that during the retraction the operator continues to pulls back on suture 144, as indicated by arrow 536.

Figure 30L:
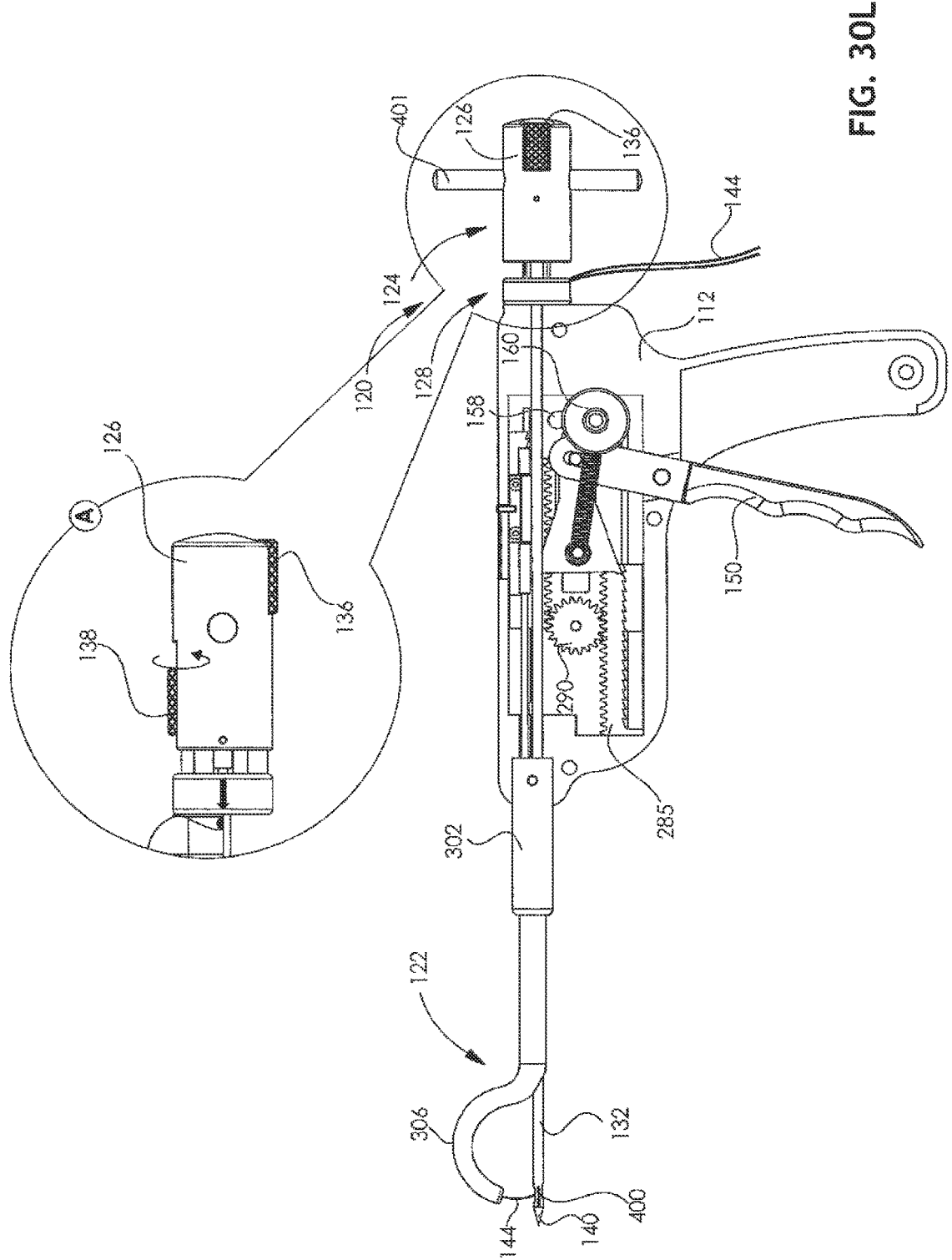
Figure 31K:
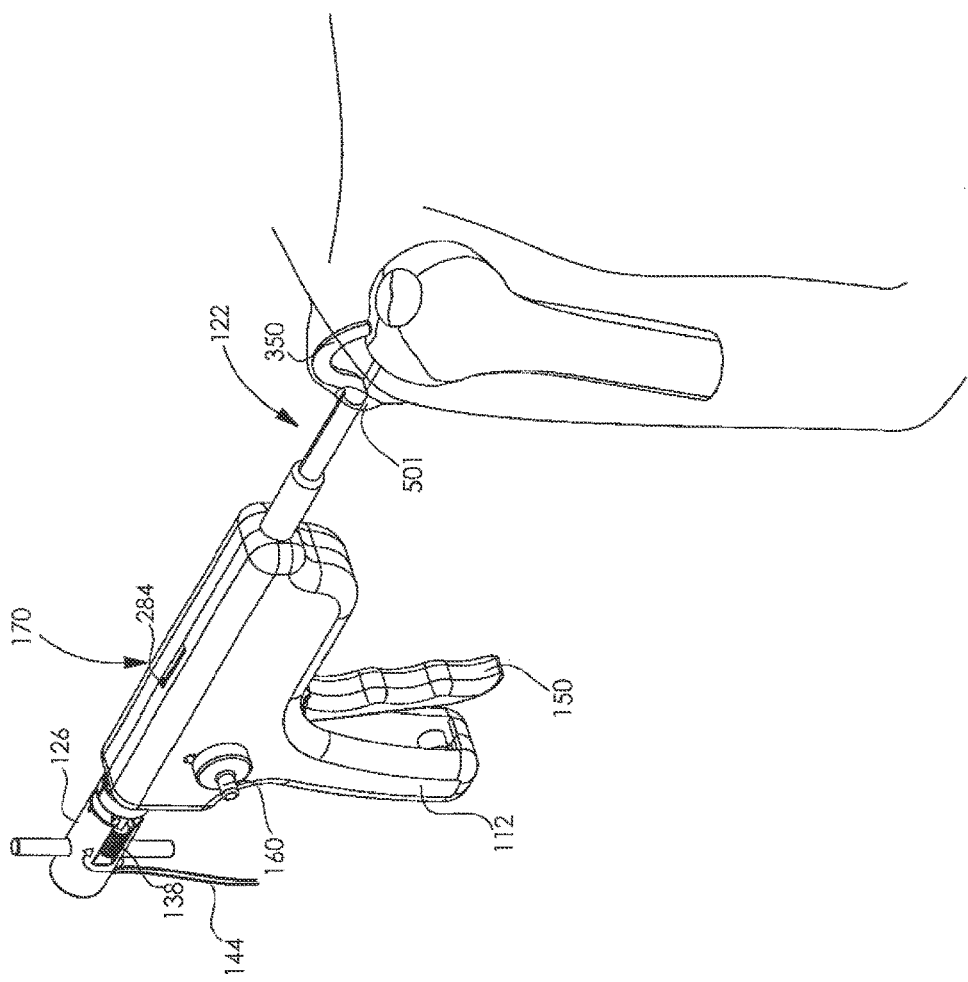

FIGS. 30L and 31K show unlocking of forward portion 128 from the housing, by manipulation of knurled knob 138 as described hereinabove.

Figure 30M:
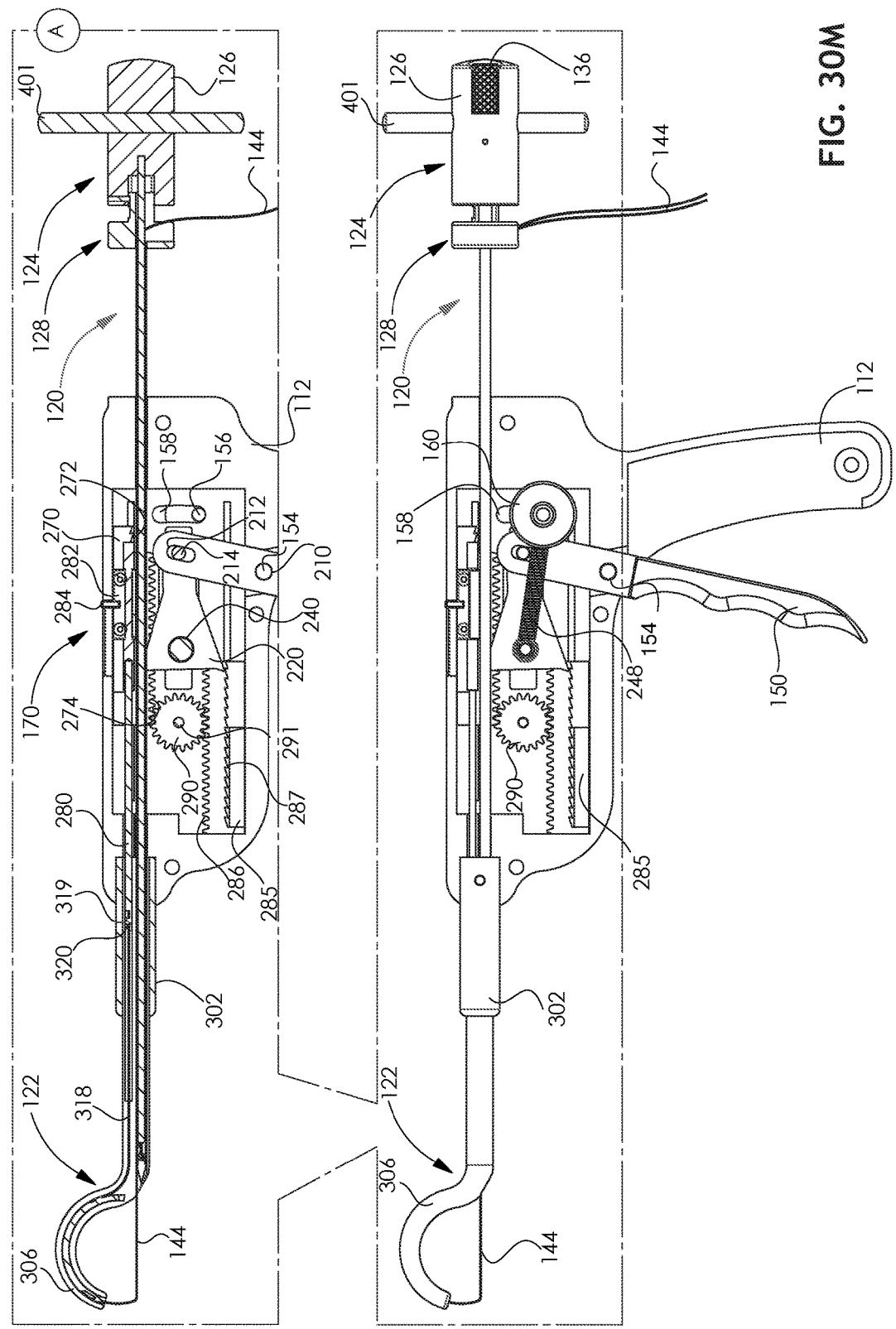
Figure 31L:
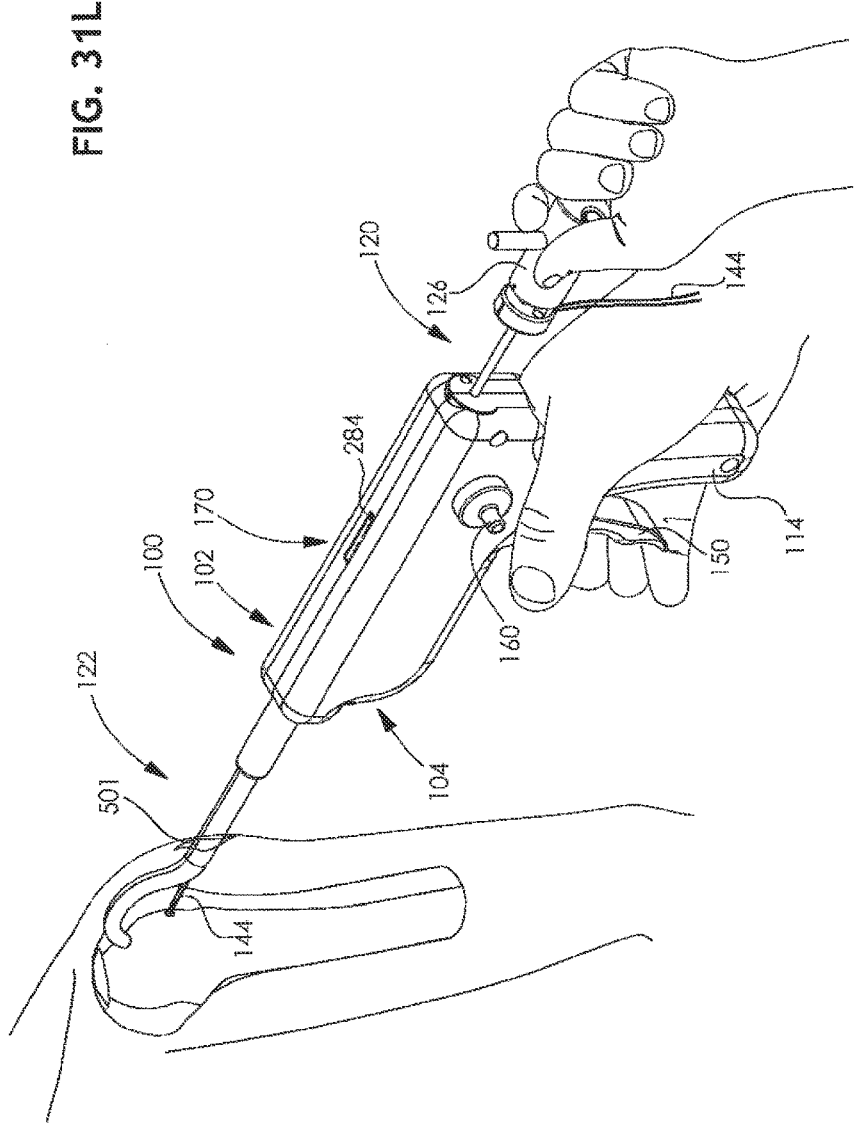

FIGS. 30M and 31L, which correspond generally to FIGS. 11A & 11B, show retraction of bone-engaging pin driving assembly 120 from engagement with the bone, leaving the suture 144 extending through the bone and still being attached to arcuate tunnel needle 162.

Figure 31M:
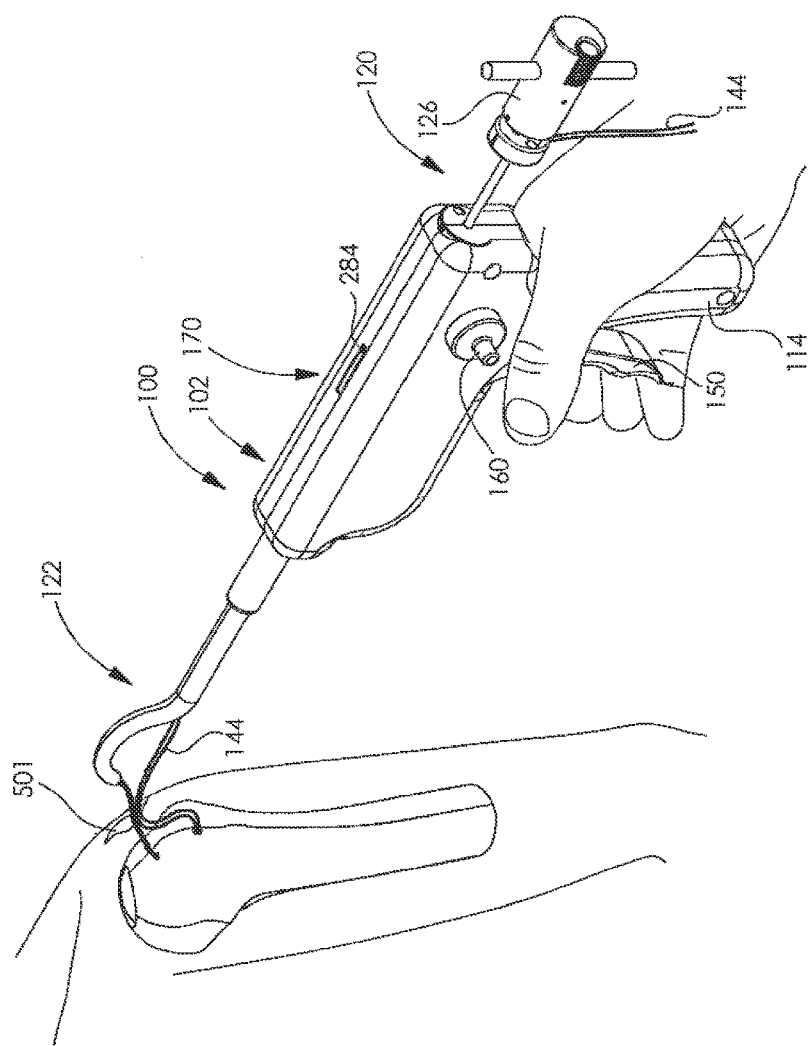

FIG. 31M shows removal of the arthroscopic surgical device 100 from the patient through incision 501.

Figure 30N:
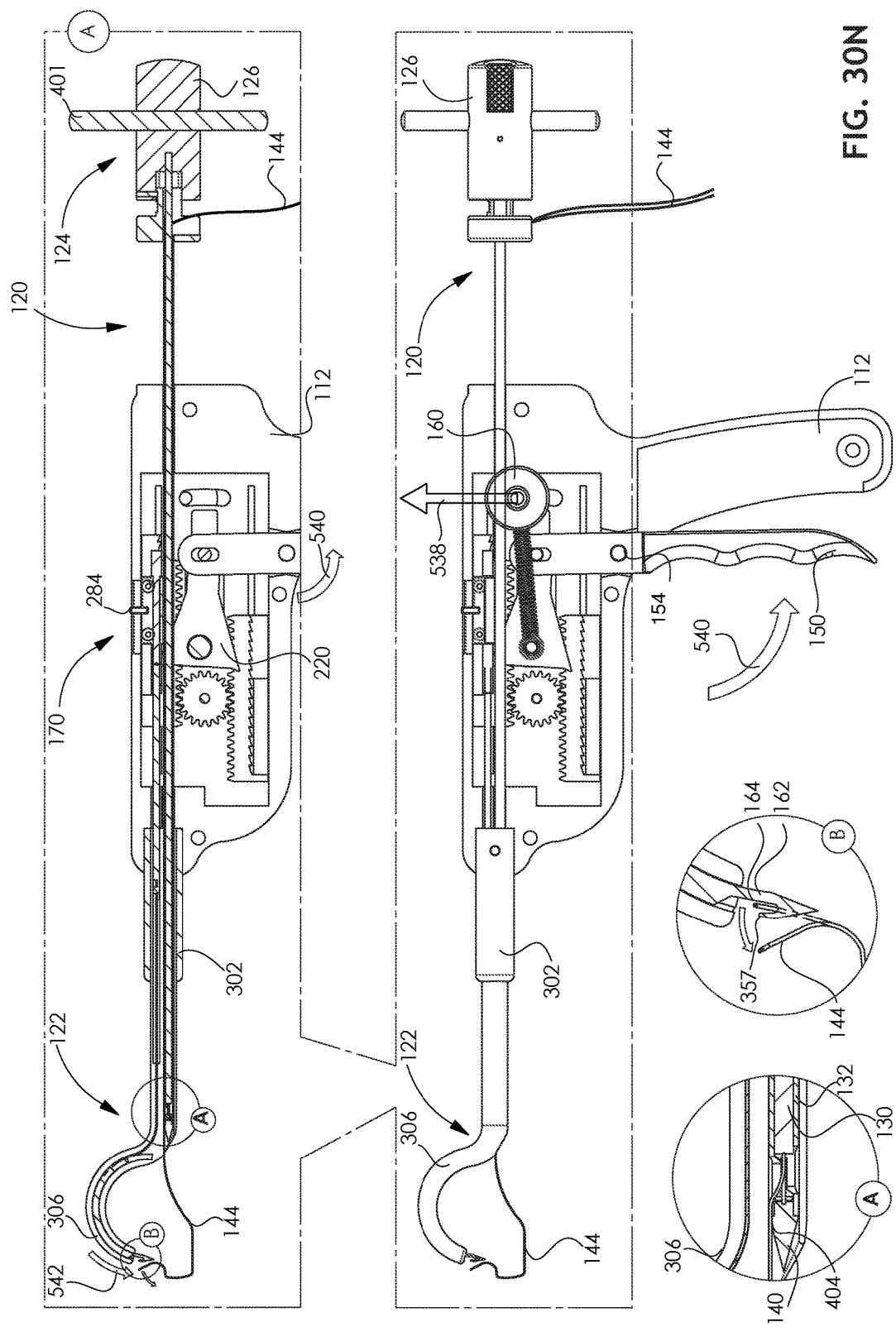
Figure 31N:
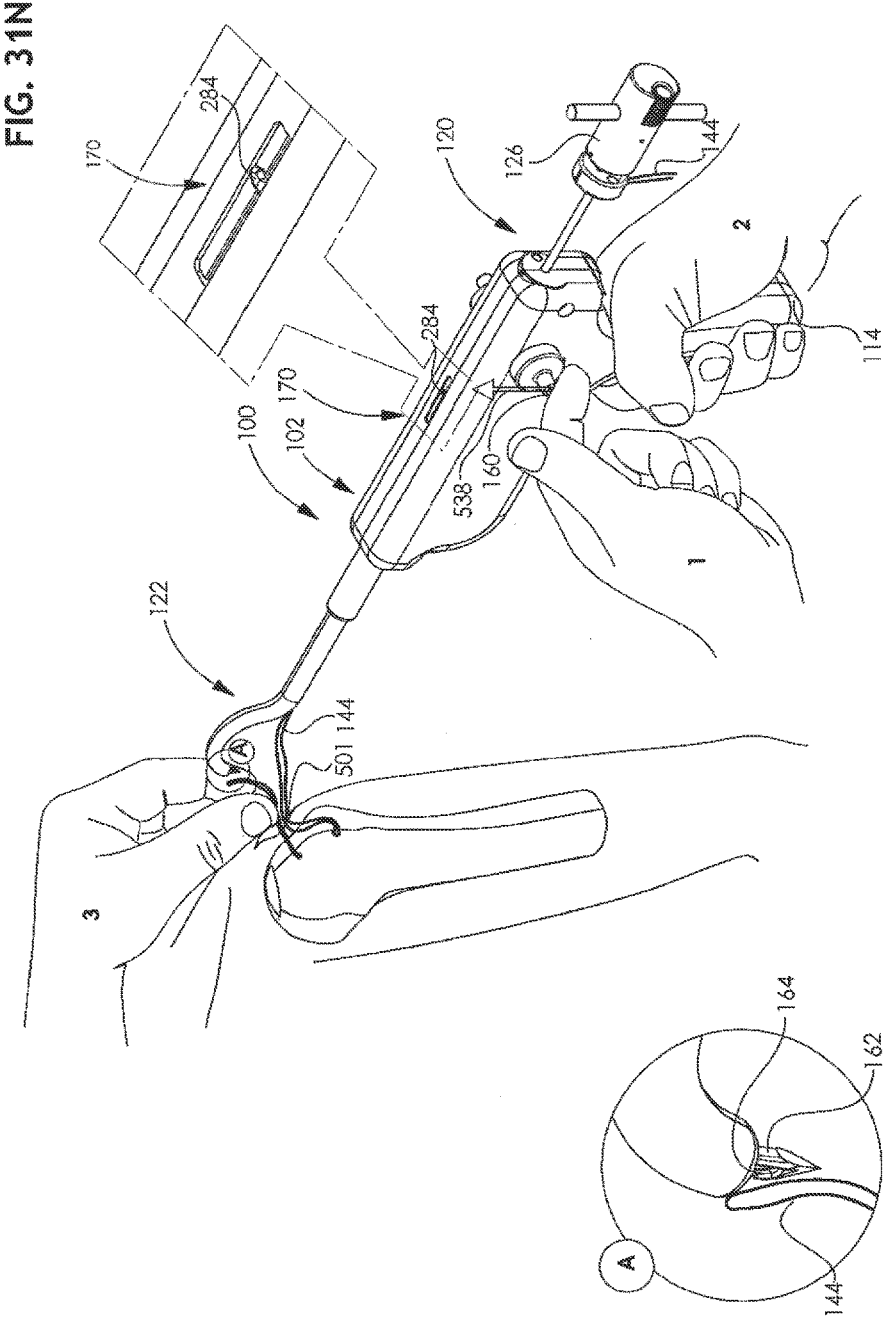

FIGS. 30N and 31N, which correspond generally to FIGS. 12A & 12B, show partial re-extension of arcuate tunnel needle 162 so that the suture 144 can be manually disengaged therefrom. This partial re-extension is achieved by upwardly repositioning knobs 160, as indicated by hand 1, and then operating handle 150, as indicated by hand 2. The partial re-extension is followed by manual disengagement of suture 144, as indicated by hand 3.

Upward repositioning of knobs 160, as indicated by an arrow 538, causes repositioning of connection element 220, causing pointed corner 275 of connection element 220 to engage upper linear toothed ratchet rack 272 of element 270, as seen in FIG. 30E, such that squeezing of handle 150, as indicated by an arrow 540, causes element 270 to be moved linearly forward and thereby drive needle driving strip driving shaft 280 forwardly and cause arcuate needle 162, driven thereby, to partially re-extend, as indicated by an arrow 542.

It will be appreciated by persons skilled in the art that the present invention is not limited by what has been particularly shown and described hereinabove. Rather the scope of the present invention includes both combinations and sub-combinations of the various features described hereinabove as well as modifications thereof which would occur to persons skilled in the art upon reading the foregoing description and which are not in the prior art.

The invention claimed is:

1. An arthroscopic bone tunneling and suturing device comprising:
   a bone-engaging needle driving assembly including a bone-engaging arcuate tunneling needle, said needle having an arcuate shape, and being adapted for arthroscopic insertion into engagement with a patient's bone at a first bone location through an arthroscopic incision and for driving said needle forwardly through said bone, thereby forming a generally arcuate tunnel through said bone from said first bone location at least to a second bone location; and
   a bone-engaging pin driving assembly arranged for operative engagement with said bone-engaging needle driving assembly and being adapted for arthroscopic insertion into engagement with said patient's bone at a third bone location through said arthroscopic incision.

2. An arthroscopic bone tunneling and suturing device according to claim 1 and wherein said bone-engaging pin driving assembly is adapted for mounting a suture thereon and positioning said suture so that it can be engaged by said needle at said second bone location.

3. An arthroscopic bone tunneling and suturing device according to claim 2 and wherein said bone-engaging needle driving assembly is also adapted for retracting said needle, in engagement with said suture, back through said generally arcuate tunnel in said bone from said second bone location.

4. An arthroscopic bone tunneling and suturing device according to claim 2 and wherein said bone-engaging pin driving assembly comprises at least one bone tunneling pin which is adapted to tunnel through said bone along a generally linear tunneling path from said third location to said second location at which said generally linear tunneling path intersects said generally arcuate tunnel, thereby positioning said suture so that it can be engaged by said needle at said second bone location.

5. An arthroscopic bone tunneling and suturing device according to claim 1 and wherein said bone-engaging pin driving assembly is separate from said bone-engaging needle driving assembly and is selectably engageable therewith and disengageable therefrom.

6. An arthroscopic bone tunneling and suturing device according to claim 1 and wherein said bone engaging pin driving assembly comprises an inner pin and an outer hollow pin in which said inner pin is slidably disposed.

7. An arthroscopic bone tunneling and suturing device according to claim 6 and wherein said outer hollow pin is formed with a pointed tip and with a throughgoing aperture.

8. An arthroscopic bone tunneling and suturing device according to claim 7 and wherein a suture extends between said inner pin and said outer pin, said suture being looped about said inner pin interiorly of said outer pin so as to be engageable by said needle through said throughgoing aperture.

9. An arthroscopic bone tunneling and suturing device according to claim 7 and wherein said bone-engaging pin driving assembly also comprises a base assembly including a forward portion and a rearward portion, said inner pin being coupled to said rearward portion and said outer pin being coupled to said forward portion.

10. An arthroscopic bone tunneling and suturing device according to claim 9 and wherein said outer hollow pin is also formed with a throughgoing side wall slot for accommodating part of said suture.

11. An arthroscopic bone tunneling and suturing device according to claim 10 and wherein said suture is wound around a forward end of said inner pin and between said forward end of said inner pin and said pointed tip and extends between said inner pin and said outer pin and partially lies in said throughgoing slot on both sides of said inner pin.

12. An arthroscopic bone tunneling and suturing device according to claim 9 and wherein said base assembly is selectably lockable to a housing which encloses part of said bone-engaging needle driving assembly.

13. An arthroscopic bone tunneling and suturing device according to claim 9 and wherein said forward portion and said rearward portion of said base assembly are selectably lockable to each other and axially slidable with respect to each other, thereby to provide limited retractability of said inner pin with respect to said outer pin.

14. An arthroscopic bone tunneling and suturing device according to claim 1 and wherein said bone-engaging needle driving assembly includes a flexible needle driving strip which drives said bone engaging needle through said bone.

\* \* \* \* \*